US010975436B2

(12) United States Patent
Umansky et al.

(10) Patent No.: US 10,975,436 B2
(45) Date of Patent: Apr. 13, 2021

(54) METHODS OF USING MIRNA FROM BODILY FLUIDS FOR DIAGNOSIS AND MONITORING OF NEURODEVELOPMENTAL DISORDERS

(71) Applicant: DiamiR, LLC, Princeton, NJ (US)

(72) Inventors: Samuil R. Umansky, Princeton, NY (US); Kira S. Sheinerman, New York, NY (US); Vladimir G. Tsivinsky, Sharon, MA (US)

(73) Assignee: DIAMIR, LLC, Princeton, NJ (US)

( * ) Notice: Subject to any disclaimer, the term of this patent is extended or adjusted under 35 U.S.C. 154(b) by 52 days.

(21) Appl. No.: 16/028,206

(22) Filed: Jul. 5, 2018

(65) Prior Publication Data

US 2018/0312925 A1    Nov. 1, 2018

Related U.S. Application Data

(63) Continuation-in-part of application No. PCT/US2017/012258, filed on Jan. 5, 2017.

(60) Provisional application No. 62/529,372, filed on Jul. 6, 2017, provisional application No. 62/396,577, filed on Sep. 19, 2016, provisional application No. 62/274,999, filed on Jan. 5, 2016.

(51) Int. Cl.
| | | |
|---|---|---|
| *C12Q 1/68* | (2018.01) |
| *C07H 21/02* | (2006.01) |
| *C07H 21/04* | (2006.01) |
| *C12Q 1/6883* | (2018.01) |
| *G01N 33/49* | (2006.01) |
| *G01N 33/493* | (2006.01) |

(52) U.S. Cl.
CPC ......... *C12Q 1/6883* (2013.01); *G01N 33/492* (2013.01); *G01N 33/493* (2013.01); *C12Q 2600/112* (2013.01); *C12Q 2600/118* (2013.01); *C12Q 2600/158* (2013.01); *C12Q 2600/178* (2013.01)

(58) Field of Classification Search
CPC ............ C12Q 1/6883; C12Q 2600/112; C12Q 2600/118; C12Q 2600/178; G01N 33/492; G01N 33/493
See application file for complete search history.

(56) References Cited

U.S. PATENT DOCUMENTS

| | | |
|---|---|---|
| 4,785,507 A | 11/1988 | Miyazaki et al. |
| 4,829,304 A | 5/1989 | Baird |
| 4,939,663 A | 7/1990 | Baird |
| 7,653,509 B2 | 1/2010 | Bagwell |

(Continued)

FOREIGN PATENT DOCUMENTS

| | | |
|---|---|---|
| CN | 101942502 A | 1/2011 |
| CN | 101962685 A | 2/2011 |

(Continued)

OTHER PUBLICATIONS

Urdinguio et al. (Epigenetics, 2010 vol. 5:656-663).*

(Continued)

*Primary Examiner* — Terra C Gibbs

(74) *Attorney, Agent, or Firm* — Troutman Pepper Hamilton Sanders LLP

(57) ABSTRACT

The invention provides methods for diagnosis and monitoring of Rett syndrome and other neurodevelopmental disorders by quantitative analysis of miRNAs in bodily fluids.

14 Claims, 31 Drawing Sheets

(56) References Cited

U.S. PATENT DOCUMENTS

| | | |
|---|---|---|
| 7,897,356 B2 | 3/2011 | Klass et al. |
| 7,993,831 B2 | 8/2011 | Latham et al. |
| 8,486,626 B2 | 7/2013 | Umansky et al. |
| 8,632,967 B2 | 1/2014 | Kuroda et al. |
| 8,648,017 B2 | 2/2014 | Umansky et al. |
| 9,422,547 B1 | 8/2016 | Johnson et al. |
| 9,447,471 B2 | 9/2016 | Qu et al. |
| 9,540,692 B2 | 1/2017 | Xu |
| 9,556,487 B2 * | 1/2017 | Umansky ............ C12Q 1/6886 |
| 9,605,315 B2 | 3/2017 | Patel et al. |
| 9,611,511 B2 | 4/2017 | Keller et al. |
| 9,708,667 B2 | 7/2017 | Yanai et al. |
| 9,726,676 B2 | 8/2017 | Grabe et al. |
| 9,790,554 B2 | 10/2017 | Keller et al. |
| 9,803,242 B2 | 10/2017 | Umansky et al. |
| 9,809,857 B2 | 11/2017 | Wang |
| 9,933,440 B2 | 4/2018 | Goetzl |
| 2006/0034810 A1 | 2/2006 | Riley et al. |
| 2007/0161004 A1 | 7/2007 | Brown et al. |
| 2008/0020390 A1 | 1/2008 | Mitchell et al. |
| 2008/0139801 A1 | 6/2008 | Umansky et al. |
| 2008/0171667 A1 | 7/2008 | Brown et al. |
| 2009/0004668 A1 | 1/2009 | Chen et al. |
| 2009/0075258 A1 | 3/2009 | Latham et al. |
| 2009/0081640 A1 | 3/2009 | Umansky et al. |
| 2009/0176723 A1 | 7/2009 | Brown et al. |
| 2010/0151480 A1 | 6/2010 | Taylor et al. |
| 2010/0167937 A1 | 7/2010 | Goldknopf et al. |
| 2010/0167948 A1 | 7/2010 | Krichevsky et al. |
| 2010/0184046 A1 | 7/2010 | Klass et al. |
| 2010/0196426 A1 | 8/2010 | Skog et al. |
| 2010/0216139 A1 | 8/2010 | Galas et al. |
| 2010/0227908 A1 | 9/2010 | Cairns |
| 2010/0267804 A1 | 10/2010 | Port et al. |
| 2010/0279292 A1 | 11/2010 | Marsh et al. |
| 2010/0286044 A1 | 11/2010 | Litman et al. |
| 2010/0323357 A1 | 12/2010 | Nana-Sinkam et al. |
| 2011/0003704 A1 | 1/2011 | Skog et al. |
| 2011/0053157 A1 | 3/2011 | Skog et al. |
| 2011/0053158 A1 | 3/2011 | Mambo et al. |
| 2011/0086348 A1 | 4/2011 | Prasad et al. |
| 2011/0111976 A1 | 5/2011 | Fare et al. |
| 2011/0117111 A1 | 5/2011 | Kwon et al. |
| 2011/0117560 A1 | 5/2011 | Spinale et al. |
| 2011/0143360 A1 | 6/2011 | Kuroda et al. |
| 2011/0160285 A1 | 6/2011 | Anderson et al. |
| 2011/0160290 A1 | 6/2011 | Tewari |
| 2012/0034608 A1 | 2/2012 | Zhou et al. |
| 2012/0093936 A1 | 4/2012 | Lindenberg et al. |
| 2012/0184599 A1 | 7/2012 | Marcet et al. |
| 2012/0252693 A1 | 10/2012 | Umansky et al. |
| 2012/0270746 A1 | 10/2012 | Kuroda et al. |
| 2013/0012403 A1 | 1/2013 | Hu |
| 2013/0131194 A1 | 5/2013 | Skog et al. |
| 2014/0120545 A1 | 5/2014 | Umansky et al. |
| 2014/0170648 A1 | 6/2014 | Kuroda et al. |
| 2014/0194319 A1 | 7/2014 | Skog et al. |
| 2014/0194613 A1 | 7/2014 | Skog et al. |
| 2014/0256562 A1 | 9/2014 | Umansky et al. |
| 2014/0259192 A1 | 9/2014 | Saarma et al. |
| 2014/0357507 A1 | 12/2014 | Umansky et al. |
| 2015/0005365 A1 | 1/2015 | Zakharenko et al. |
| 2016/0083449 A1 | 3/2016 | Schmitt et al. |
| 2016/0273043 A1 | 9/2016 | Umansky et al. |
| 2017/0107575 A1 | 4/2017 | Umansky et al. |
| 2017/0362656 A1 | 12/2017 | Umansky et al. |

FOREIGN PATENT DOCUMENTS

| | | |
|---|---|---|
| EP | 0381176 A2 | 8/1990 |
| EP | 2699666 B1 | 2/2014 |
| EP | 2699697 A1 | 2/2014 |
| EP | 2496714 B1 | 8/2016 |
| EP | 3071712 A1 | 9/2016 |
| EP | 3118334 A1 | 1/2017 |
| EP | 3133147 A1 | 2/2017 |
| JP | 2010536372 A | 12/2010 |
| JP | 2010538653 A | 12/2010 |
| JP | 5624470 B2 | 11/2014 |
| RU | 2367959 C1 | 9/2009 |
| WO | 2005118806 A2 | 12/2005 |
| WO | 2007073737 A1 | 7/2007 |
| WO | 2008045505 A2 | 4/2008 |
| WO | 2008153692 A2 | 12/2008 |
| WO | 2009009457 A1 | 1/2009 |
| WO | 2009012468 A2 | 1/2009 |
| WO | 2009015357 A1 | 1/2009 |
| WO | 2009025852 A2 | 2/2009 |
| WO | 2009036236 A1 | 3/2009 |
| WO | 2009070653 A1 | 6/2009 |
| WO | 2009100029 A1 | 8/2009 |
| WO | 2009114681 A2 | 9/2009 |
| WO | 2009120877 A2 | 10/2009 |
| WO | 2009132273 A2 | 10/2009 |
| WO | 2009133915 A1 | 11/2009 |
| WO | 2009143379 A2 | 11/2009 |
| WO | 2009147519 A1 | 12/2009 |
| WO | 2010054386 A2 | 5/2010 |
| WO | 2010117829 A2 | 10/2010 |
| WO | 2011015720 A1 | 2/2011 |
| WO | 2011057003 A2 | 5/2011 |
| WO | 2012145409 A1 | 10/2012 |
| WO | 2014145363 A1 | 10/2012 |
| WO | 2013036936 A1 | 3/2013 |
| WO | 2015073972 A1 | 5/2015 |
| WO | 2015164431 A2 | 10/2015 |
| WO | 2015173112 A1 | 11/2015 |
| WO | 2015184228 A1 | 12/2015 |
| WO | 2016070119 A1 | 5/2016 |
| WO | 2017120285 A1 | 7/2017 |
| WO | 2017161256 A1 | 9/2017 |
| WO | 2017165458 A1 | 9/2017 |

OTHER PUBLICATIONS

Adachi, Taichi, et al., Plasma MicroRNA 499 as a Biornarker of Acute Myocardial Infarction, Clinical Chemistry, vol. 56, No. 7, pp. 1183-1185, 2010.

Albert, MS. et al., "The diagnosis of mild cognitive impairment due to Alzheimer's disease: Recommendations from National institute on Aging-Alzheimer's Association workgroup" Alzheimer's & Dementia (2011) vol. 7, pp. 270-279.

Australia Patent Examination Report No. 1 issued in Australian Patent Application No. 2012245580 dated Aug. 30, 2016, 3 pages.

Australia Patent Examination Report No. 1 issued in Australian Patent Application No, 2012245628 dated Jun. 8, 2016, 6 pages.

Australia Patent Examination Report No. 2 issued in Australian Patent Application No. 2012245580 dated Jun. 2, 2017, 4 pages.

Backes, C. et al., "A dictionary on microRNAs and their putative target pathways" Nucleic Acids Research (2010) vol. 38, pp. 4476-4486.

Bak, M. et al., "MicroRNA expression in the adult mouse central nervous system" RNA, (2008) vol. 14, No. 3, pp. 432-444.

Bartel, D.P., "MicroRNAs: target recognition and regulatory functions" Cell (2009) vol. 136, pp. 215-233.

Bishop, DL. et al., "Axon branch removal at developing synapses by axosome shedding" Neuron (2004) vol. 44, pp. 651-661.

Boeri, M. et al., "MicroRNA Signatures in Tissues and Plasma Predict Development and Prognosis of Computed Tomography Detected Lung Cancer" PNAS (2011) vol. 108, No. 9, pp. 3713-3718.

Braak, H. et al., "Neuropathological staging of Alzheimer's related changes" Acta Neuropathol (1991) vol. 82, pp. 239-259.

Brase, J. C. et al., "Circulating miRNAs are correlated with tumor progression in prostate cancer" International Journal of Cancer (2011) vol. 128, No. 3, pp. 608-616.

Brase, J. C. et al., "Serum microRNAs as non-invasive biomarkers for cancer" Molecular Cancer (2010) vol. 9, pp. 306-315.

Bredesen, D., "mCiRNA—Synaptic Crystal Ball?" Aging (2012) vol. 4, No. 11, pp. 732-733.

(56) References Cited

OTHER PUBLICATIONS

Canadian Communication received for Canadian Patent Application No. 2,780,222, dated Jan. 18, 2018, 5 pages.
Canadian Communication received for Canadian Patent Application No. 2,780,222, dated Nov. 18, 2016, 4 pages.
Canadian Communication received for Canadian Patent Application No. 2,833,375, dated Nov. 24, 2017, 7 pages.
Canadian Communication received for Canadian Patent Application No. 2,833,389, dated Nov. 21, 2017, 4 pages.
Charras, G. T. et al., "Life and times of a cellular bleb" Biophys J. (2008) vol. 94, No. 5, pp. 1836-1853.
Chen, X., "Characterization of microRNAs in serum: a novel class of biomarkers for diagnosis of cancer and other diseases" Cell Research (2008) vol. 18, pp. 997-1006.
Chim, S.S.C. et al., "Detection and Characterization of Placental MicroRNAs in Maternal Plasma" Clinical Chemistry (2008) vol. 54, No. 3, pp. 482-490.
Chinese Communication received for Chinese Patent Application No. 201280030048.6, dated Aug. 5, 2014, 13 pages total.
Chinese Office Action dated Aug. 15, 2016, which issued during prosecution of Chinese Application No. 201280030033.X, 8 pages total.
Chinese Office Action dated Aug. 5, 2015, which issued during prosecution of Chinese Application No. 201280030048.6, 16 pages total.
Chinese Office Action dated Jul. 23, 2014, which issued during prosecution of Chinese Application No. 201280030033.X, 12 pages total.
Chinese Office Action dated Jun. 2, 2015, which issued during prosecution of Chinese Application No. 201280030033.X, 12 pages total.
Chinese Office Action dated Mar. 26, 2015, which issued during prosecution of Chinese Application No. 201280030048.6, 16 pages total.
Chinese Office Action dated Nov. 24, 2015, which issued during prosecution of Chinese Application No. 201280030033.X, 10 pages total.
Cogswell, J. P. et al., "Identification of miRNA Changes in Alzheimer's Disease Brain and CSF Yields Putative Biomarkers and Insights into Disease Pathways" Journal of Alzheimer's Disease (2008) vol. 14, pp. 27-41.
Delrieu, J. et al., "Managing Cognitive Dysfunction through the Continuum of Alzheimer's Disease" CNS Drugs (2011) vol. 25, No. 3, pp. 213-226.
Eaton, B.A. et al., "Synapse disassembly" Genes Dev. (2003) vol. 17, pp. 2075-2082.
Edbauer, D. et al., "Regulation of synaptic structure and function by FMRP-associated microRNAs miR-125b and miR-132" Neuron (2010) vol. 65, No. 3, pp. 373-384.
Emery, V., "Alzheimer disease: are we intervening too late?" J Neural Transm. (2011) vol. 118, No. 9, pp. 1361-1378.
European Communication (extended European search report) dated Feb. 27, 2018, which issued during prosecution of European Application No. 17207859.4, 9 pages total.
European Communication dated Nov. 15, 2016, which issued during prosecution of European Application No. 16 185 046.6, 12 pages total.
European Communication (Extended European Search Report) dated Jun. 9, 2017, which issued during prosecution of European Application No. 14862355.6, 9 pages total.
European Communication pursuant to Article 94(3) EPC dated Aug. 21, 2014, which issued during prosecution of European Application No. 10 779 376.2, 6 pages total.
European Communication pursuant to Article 94(3) EPC dated Dec. 8, 2016, which issued during prosecution of European Application No. 12 773 705.4, 4 pages total.
European Communication pursuant to Article 94(3) EPC dated Jan. 5, 2016, which issued during prosecution of European Application No. 12 773 705.4, 6 pages total.
European Communication pursuant to Article 94(3) EPC dated Jun. 25, 2015, which issued during prosecution of European Application No. 12 774 179.1, 4 pages total.
European Communication pursuant to Article 94(3) EPC dated May 24, 2013, which issued during prosecution of European Application No. 10 779 376.2, 11 pages total.
European Communication pursuant to Article 94(3) EPC dated Nov. 6, 2015, which issued during prosecution of European Application No. 10 779 376.2, 7 pages total.
European Communication pursuant to Article 94(3) EPC received for European Patent Application No. 14862355.6, dated Mar. 20, 2018, 5 pages.
European Communication pursuant to Rules 161(2) and 162 EPC dated Nov. 26, 2013, which issued during prosecution of European Application No. 12 774 179.1, 3 pages total.
European Communication pursuant to Rules 70(2) and 70a(2) EPC received for European Application No. 12 774 179.1, dated Nov. 18, 2014, 1 page.
European Communication received for European Patent Application No. 12773705.4, dated Sep. 16, 2014, 6 pages.
European Extended Search Report issued in European Application No. EP16 192 259.6; dated Jan. 24, 2017, 8 pages.
European Search Report dated Jan. 26, 2015, which issued during prosecution of European Application No. 12 773 705.4, 12 pages total.
European Search Report dated Oct. 30, 2014, which issued during prosecution of European Application No. 12 774 179.1, 7 pages total.
Fackler, O.T., et al., "Cell motility through plasma membrane blebbing" J Cell Biol. (2008) vol. 181, No. 6, pp. 879-884.
Lugli, G. et al., "File S2. Entire list of measured human, rat and mouse microRNAs by microarray after filtering and normalization" Journal of Neurochemistry (2008) vol. 106.
Maes, O. C. et al. "Methodology for Discovery of Alzheimer 's Disease Blood-Based Biomarkers" J Gerontol A Biol Sci Med Sci. (2009) vol. 64A, pp. 636-645.
Maes, O. C. et al,, "MicroRNA: implications for Alzheimer Disease and other Human CNS Disorders" Current Genomics (2009) vol. 10, pp. 154-168.
Mapstone, M. et al., "Plasma phospholipids identify antecedent memory impairment in older adults" Nature Medicine (2013) vol. 20, No. 4, pp. 415-418.
Mature Sequence hsa-miR-127-3p, Available online at: <http://www.mirbase.org/cgi-bin/mature.pl?mature_acc=MIMAT0000446>, 1 page.
McDonald, J.S. et al., "Analysis of circulating microRNA: pre analytical and analytical challenges" Clin Chem. (2011) vol. 57, pp. 833-840.
McKhann, GM et al., "The diagnosis of dementia due to Alzheimer's disease: Recommendations from National Institute on Aging-Alzheimer's Association workgroups on diagnostic guidelines for Alzheimer's disease" Alzheimer's Dement. (2011) vol. 7, pp. 263-269.
Mestdagh, P. et al.,"High-throughput Stem-loop RT-qPCR miRNA Expression Profiling Using Minute Amounts of Input RNA" Nucleic Acids Research (2008) vol. 36, No. 21, 8 pages.
Meyer, S.U. et al., "Normalization Strategies for MircoRNA Profiling Experiments: A 'Normal' Way to a Hidden Layer of Complexity?" Biotechnol. Lett. (2010) vol. 32, pp. 1777-1788.
Miller, G., "Alzheimer's biomarker initiative hits its stride" Science (2009) vol. 326, pp. 386-389.
MirVana Paris Kit Instructions Ambion, Life Technologies (2011) 36 pages total.
Mitchell, PS. et al., "Circulating microRNAs as stable blood-based markers for cancer detection" Proc Natl Aced Sci USA (2008) vol. 105, pp. 10513-10518.
Miyachi, M. et al. "Circulating muscle-specific microRNA, miR-206, as a potential diagnostic marker for rhabdomyosarcoma" Biochem, Biophys. Res. Commun. (2010), vol. 400, pp. 89-93.
Murayama, S. et al., "The Pathology of Alzheimer's Disease" Clinician (2006) No. 553, pp. 15-19.
Natera-Naranjo, 0. et al., "Identification and quantitative analyses of microRNAs located in the distal axons of sympathetic neurons" RNA (2010) vol. 16, pp. 1516-1529.

(56) References Cited

OTHER PUBLICATIONS

Non-Final Office Action received for U.S. Appl. No. 13/508,262, dated Mar. 7, 2013, 12 pages.
Non-Final Office Action received for U.S. Appl. No. 14/112,684, dated Jul. 9, 2015, 23 pages.
Non-Final Office Action received for U.S. Appl. No. 14/112,765, dated Apr. 28, 2015, 15 pages.
Non-Final Office Action received for U.S. Appl. No. 15/037,559, dated Jul. 27, 2017, 14 pages.
Non-Final Office Action received for U.S. Appl. No. 15/390,110, dated Jan. 31, 2018, 46 pages.
Non-Final Office Action received for U.S. Appl. No. 15/606,747, dated Jun. 1, 2018, 60 pages.
Olsen, L. et al., "MicroRNAs Show Mutually Exclusive Expression Patterns in the Brain of Adult Male Rats" PLoS ONE (2009) vol. 4, No. 10, e7225.
Peltier, HJ. et al., "Normalization of microRNA expression levels in quantitative RT-PCR assays: identification of suitable reference RNA targets in normal and cancerous human solid tissues" RNA (2008) vol. 14, pp. 844-852.
Petersen, R.C. et al., "Prevalence of Mild Cognitive Impairment is Higher in Men" The Mayo Clinic Study of Aging, Neurology (2010) vol. 75, pp. 889-897.
Pogue, A.I. et al., "Micro RNA-125b (miRNA-125b) Function in Astrogliosis and Glial Cell Proliferation" Neuroscience Letters (2010) vol. 476, pp. 18-22.
Ray, S. et al., "Classification and prediction of clinical Alzheimer's diagnosis based on plasma signaling proteins" Nat Med. (2007) vol. 13, pp. 1359-1362.
Satoh, J-i., "Molecular network of microRNA targets in Alzheimer's disease brains" Exp Neurol. (2012) vol. 235, pp. 436-446, ePub Sep. 16, 2011.
Satoh, J-i., "MicroRNAs and Their Therapeutic Potential for Human Diseases: Aberrant MicroRNA Expression in Alzheimer's Disease Brain" J Pharmacol Sci. (2010) vol. 114, pp. 269-275.
Schipper, H.M. et al., "MicroRNA expression in Alzheimer blood mononuclear cells" Gene Regul. Syst. Bio. (2007) vol. 1, pp. 263-274.
Schmand, B. et al., "Value of Neurophysiological Tests, Neuroimaging, and Biomarkers for Diagnosing Alzheimer's Disease in Younger and Older Age Cohorts" J Am Geriatr Soc. (2001) vol. 59, pp. 1705-1710.
Schratt, G. M. et al., "A brain-specific microRNA regulates dendritic spine development" Nature (2006) vol. 439, pp. 283-289.
Schratt, G., "microRNAs at the synapse" Nature Reviews Neuroscience (2009) vol. 10, pp. 842-849.
Sempere, L. F, et al., "Expression profiling of mammalian microRNAs uncovers a subset of brain-expressed microRNAs with possible roles in murine and human neuronal differentiation" Genome Biology (2004) vol. 5, No. R13, pp. R13.1-R13.11.
Sheinerman, K.S. et al., "Plasma microRNA biomarkers for detection of mild cognitive impairment" Aging (2012) vol. 4, No. 9, pp. 590-605.
Sheinerman, K.S. et al., "Analysis of organ-enriched micro-RNAs in plasma as an approach to development of Universal Screening Test: feasibility study" Journal of Translational Medicine (2013) vol. 11, No. 304.
Sheinerman, K.S. et al., "Circulating cell-free microRNA as biomarkers for screening, diagnosis, and monitoring of neurode-generative diseases and other neurologic pathologies" Front.Cell.Neurosci. (2013) vol. 7, Art. 150, pp. 1-10.
Sheinerman, K.S. et al., "Early detection of neurodegenerative diseases" Cell Cycle (2013) vol. 12, No. 1.
Sheinerman, K.S. et al., "Plasma microRNA biomarkers for detection of mild cognitive impairment: biomarker validation study" Aging (2013) vol. 5, No. 12, pp. 925-938.
Sheinerman, K.S. et al., Universal screening test based on analysis of circulating organ-enriched microRNAs: a novel approach to diagnostic screening, Expert Rev. Mol. Diagn, (2015) vol. 15, No. 3, pp. 329-338.
Shingara, J. et al. "An optimized isolation and labeling platform for accurate microRNA expression profiling" RNA (2005) vol. 11, pp. 1461-1470.
Skog, J, et al., "Glioblastoma microvesicles transport RNA and proteins that promote tumour growth and provide diagnostic biomarkers" Nat Cell Biol. (2008) vol. 10, No. 12, pp. 1470-1476.
Sperling, R.A. et al., "Toward Defining the Preclinical Stages of Alzheimer's Disease: Recommendations from the National institute on Aging and the Alzheimer's Association Workgroup" Alzheimer's & Dementia (2011) pp. 1-13.
Sperling, R.A., et al., "The diagnosis of dementia due to Alzheimer's disease: Recommendations from National Institute on Aging—Alzheimer's Association workgroups on diagnostic guidelines for Alzheimer's disease" Alzheimer's Dement. (2011) vol. 7, pp. 280-292.
Supplementary Figures and Tables from Peltier et al. (RNA (2008), 14-844-852) (the balance of the article is of record as citation C47 in the IDS of Oct. 18, 2013).
Veerla, S. et al. "MiRNA expression in urothelial carcinomas: important roles of miR-10a, miR-222, miR-125b, miR-7 and miR452 for lung stage and metastasis, and frequent homozygous losses of miR-31" International Journal of Cancer (2009), vol. 124, pp. 2236-2242.
Vlaminck, I. et al., "Circulating Cell-Free DNA Enables Noninvasive Diagnosis of Heart Transplant Rejection" Science Translational Medicine (2014) vol. 6, No. 241, pp. 1-19.
Wang, G-K. et al,, "Circulating microRNA: a novel potential biomarker for early diagnosis of acute myocardial infarction in humans" European Heart Journal (2010) vol. 31, Issue 6, pp. 659-666.
Wang, K. et al., "Circulating microRNAs, potential biomarkers for drug-induced liver injury" Proc Natl Acad Sci USA (2009) vol. 106, No. 11, pp. 4402-4407.
Wang, W-X, et al., "The Expression of MicroRNA miR-107 Decreases Early in Alzheimer's Disease and May Accelerate Disease Progression through Regulation of β-Site Amyloid Precursor Protein-Cleaving Enzyme 1" The Journal of Neuroscience (2008) vol. 28, pp. 1213-1223.
Wang, X., "A PCR-based Platform for microRNA Expression Profiling Studies" RNA (2009) vol. 15, pp. 716-723.
Final Office Action received for U.S. Appl. No. 13/508,262, dated Jul. 30, 2013, 10 pages.
Final Office Action received for U.S. Appl. No. 14/112,684, dated Apr. 28, 2016, 19 pages.
Final Office Action received for U.S. Appl. No. 14/112,765, dated Oct. 9, 2015, 18 pages.
Final Office Action received for U.S. Appl. No. 15/037,559, dated Apr. 18, 2018, 26 pages.
Geekiyanage, H. et al., "Blood serum miRNA: Non-invasive biomarkers for Alzheimer's disease" Exp Neurol. (2011) vol. 235, pp. 491-496, ePub Dec. 1, 2011.
Gene Cards entry for MIR146A, retrieved from https://www.genecards.org/cgi-bin/carddisp.pl?gene=MIR146A&Keywords=mir146 on Apr. 14, 2018, 11 pages total.
Gillardon, F. et al. "MicroRNA and proteome expression profiling in early-symptomatic α-synuclein(A30P)-transgenic mice" Proteomics Clinical Application (2008) vol. 2, No. 5, pp. 697-705.
Goetz, C.G. "The History of Parkinson's Disease: Early Clinical Descriptions and Neurological Therapies" Cold Spring Harbor Perspect med (2011) vol. 1, a008862.
Griffiths-Jones, S. et al., "miRBase: microRNA sequences, targets and gene nomenclature" Nucleic Acids Research (2006) vol. 34, Database issue: D140-D144.
Hebert, S.S. et al. "Alterations of the microRNA network cause neurodegenerative disease" Trends in Neurosciences (2009) vol. 32, No. 4, pp. 199-206.
Hebert, S.S. et al., "Loss of microRNA cluster miR-29a/b-1 in sporadic Alzheimer's disease correlates with increased BACEI/beta-secretase expression" Proc Natl Acad Sci USA (2008) vol. 105, pp. 6415-6420.
Henriksen, K. et al., "The future of blood-based biomarkers for Alzheimer's disease" Alzheimer's & Dementia (2014) vol. 10, pp. 115-131.

(56) References Cited

OTHER PUBLICATIONS

Hua, D. et al., "A Catalogue of Glioblastoma and Brain MicroRNAs Identified by Deep Sequencing" OMICS A Journal of Integrative Biology (2012) vol. 16, No. 12, pp. 690-699.
Hua, Y-J. et al., "identification and target prediction of miRNAs specifically expressed in rat neural tissue" BMC Genomics (2009) vol. 10, pp. 214-225.
Hunter, M.P. et al., "Detection of microRNA Expression in Human Peripheral Blood Microvesicles" PLoS ONE (2008) vol. 3, No. 11, e3694.
International Preliminary Report on Patentability for International Appl. No. PCT/US2010/055495, dated May 8, 2012, 14 pages total.
International Preliminary Report on Patentability issued in PCT/US2012/034098 dated Oct. 22, 2013, 15 pages total.
International Preliminary Report on Patentability received for PCT Patent Application No. PCT/US2012/034025, dated Oct. 31, 2013, 9 pages.
International Preliminary Report on Patentability received for PCT Patent Application No. PCT/US2014/065959, dated May 24, 2016, 15 pages.
International Preliminary Report on Patentability received for PCT Patent Application No. PCT/US2017/012258, dated Jul. 10, 2018, 12 pages.
International Search Report and Written Opinion for International Appl. No. PCT/US2010/055495, dated Jun. 6, 2011, 20 pages total.
International Search Report and Written Opinion of the International Searching Authority for International Application No. PCT/US2012/034025, dated Sep. 28, 2012, 14 pages total.
International Search Report and Written Opinion of the International Searching Authority for International Application No. PCT/US2012/034098, dated Jul. 17, 2012, 16 pages total.
International Search Report and Written Opinion of the International Searching Authority dated Apr. 28, 2015 issued during prosecution of International Application No. PCT/US2014/065959, 17 pages total.
International Search Report and Written Opinion of the International Searching Authority dated May 8, 2017 issued during prosecution of International Application No. PCT/US2017/012258, 14 pages total.
International Search Report for International Application No. PCT/US2017/23470, dated Jul. 31, 2017, 24 pages total.
Issler, O. et al., "Determining the Role of MicroRNAs in Psychiatric Disorders" Nature Reviews Neuroscience (2015) vol. 16, pp. 201-212.
Japanese Office Action issued in Japanese Patent Application No. 2014-506501 dated Mar. 16, 2016 (and English-language translation thereof), 15 pages.
Japanese Office Action Issued in Japanese Patent Application No. 2014-506516 dated Apr. 4, 2016 (and English-language translation thereof), 20 pages.
Japanese Office Action issued in Japanese Patent Application No. 2014-506516 dated Mar. 1, 2017, 10 pages total.
Ji, X. et al., "Plasma miR-208 as a Biomarker of Myocardial Injury" Clinical Chemistry (2009) vol. 55, No. 11, pp. 1944-1949.
Kemppainen, et al., "MicroRNAs as biomarkers in blood and other biofluids, poster 2010?" [Retrieved from the Internet Sep. 8, 2012: <http://www.asuragen.comipdfs/postersibiomarkers.pdf>].
Koirala S, et al., "Pruning an Axon Piece by Piece" Neuron (2004) vol. 44, pp. 578-580.
Kosaka, N. et al., "Circulating microRNA in body fluid: a new potential biomarker for cancer diagnosis and prognosis" Cancer Sci. (2010) vol. 101, pp. 2087-2092.
Kosaka, N. et al., "Secretory Mechanisms and Intercellular Transfer of MicroRNAs in Living Cells" J Biol Chem. (2010) vol. 285, No. 23, pp. 17442-17452.
Kroh, E.M et al., "Analysis of Circulating MircoRNA Biomarkers in Plasma and Serum Using Quantitative Reverse Transcription-PCR (qRT-PCR)" Methods (2010) vol. 50, pp. 298-301.

Kye MJ, et al., "Somatodendritic microRNAs identified by laser capture and multiplex RT-PCR" RNA (2007) vol. 13, pp. 1224-1234.
Landgraf, P., "A Mammalian microRNA Expression Atlas Based on Small RNA Library Sequencing" Cell (2007) vol. 129, No. 7, pp. 1401-1414.
Laterza, O.F. et al., "Plasma MicroRNAs as Diagnostically Sensitive and Specific Biomarkers of Tissue Injury" Clinical Chemistry (2009) vol. 55, No. 11, pp. 1-7.
Lee, EJ. et al., "Systematic evaluation of microRNA processing patterns in tissues, cell lines, and tumors" RNA (2008) vol. 14, pp. 35-42.
Liang, Y, et al., "Characterization of microRNA expression profiles in normal human tissues" BMC Genomics (2007) vol. 8, pp. 166-185.
Liang, Y. "An expression meta-analysis of predicated microRNA targets identifies a diagnostic signature for lung cancer" BMC Med. Genomics (2008) vol. 1, No. 61, pp. 1-16.
Lin, A-L. et al., "Multimodal MRI Neuroimaging Biomarkers for Cognitive Normal Adults, Amnestic Mild Cognitive Impairment, and Alzheimer's Disease" Neurology Research International vol. 2012, Article ID 907409, 17 pages.
Lindner, K. et al. "Circulating microRNAs: emerging biomarkers for diagnosis and prognosis in patients with gastrointestinal cancers" Clinical Science (2015) vol. 128, pp. 1-15.
Liu, D-Z. et al., "Brain and blood microRNA expression profiling of ischemic stroke, intracerebral hemorrhage, and kainate seizures" J Cereb Blood Flow Metab., advance online publication (2009) doi:10.1038/jcbfm.2009, vol. 186, pp. 1-10.
Liu, R. et al., "A Five-microRNA Signature Identified from Genome-wide Serum microRNA Expression Profiling Serves as a Fingerprint for Gastric Cancer Diagnosis" European Journal of Cancer (2011) vol. 47, pp. 784-791.
Lodes, M. J. et al., "Detection of Cancer with Serum miRNAs on an Oligonucleotide Microarray" PLoS ONE (2009) vol. 4, No. 7, e6229.
Londin, E. et al., "Analysis of 13 cell types reveals evidence for the expression of numerous novel primate- and tissue-specific microRNAs" Proc. Natl. Acad. Sci. USA (2015) E1106-E1115.
Low, LK et al., "Axon pruning: an essential step underlying the developmental plasticity of neuronal connections" Phil Trans R Soc B. (2006) vol. 361, pp. 1531-1544.
Lugli, G. et al., "Expression of microRNAs and their precursors in synaptic fractions of adult mouse forebrain" Journal of Neurochemistry (2008) vol. 106, pp. 650-661.
Abdel-Salam, O.M.E. et al., "Drugs Used to Treat Parkinson's Disease, Present Status and Future Directions" CNS & Neurological Disorders—Drug Targets (2008) vol. 7, pp. 321-342.
Canadian Communication received for Canadian Patent Application No. 2,833,375, dated Dec. 9, 2019, 5 pages.
Canadian Communication received for Canadian Patent Application No. 2,833,389, dated Nov. 22, 2019, 4 pages total.
Chinese Office Action dated Sep. 20, 2019, which issued during prosecution of Chinese Application No. 201480073413.0, 15 pages total.
Cloutier, F. et al., "MicroRNAs as Potential Circulating Biomarkers for Amyotrophic Lateral Sclerosis" Journal of Molecular Neuroscience (2014) vol. 56, No. 1, pp. 102-112.
European Communication (Extended European Search Report) received for European Application No. 17771018.3, dated Sep. 20, 2019, 9 pages total.
Gazewood, J.D. et al., "Parkinson Disease: An Update" American Family Physician (2013) vol. 87, No. 4, 7 pages total.
Japanese Office Action dated Aug. 13, 2019, which issued during prosecution of Japanese Application No. 2016-532043, 10 pages total.
Kansara, S. et al., "Early Diagnosis and Therapy of Parkinson's Disease: Can Disease Progression be Curbed?" J. Neural Transm. (2013) vol. 120, pp. 197-210.
Non-Final Office Action received for U.S. Appl. No. 15/037,559, dated Jun. 25, 2019, 34 pages.
Restriction Requirement received for U.S. Appl. No. 16/044,279, dated Oct. 8, 2019, 12 pages total.

(56) References Cited

OTHER PUBLICATIONS

Chinese Office Action dated Mar. 26, 2019, which issued during prosecution of Chinese Application No. 201480073413.0, 8 pages total.
Chinese Office Action dated Mar. 25, 2019, which issued during prosecution of Chinese Application No. 201610344816.5, 13 pages total.
Communication (International Preliminary Report on Patentability) issued by the International Searching Authority in International Patent Application No. PCT/US2017/023470 dated Sep. 25, 20 pages total.
Communication (Written Opinion) issued by the International Searching Authority in International Patent Application No. PCT/US2017/023470 dated Jul. 31, 2017, 19 pages total.
Canadian Communication received for Canadian Patent Application No. 2,780,222 dated Jan. 28, 2019, 5 pages total.
Canadian Communication received for Canadian Patent Application No. 2,833,375, dated Oct. 12, 2018, 7 pages total.
Canadian Communication received for Canadian Patent Application No. 2,833,389, dated Oct. 18, 2018, 3 pages total.
European Communication (Article 94(3) EPC) received for European Application No. 14862355.6, dated Jan. 22, 2019, 8 pages total.
Japanese Communication (First Office Action) received for Japanese Patent Application No. 2017-174778, dated Nov. 16, 2018, 21 pages total.
Japanese Communication received for Japanese Patent Application No. 2016-532043, dated Oct. 2, 2018, 17 pages total.
Sheinerman, K.S. et al., "Circulating Brain-Enriched MicroRNAs as Novel Biomarkers for Detection and Differentiation of Neurodegenerative Diseases" Alzheimer's Research & Therapy (2017) vol. 9, No. 89, 13 pages total.
Final Office Action received for U.S. Appl. No. 15/606,747, dated Dec. 26, 2018, 40 pages.
Non-Final Office Action received for U.S. Appl. No. 15/390,110, dated Sep. 25, 2018, 30 pages.
Communication issued by the International Searching Authority in International Application No. PCT/US17/064379 dated May 8, 2018, 7 pages total (International Search Report).
Communication issued by the International Searching Authority in International Application No. PCT/US17/064379 dated May 8, 2018, 8 pages total (Written Opinion).
Weber, J.A. et al., "The microRNA spectrum in 12 body fluids" Clin. Chem. (2010) vol. 56, pp. 1733-1741.
Wu, Q. et al., "Next-Generation Sequencing of MicroRNAs for Breast Cancer Detection" Journal of Biomedicine and Biotechnology (2011) vol. 2011, Article ID 597145, 7 pages total.
Xu, S. et al. "MicroRNA (miRNA) transcriptome of mouse retina and identification of a sensory organ-specific miRNA cluster" Journal of Biological Chemistry (2007) vol. 282, pp. 25053-25066.
Yoo, M.S. et al., "Oxidative Stress Regulated Genes in Nigral Dopaminergic Neuronal Cells: Correlation with the Known Pathology in Parkinson's Disease" Molecular Brain Research (2003) vol. 110, pp. 76-84.
Yoshiyama, Y. et al., "Synapse Loss and Microglial Activation Precede Tangles in P301S Tauopathy Mouse Model" Neuron. (2007) vol. 53, pp. 337-351.

Zampetaki, A. et al., "Plasma microRNA Profiling Reveals Loss of Endothelial MiR-126 and Other microRNAs in Type 2 Diabetes" Circulation Research (2010) vol. 107, pp. 810-817.
Zhao, H. et al., "A Pilot Study of Circulating miRNAs as Potential Biomarkers of Early Stage Breast Cancer" PLoS ONE (2010) vol. 5, No. 10, 12 pages total.
Non-Final Office Action received for U.S. Appl. No. 16/044,279, dated Feb. 14, 2020, 61 pages total.
Osmanovic-Barilar, J. et al., "Evaluating the Role of Hormone Therapy in Postmenopausal Women with Alzheimer's Disease" Drugs Aging (2016) vol. 33, pp. 878-808.
Harman, D., "Alzheimer's Disease: Role of Aging in Pathogenesis" Annals New York Academy of Sciences (2002) vol. 959, pp. 384-395.
Stem-loop Sequence has-mir-335 Accession No. MI0000816, Available online at: <http://www.mirbase.org/cgi-bin/mirna_entry.pl?acc=MI0000291>, 4 pages total.
Stem-loop Sequence has-mir-491 Accession No. MI0003126, Available online at: <http://www.mirbase.org/cgi-bin/mirna_entry.pl?acc=MI0003126>, 3 pages total.
Schymick, J. C. et al., "Expanding the Genetics of Amyotrophic Lateral Sclerosis and Frontotemporal Dementia" Alzheimer's Research & Therapy (2012) vol. 4, No. 30, 6 pages total.
Alzforum: Networking for a Cure, "Genetics Tie ALS into the Frontotemporal Dementia Spectrum" (2018) Available online at: <https://www.alzforum.org/news/research-news/genetics-tie-als-frontotemporal-dementia-spectrum>, 5 pages total.
Restriction Requirement received for U.S. Appl. No. 16/086,881, dated Jan. 15, 2020, 8 pages total.
Ashrafi, A. et al., "Leukocyte Telomere Length is Unrelated to Cognitive Performance Among Non-Demented and Demented Persons: An Examination of Long Life Family Study Participants" Journal of International Neuropsychological Society (2020) 12 pages total.
Hegaard, N.H.H. et al., "Circulating Micro-RNA Expression Profiles in Early Stage Nonsmall Cell Lung Cancer" International Journal of Cancer (2012) vol. 130, pp. 1378-1386.
Coleman, R.A., "Of Mouse and Man—What is the Value of the Mouse in Predicting Gene Expression in Humans?" Drug Discovery Today (2003) vol. 8, No. 6, pp. 233-235.
Liu, Z. et al., "Comparison of Differentually Expressed Genes in T Lymphocytes Between Human Autoimmune Disease and Murine Models of Autoimmune Disease" Clinical Immunology (2004) vol. 112, pp. 225-230.
Non-Final Office Action received for U.S. Appl. No. 16/086,881, dated Jun. 9, 2020, 34 pages total.
Canadian Communication received for Canadian Patent Application No. 2,780,222, dated May 21, 2020, 6 pages total.
Japanese Communication received for Japanese Patent Application No. 2016-532043, dated May 28, 2020, 15 pages total.
Chinese Office Action dated Jul. 3, 2020, which issued during prosecution of Chinese Application No. 201610344816.5, 10 pages total.
Final Office Action received for U.S. Appl. No. 15/037,559, dated Feb. 27, 2020, 17 pages.

* cited by examiner

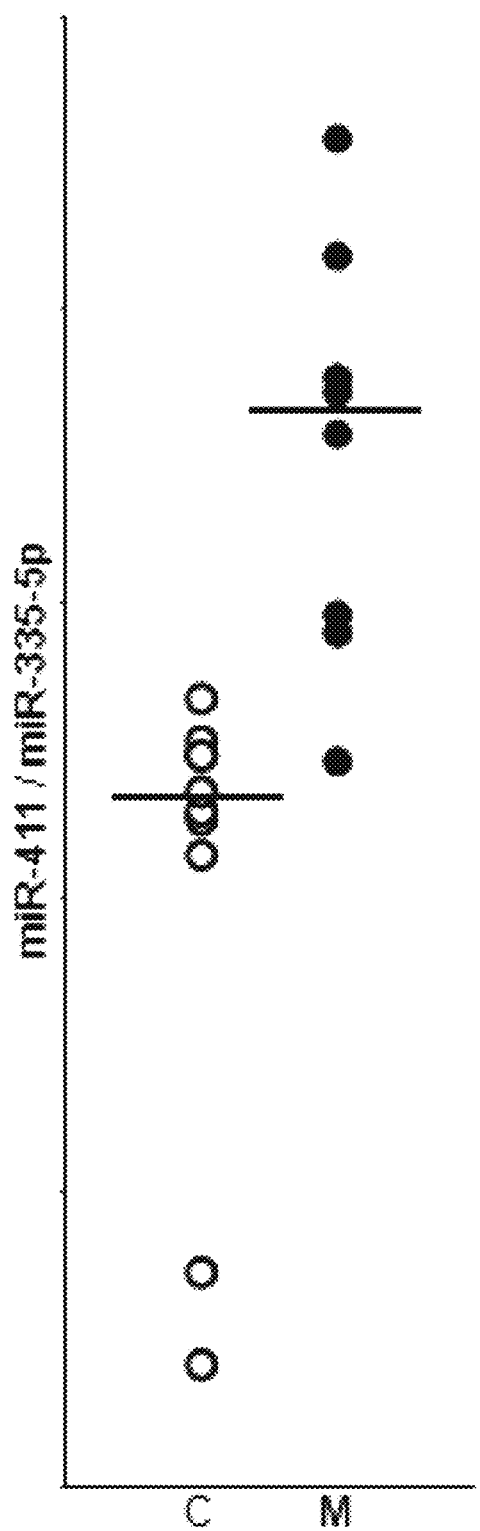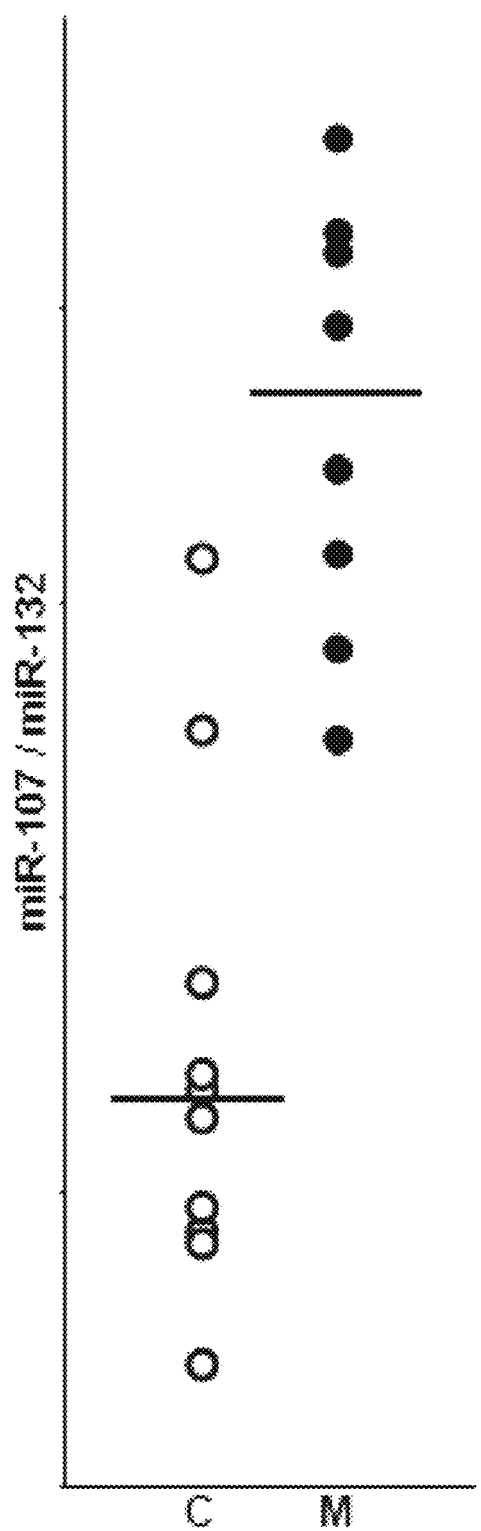
*FIG. 4A*     *FIG. 4B*

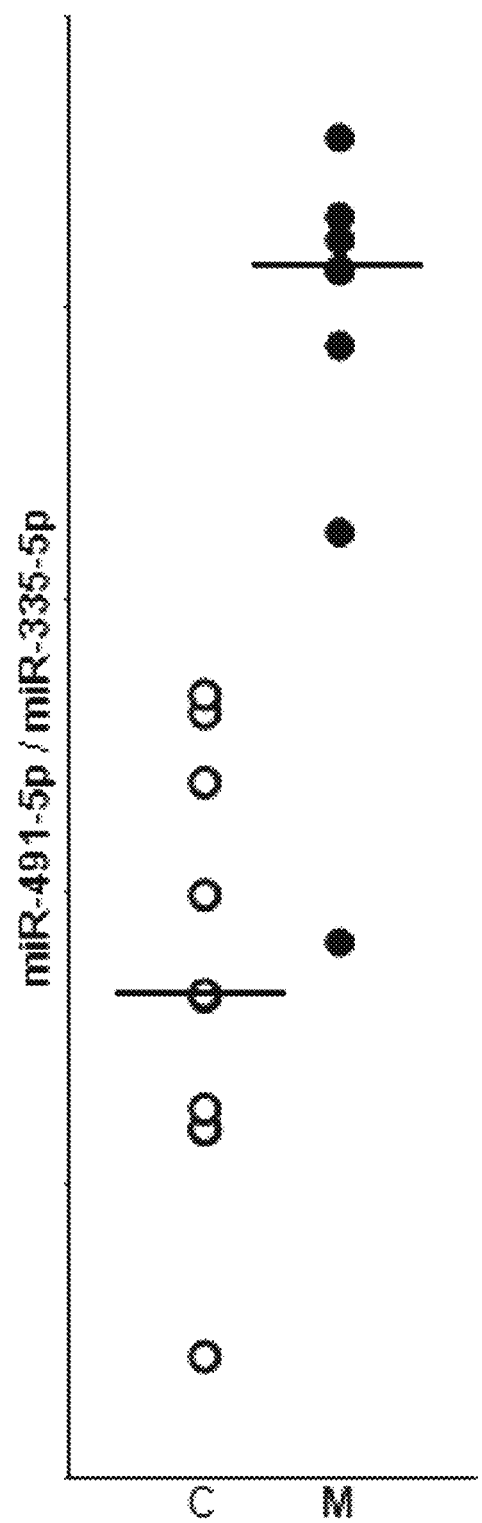
*FIG. 4C*  *FIG. 4D*

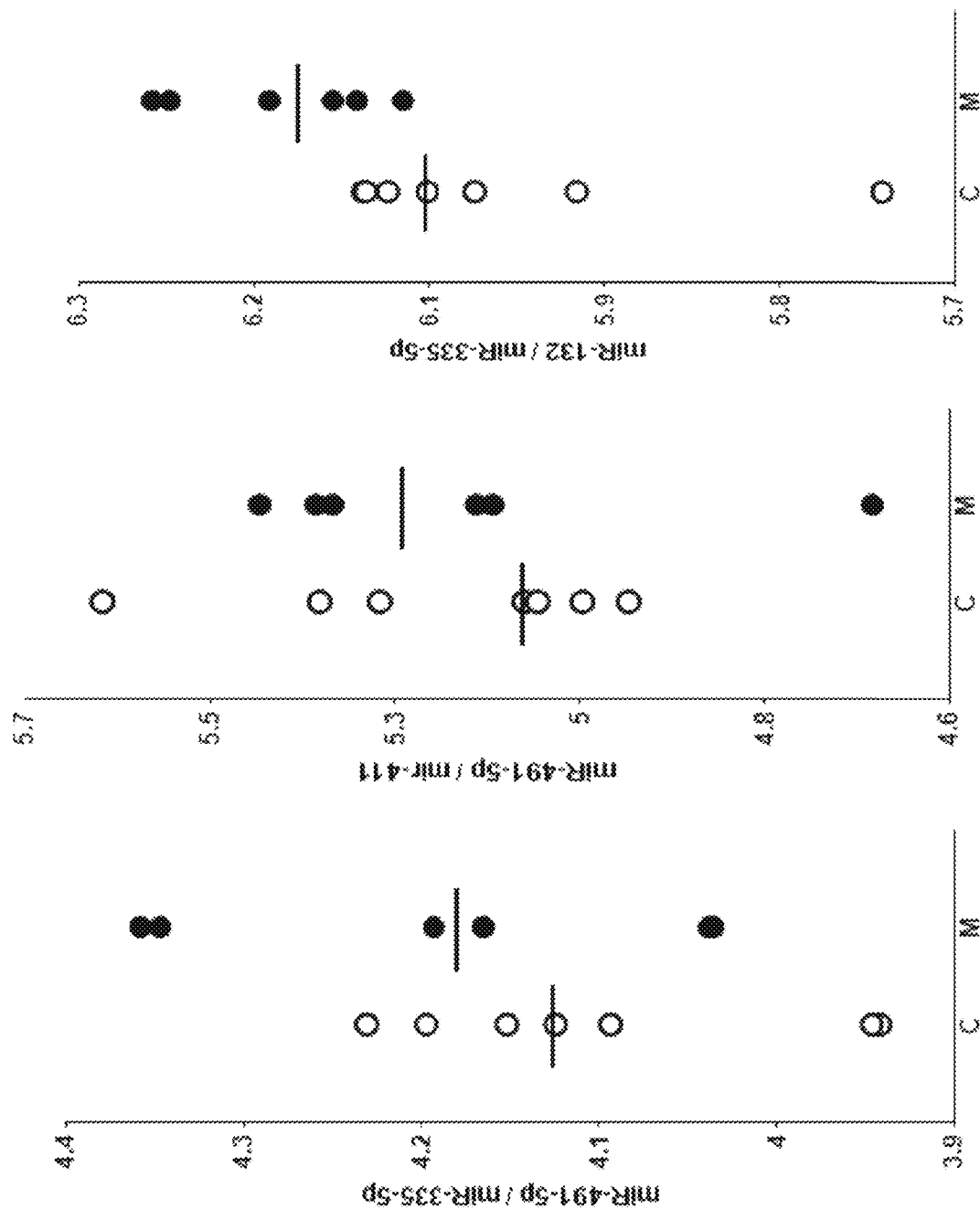

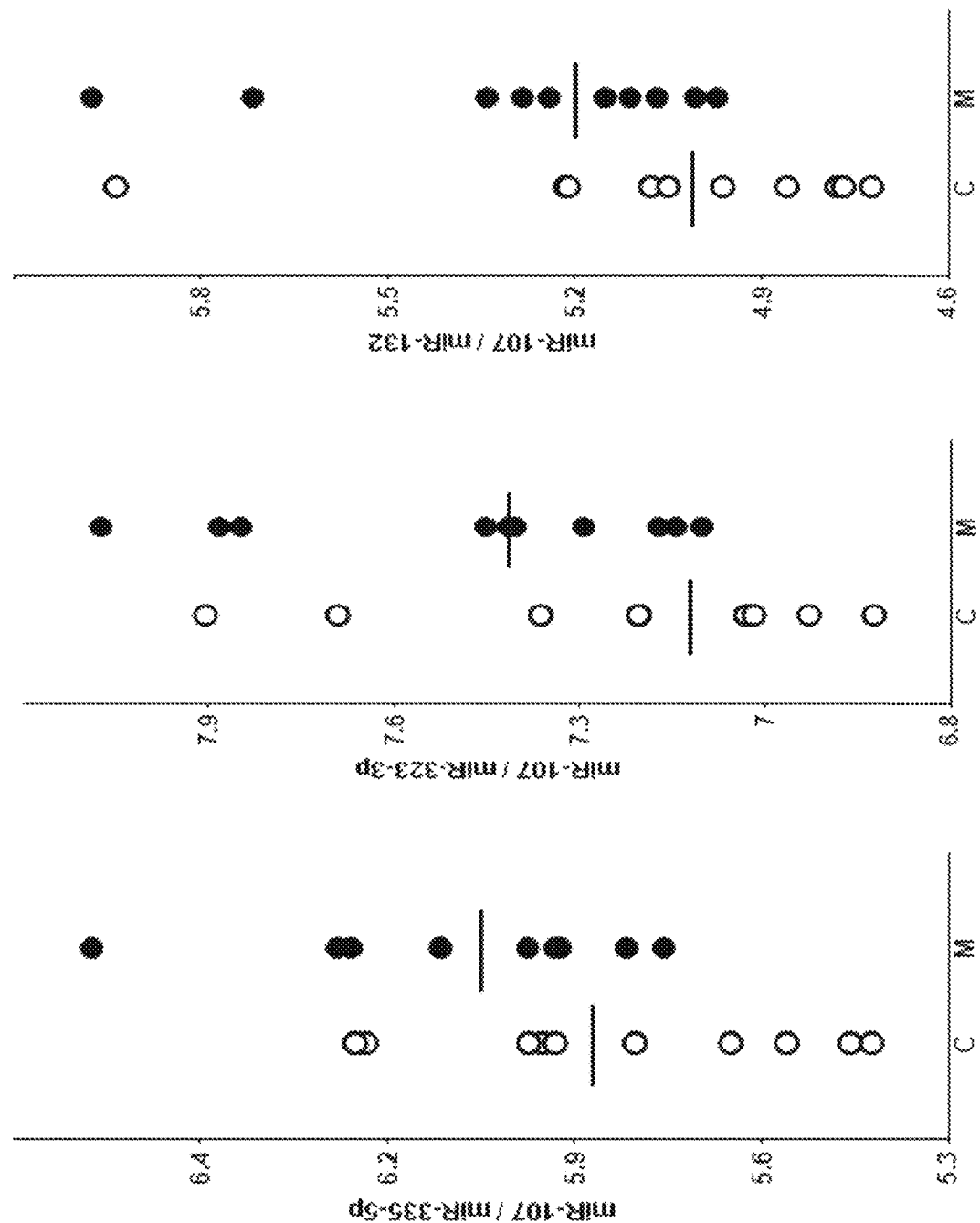

METHODS OF USING MIRNA FROM BODILY FLUIDS FOR DIAGNOSIS AND MONITORING OF NEURODEVELOPMENTAL DISORDERS

CROSS REFERENCE TO RELATED APPLICATIONS

The present application claims priority to U.S. Provisional Patent Application No. 62/529,372, filed on Jul. 6, 2017 and is also a continuation-in-part of International Patent Application No. PCT/US2017/012258, filed on Jan. 5, 2017, which claims priority to U.S. Provisional Patent Application No. 62/274,999, filed on Jan. 5, 2016, and U.S. Provisional Patent Application No. 62/396,577, filed on Sep. 19, 2016, all of which applications are hereby incorporated by reference in their entirety.

TECHNICAL FIELD OF THE INVENTION

The invention provides methods for diagnosis and monitoring of Rett syndrome and other neurodevelopmental disorders by quantitative analysis of miRNAs in bodily fluids.

BACKGROUND OF THE INVENTION

Neurodevelopmental disorders (NDDs) include pathologies caused by disturbances of the nervous system development. Some of NDDs, such as Rett syndrome, Tourette syndrome and others are rare, but some, for example Autism Spectrum Disorders, are much more common. Early minimally invasive tests for early detection of NDDs are very important for the following reasons. First, although there is no effective treatment for most of NDDs, early symptomatic treatment may significantly improve patient health. Second, due to variability of mutations causing particular NDDs and other factors these disorders are characterized by the wide phenotypical and clinical heterogeneity, and biomarkers capable of predicting disease development and outcome would be very useful. Finally and maybe most importantly, such biomarkers would be extremely helpful on all stages of drug/treatment development, including use of animal models in preclinical studies, patient involvement and stratification for clinical studies and treatment monitoring.

Rett syndrome (RTT) is a monogenic X-linked disorder caused by mutations in MECP2 gene, which encodes the methyl-CpG binding protein 2 (Renieri A et al. Rett syndrome: the complex nature of a monogenic disease. J Mol Med (Berl). 2003; 81(6):346-54). Due to severe encephalopathy caused by a mutation in the single copy of MECP2 male fetuses usually die before birth, so the disease affects females almost exclusively (~1 in 10,000).

In addition to brain pathology, other organs (e.g., liver, muscle) and metabolic processes (e.g. cholesterol metabolism) are involved in RTT development (Amir, R. E., et al. Rett syndrome is caused by mutations in X-linked MECP2, encoding methyl-CpG-binding protein. Nat Genet., 23, 185-188 (1999); Armstrong D D. Rett syndrome neuropathology review 2000. Brain Dev. 23 Suppl 1, S72-76 (2001); Lyst, M. J., Bird, A. Rett syndrome: a complex disorder with simple roots. Nat. Rev. Genet., 16, 261-275 (2015)).

An advantage of using RTT as an example for developing diagnostic tests for NDDs in general is the existence of several mouse models of RTT (see below). Of course, potential biomarkers should be evolutionary conserved to be applicable for both human and animals.

MicroRNAs (miRNAs) are a class of non-coding RNAs whose final product is an approximately 22 nt functional RNA molecule. They play important roles in the regulation of target genes by binding to complementary regions of messenger transcripts to repress their translation or regulate degradation (Griffiths-Jones Nucleic Acids Research. 2006; 34, Database issue: D140-D144; Jin and Xiao, Frontiers in Genetics. 2015; 6:328). Frequently, one miRNA can target multiple mRNAs and one mRNA can be regulated by multiple miRNAs targeting different regions of the 3'UTR. Once bound to an mRNA, miRNA can modulate gene expression and protein production by affecting, e.g., mRNA translation and stability (Baek et al. Nature. 2008; 455:64; Selbach et al. Nature. 2008; 455:58; Ambros. Nature. 2004; 431: 350-355; Bartel. Cell. 2004; 116: 281-297; Cullen. Virus Research. 2004; 102: 3-9; He et al. Nat. Rev. Genet. 2004; 5: 522-531; and Ying et al. Gene. 2004; 342: 25-28). There are other classes of less characterized small RNAs (reviewed in Kim. Mol. Cells. 2005; 19: 1-15).

Many of miRNAs are specific to or over-expressed in certain organs/tissues/cells (see, e.g., Hua et al. BMC Genomics. 2009; 10:214; Liang et al. BMC Genomics. 2007; 8:166; Landgraf et al. Cell. 2007; 129:1401-1414; Lee et al. RNA. 2008; 14:35-42) and in different brain areas, such as hippocampus, midbrain, frontal cortex, pituitary gland, and in different cell types, such as neurons and glial cells (Sempere et al. Genome Biol. 2004; 5: R13; Deo et al. Dev. Din. 2006; 235:2538-2548; Bak et al. RNA. 2008; 14: 432-444; Trivedi and Ramakrishna Int. J. Neurosci. 2009; 119: 1995-2016; Weng et al. Biomed. Res. 2011; 32: 135-141; He et al. Neuron. 2012; 73: 35-48).

Some miRNAs, including those that are cell-specific, are enriched in certain cellular compartments, particularly in axons, dendrites and synapses (see, e.g., Schratt et al. Nature. 2006; 439:283-289; Lugli et al. J. Neurochem. 2008; 106:650-661; Bicker and Schratt. J. Cell. Mol. Med. 2008; 12:1466-1476; Smalheiser and Lugli. Neuromolecular Med. 2009; 11:133-140; Rajasethupathy. Neuron. 2009; 63:714-716; Kye. RNA. 2007; 13:1224-1234; Yu et al. Exp Cell Res. 2008; 314:2618-2633; Cougot et al. J. Neurosci. 2008; 28:13793-13804; Kawahara. Brain Nerve. 2008. 60:1437-1444; Schratt G. Rev Neurosci. 2009; 10:842-849; Pichardo-Casas et al. Brain Research. 2012; 1436:20-33).

Expression and concentrations of miRNAs are regulated by various physiological and pathological signals. Changes in expression of some miRNAs were found in neurons of Parkinson's, Alzheimer's and other neurodegenerative disease patients (Hebert and De Strooper. Trends Neurosci. 2009; 32:199-206; Saba et al. PLoS One. 2008; 3:e3652; Kocerha et al. Neuromolecular Med. 2009; 11:162-172; Sethi and Lukiw. Neurosci Lett. 2009; 459:100-104; Zeng; Mol Pharmacol. 2009; 75:259-264; Cogswell et al. Journal of Alzheimer's disease. 2008; 14: 27-41; Schaefer et al. J. Exp. Med. 2007; 204:1553-1558; Hebert. Proc. Natl. Acad. Sci. USA. 2008; 105:6415-6420; Wang et. al.. J. Neurosci. 2008; 28:1213-1223; Nelson et al. Brain Pathol. 2008; 18:130-138; Lukiw. Neuroreport. 2007; 18:297-300) as well as in subjects with NDDs (Im, Kenny. Trends Neurosci. 2012; 35:325-334; Sun, Shi. Exp. Neurol. 2015; 268: 46-53).

For the use of miRNA in diagnostics, it is also important that miRNA secretion varies depending on cellular physiology (Palma et al. Nucleic Acids Res. 2012; 40:9125-9138; Pigati et al. PLoS One. 2010; 5: e13515). In addition to miRNA release into extracellular space and subsequent appearance in the bodily fluids due to cell death, miRNA appear in circulation due to blebbing of apoptotic bodies, budding and shedding of microvesicles, active secretion in the form of exosomes and of miRNA complexes with proteins (AGO2, NPM1 and others) and high density lipoproteins (HDL) (reviews: Sun et al. Clin. Chem. Lab. Med. 2012; 50: 2121-2126; Zandberga et al. Genes Chromosomes Cancer. 2013; 52: 356-369). All these forms of cell-free miRNA are highly stable in the bloodstream and other bodily fluids. The secretion of miRNA is selective and can be significantly changed by various pathological processes. For example, changes in the spectrum of miRNA secreted in exosomes from prion-infected neuronal cells, as compared to uninfected cells, have been demonstrated (Belingham et al. Nucleic Acids Res. 2012; 40: 10937-10949).

Two approaches are widely used for searching miRNA biomarkers of various diseases in bodily fluids:

1. The first approach involves measurement of hundreds of different miRNA in a bodily fluid from patients with a pathology of interest and from control subjects using miRNA array or next generation sequencing (NGS) (Qin et al. Cancer Inform. 2013; 12: 83-101). While this approach allows to analyze a huge numbers of various miRNA, currently the miRNA array-based and sequencing techniques are not sufficiently sensitive to detect many miRNA whose concentration in bodily fluids is relatively low. As a consequence, most of the miRNA detectable in bodily fluids by arrays and NGS are ubiquitous miRNA expressed in all or many tissues, and many of them derive from blood cells (Pritchard et al. Cancer Prev. Res. (Phila). 2012; 5:492-497; Leidner and Thompson. PLoS One. 2013; 8: 57841). The detection of changes in the concentrations of such ubiquitous miRNA in patients with one pathology does not mean that the same miRNA cannot be involved in other diseases of different organs. Many miRNA are associated with a particular pathology type, such as cancer, inflammation, hypoxia, etc., and changes in their concentration in bodily fluids can be associated with diseases of different organs. For example, changes of miR-155 concentrations were found in the bloodstream of patients with breast, esophageal, lung, pancreatic cancers and lymphomas (Blair and Yan. DNA Cell Biol. 2012; 31 Suppl. 1: S49-61; Xie et al. Bioinformatics. 2013; 29: 638-644). Level of miR-21 increases in plasma/serum of patients with osteosarcoma, bladder, esophageal, gastric, lung, breast, colorectal cancers, neck squamous cell carcinoma and other tumors (Blair and Yan. DNA Cell Biol. 2012; 31 Suppl. 1: S49-61; Farazi et al. J. Pathol. 2011; 223: 102-115; Xie et al, Bioinformatics. 2013; 29: 638-644). It follows that the potential biomarkers found by miRNA arrays should be also tested in other pathologies, not only in healthy control subjects.

2. The second approach is based on analysis of disease-specific miRNAs identified by comparison of miRNAs isolated from pathologic and normal tissue, organ or cell type. Here, subsequent to identification of disease-specific miRNAs (e.g., by an array followed by RT-PCR), their presence in bodily fluids is analyzed. In this strategy, since a limited number of circulating miRNAs is tested, the use of individual RT-PCR is possible which allows to increase sensitivity and reproducibility of the analysis. However, in many cases when this method was applied, no correlation was detected between miRNA concentration and pathology-induced changes in the tissue and in bodily fluids (Boeri et al., Proc. Natl. Acad. Sci. USA. 2011; 108: 3713-3718; Cuk et al. Int. J. Cancer. 2013; 132: 1602-1612). This phenomenon can be explained by several factors: (i) if pathology is caused by, or associated with, the change in concentration of a ubiquitous miRNA, the effect of the pathology on the concentration of this miRNA in circulation could be very limited, since only a small fraction of the miRNA in circulation comes from the affected organ or tissue; (ii) changes in miRNA concentration due to pathology development can be accompanied by much more prominent opposite changes in miRNA secretion/excretion, which neutralizes or even overcomes the effect of changed miRNA expression.

While miRNAs are much more stable than larger mRNA or rRNA molecules, many factors, including methods of plasma preparation (time between blood collection and plasma freezing, the number of thawing-freezing cycles, centrifugation speed and so on), miRNA extraction methods, and the presence of qRT-PCR inhibitors can affect the miRNA concentrations measured in a given experiment. Further, many biological factors unrelated to the pathology, e.g. changes in blood-brain barrier permeability and blood supply, can affect the miRNA concentrations in plasma.

Two main approaches are commonly used for miRNA data normalization. The most common one involves the use of the least variable miRNA, such as spiked non-human miRNA (Kroh et al., Methods, 2010, 50, 298-301; Sanders et al., Int. J. Urol. 2012. 19, 1017-1025) or ubiquitous miRNA, whose concentration is minimally changed by a pathology being analyzed, or average of all miRNAs, if hundreds of miRNAs are analyzed by a miRNA array. For example, miR-16 and other small RNAs, such as small nuclear or nucleolar RNAs, were widely used in earlier studies. However, the concentrations of some of these miRNAs in bodily fluids were recently shown to be affected by pathologic processes (Lardizabal et al. PLoS One 2012, 7, e36323; Katsuura et al. Neurosci. Lett. 2012, 516, 79-84). The second approach is based on the experimental search for miRNA pairs, which most effectively differentiate two populations, e.g., pathology versus control (Sheinerman et al. Aging 2012, 4, 590-605).

SUMMARY OF THE INVENTION

There is a great need in the art in sensitive methods of early detection of neurodevelopmental disorders such as Rett Syndrome (RTT). The present invention addresses this and other needs by providing methods for early diagnosis, progression and treatment monitoring of neurodevelopmental disorders such as RTT by quantifying miRNAs in bodily fluids.

In one aspect, the invention provides a method for detecting a neurodevelopmental disorder in a subject, which method comprises:

a) measuring the level of a first miRNA in a bodily fluid sample collected from the subject, wherein said first miRNA is enriched in an organ or an organ area(s) affected by the neurodevelopmental disorder;

b) measuring the level of a second miRNA in the same bodily fluid sample collected from the subject;

c) calculating the ratio of the levels of the miRNAs measured in steps (a) and (b);

d) comparing the ratio of the levels of the miRNAs calculated in step (c) with a corresponding control ratio, and e) (i) identifying the subject as being afflicted with the neurodevelopmental disorder when the ratio of the levels of the miRNAs calculated in step (c) is higher than the corresponding control ratio or (ii) identifying the subject as not being afflicted with the neurodevelopmental disorder when the ratio of the levels of the miRNA calculated in step (c) is not higher than the corresponding control ratio.

In one embodiment, the method further comprises the following steps, which steps can be performed simultaneously or sequentially with each other and/or with the steps (d)-(e) of the above method:

f) comparing the ratio of the levels of the miRNAs calculated in step (c) with the standard range of ratios of said miRNAs characteristic of another pathology ("a second pathology"), and g) (i) excluding the diagnosis of the second pathology in the subject if the ratio of the levels of the miRNAs calculated in step (c) does not fall within the standard range of ratios of said miRNAs characteristic of the second pathology, or (ii) not excluding the diagnosis of the second pathology in the subject if the ratio of the levels of the miRNAs calculated in step (c) falls within the standard range of ratios of said miRNAs characteristic of the second pathology.

In another embodiment, the method further comprises the following steps, which steps can be performed simultaneously or sequentially with each other and/or with the steps (a)-(e) of the above method:

f) measuring the level of a third miRNA (e.g., a brain-enriched miRNA such as, e.g., a synapse and/or neurite miRNA) in the same bodily fluid sample collected from the subject, wherein said third miRNA is enriched in an organ or an organ area(s) affected by another pathology ("a second pathology");

g) measuring the level of a fourth miRNA (e.g., a brain-enriched miRNA) in the same bodily fluid sample collected from the subject (e.g., wherein said fourth miRNA is (i) enriched in an organ or an organ area(s) which is not affected by the second pathology, or (ii) is enriched in the organ cell type which is not affected by the second pathology, or (iii) is enriched in the same organ area as the third miRNA, but its expression and/or secretion change differently than expression and/or secretion of the third miRNA during development of the second pathology);

h) calculating the ratio of the levels of the miRNAs measured in steps (f) and (g);

i) comparing the ratio of the levels of the miRNAs calculated in step (h) with the standard range of ratios of said miRNAs characteristic of the second pathology;

j) (i) identifying the subject as being afflicted with the second pathology in addition to the neurodevelopmental disorder if the ratio of the levels of the miRNAs calculated in step (h) falls within the standard range of ratios of said miRNAs characteristic of the second pathology, or (ii) excluding the diagnosis of the second pathology in the subject if the ratio of the levels of the miRNAs calculated in step (h) does not fall within the standard range of ratios of said miRNAs characteristic of the second pathology.

In a related aspect, the invention provides a method for detecting a neurodevelopmental disorder in a subject, which method comprises:

a) measuring the level of a first miRNA in a bodily fluid sample collected from the subject, wherein said first miRNA is enriched in an organ or an organ area(s) affected by the neurodevelopmental disorder;

b) measuring the level of a second miRNA in the same bodily fluid sample collected from the subject, and c) calculating the ratio of the levels of the miRNAs measured in steps (a) and (b).

The invention also provides a computer-implemented method of assigning a subject into a category of being afflicted with a neurodevelopmental disorder, which method comprises:

a. measuring the level of a first miRNA in a bodily fluid sample collected from the subject, wherein said first miRNA is enriched in an organ or an organ area(s) affected by the neurodevelopmental disorder;

b. measuring the level of a second miRNA in the same bodily fluid sample collected from the subject;

c. calculating using a suitably programmed processor, the ratio of the levels of the miRNAs measured in steps (a) and (b);

d. calculating, by the processor and based on the ratio determined in step (c), a first probability based on a first predefined probability distribution curve, wherein the first predefined probability distribution curve corresponds to the neurodevelopmental disorder;

e. calculating, by the processor and based on the ratio determined in step (c), a second probability based on a second predefined probability distribution curve, wherein the second predefined probability distribution curve corresponds to a matched control (e.g., matched by gender and/or age and/or race, etc.) or another pathology;

f. determining, by the processor, a difference between the first probability calculated in step (d) and the second probability calculated in step (e), and g. (i) identifying, by the processor, the subject as being afflicted with the neurodevelopmental disorder when the difference between the first probability and the second probability calculated in step (f) is positive or (ii) identifying the subject as not being afflicted with the neurodevelopmental disorder when the difference between the first probability and the second probability calculated in step (f) is negative.

In another aspect, the invention provides a method for treating a neurodevelopmental disorder in a subject in need thereof, which method comprises:

a) measuring the level of a first miRNA in a bodily fluid sample collected from the subject, wherein said first miRNA is enriched in an organ or an organ area(s) affected by the neurodevelopmental disorder;

b) measuring the level of a second miRNA in the same bodily fluid sample collected from the subject;

c) calculating the ratio of the levels of the miRNAs measured in steps (a) and (b);

d) comparing the ratio of the levels of the miRNAs calculated in step (c) with a corresponding control ratio, and e) administering a therapeutic or preventive treatment to the subject when the ratio of the levels of the miRNAs calculated in step (c) is higher than the corresponding control ratio In one specific embodiment, the treatment improves brain function in the subject. Non-limiting examples of useful therapies include, e.g., gene therapies (e.g., to replace the defective MECP2 gene in case of RTT (e.g., using AAV delivery vectors and/or CRISPR/Cas9 technology and/or RNA editing using the natural editing capability of the adenosine deaminases acting on RNA (ADAR) to correct G>A mutations), reactivation of the inactivated X chromosome (Xi), or at least of the (normal) inactivated MECP2 allele, speech/language therapy, occupational therapy, physical therapy, hydrotherapy. In one specific embodiment, the treatment improves liver pathology (e.g., liver medications) and/or muscle pathology (e.g., physical therapy, hydrotherapy, occupational therapy) and/or cholesterol metabolism (e.g., cholesterol medications) in the subject.

In yet another aspect, the invention provides a method for selecting subjects for enrollment in a clinical trial involving treatment of a neurodevelopmental disorder, which method comprises:

a) measuring the level of a first miRNA in a bodily fluid sample collected from the subject, wherein said first miRNA is enriched in an organ or an organ area(s) affected by the neurodevelopmental disorder;

b) measuring the level of a second miRNA in the same bodily fluid sample collected from the subject;

c) calculating the ratio of the levels of the miRNAs measured in steps (a) and (b);

d) optionally comparing the ratio of the levels of the miRNAs calculated in step (c) with a corresponding control ratio;

e) optionally (i) identifying the subject as being afflicted with the neurodevelopmental disorder when the ratio of the levels of the miRNAs calculated in step (c) is higher than the corresponding control ratio or (ii) identifying the subject as not being afflicted with the neurodevelopmental disorder when the ratio of the levels of the miRNA calculated in step (c) is not higher than the corresponding control ratio, and f) recruiting the subject in a clinical trial.

In yet another aspect, the invention provides a method for assessing an animal model of a neurodevelopmental disorder, which method comprises:

a) measuring the level of a first miRNA in a bodily fluid sample collected from the animal, wherein said first miRNA is enriched in an organ or an organ area(s) affected by the neurodevelopmental disorder;

b) measuring the level of a second miRNA in the same bodily fluid sample collected from the animal;

c) calculating the ratio of the levels of the miRNAs measured in steps (a) and (b);

d) comparing the ratio of the levels of the miRNAs calculated in step (c) with a corresponding control ratio;

e) (i) identifying the animal as a useful model of the neurodevelopmental disorder when the ratio of the levels of the miRNAs calculated in step (c) is higher than the corresponding control ratio or (ii) identifying the animal as not a useful model of the neurodevelopmental disorder when the ratio of the levels of the miRNA calculated in step (c) is not higher than the corresponding control ratio, and f) optionally using the animal for studies related to the neurodevelopmental disorder.

Non-limiting examples of useful mouse models of RTT are provided, e.g., in the Examples section, below; see also Peterson et al., Hum Mol Genet. 2016; 25(15):3303-3320 describing a rat model of RTT and Chen Y. et al. Cell. 2017; 169(5):945-955 describing a monkey model of RTT.

In one embodiment of any of the above methods, the neurodevelopmental disorder is Rett Syndrome (RTT). In another embodiment of any of the above methods, the neurodevelopmental disorder is selected from Landau-Kleffner Syndrome, Alexander Disease, Alpers' Disease, Alternating Hemiplegia, Angelman Syndrome, Ataxias and Cerebellar or Spinocerebellar Degeneration, Ataxia Telangiectasia, Attention Deficit-Hyperactivity Disorder, Autism Spectrum Disorders including Asperger Syndrome, Batten Disease, Canavan Disease, and Tourette Syndrome.

In one embodiment of any of the above methods, the control ratio is a predetermined value which represents a statistically validated threshold ratio of the levels of said first and second miRNAs (a single "cut-off" value) equal to the highest possible value within the range of corresponding values in matched healthy subjects (e.g., matched by gender and/or age and/or race, etc.). In another embodiment of any of the above methods of disease detection, the control ratio is the ratio of the levels of said first and second miRNAs in a similarly processed bodily fluid sample from the same subject collected in the past.

In one embodiment of any of the above methods of disease differentiation, the standard range of ratios of miRNAs characteristic of the second pathology is a statistically validated predetermined range of values established by determining the ratios of the same miRNAs in a cohort of subjects diagnosed with the second pathology. In one specific embodiment, the cohort of subjects diagnosed with the second pathology represents a full range of development stages of said second pathology. In another specific embodiment, the cohort of subjects diagnosed with the second pathology represents one or more development stages of said second pathology.

In one embodiment of any of the above methods of disease differentiation, the neurodevelopmental disorder is Rett Syndrome and the second pathology is selected from Landau-Kleffner Syndrome, Alexander Disease, Alpers' Disease, Alternating Hemiplegia, Angelman Syndrome, Ataxias and Cerebellar or Spinocerebellar Degeneration, Ataxia Telangiectasia, Attention Deficit-Hyperactivity Disorder, Autism Spectrum Disorders including Asperger Syndrome, Batten Disease, Canavan Disease, and Tourette Syndrome.

In one embodiment of any of the above methods of disease differentiation, the second pathology is selected from Landau-Kleffner Syndrome, Alexander Disease, Alpers' Disease, Alternating Hemiplegia, Angelman Syndrome, Ataxias and Cerebellar or Spinocerebellar Degeneration, Ataxia Telangiectasia, Attention Deficit-Hyperactivity Disorder, Autism Spectrum Disorders including Asperger Syndrome, Batten Disease, Canavan Disease, and Tourette Syndrome.

In one embodiment of any of the above methods, said neurodevelopmental disorder is Rett Syndrome (RTT) and the method further comprises determining the underlying MECP2 mutation (e.g., for predicting disease severity).

In another aspect, the invention provides a method for monitoring changes in development of a neurodevelopmental disorder in a subject (e.g., a subject who had been previously diagnosed with said neurodevelopmental disorder), which method comprises:

a) measuring the level of a first miRNA in two or more bodily fluid samples collected from the subject, wherein the samples have been collected at spaced apart time points, and wherein said first miRNA is enriched in an organ or an organ area(s) affected by the neurodevelopmental disorder;

b) measuring the level of a second miRNA in the same bodily fluids samples as in step (a);

c) calculating the ratio of the levels of the miRNA measured in steps (a) and (b) for each bodily fluid sample;

d) comparing the ratios of the levels of the miRNA calculated in step (c) between the earlier collected and later collected bodily fluid sample(s), and e) (i) determining that the neurodevelopmental disorder in the subject has progressed if the ratio of the levels of the miRNA calculated in step (c) is increased in the later collected bodily fluid sample(s) as compared to the earlier collected sample(s), or (ii) determining that the neurodevelopmental disorder in the subject has not progressed if the ratio of the levels of the miRNA calculated in step (c) is not changed in the later collected bodily fluid sample(s) as compared to the earlier collected sample(s).

In a separate aspect, the invention provides a method for monitoring the effect of a treatment on development of a neurodevelopmental disorder in a subject (e.g., a subject who had been previously diagnosed with said neurodevelopmental disorder), which method comprises:

a) measuring the level of a first miRNA in a bodily fluid sample collected from the subject prior to initiation of the treatment, wherein said first miRNA is enriched in an organ or an organ area(s) affected by the neurodevelopmental disorder;

b) measuring the level of a second miRNA in the same bodily fluid sample collected from the subject;

c) calculating the ratio of the levels of the miRNA measured in steps (a) and (b);

d) measuring the level of the same first miRNA as in step (a) in one or more bodily fluid sample(s) collected from the subject in the course of or following the treatment;

e) measuring the level of the same second miRNA as in step (b) in the same bodily fluid sample(s) as in step (d);

f) calculating the ratio of the levels of the miRNA measured in steps (d) and (e) for each bodily fluid sample;

g) comparing the ratios of the levels of the miRNA calculated in steps (c) and (f), and optionally comparing the ratios of the levels of the miRNA calculated in step (f) between different samples in step (d), and h) (i) determining that the treatment is effective for said neurodevelopmental disorder if the ratio of the levels of the miRNA calculated in step (c) is higher than the corresponding ratio(s) calculated in step (f), or (ii) determining that the treatment is not effective for said neurodevelopmental disorder if the ratio of the levels of the miRNA calculated in step (c) is not higher than the corresponding ratio(s) calculated in step (f).

In one embodiment, the method comprises a step of administering the treatment to the subject.

In a separate aspect, the invention provides a method for identifying a compound useful for slowing down the progression or treating a neurodevelopmental disorder in a subject (e.g., a subject who had been previously diagnosed with said neurodevelopmental disorder), which method comprises:

a) measuring the level of a first miRNA in a bodily fluid sample, wherein said bodily fluid sample(s) is collected from the subject prior to a test compound administration, and wherein said first miRNA is enriched in an organ or an organ area(s) affected by the neurodevelopmental disorder;

b) measuring the level of a second miRNA in the same bodily fluid sample collected from the subject;

c) calculating the ratio of the levels of the miRNA measured in steps (a) and (b);

d) measuring the level of the same first miRNA as in step (a) in one or more bodily fluid samples collected from the subject following administration of a test compound;

e) measuring the level of the same second miRNA as in step (b) in the same bodily fluid sample(s) as in step (d);

f) calculating the ratio of the levels of the miRNAs measured in steps (d) and (e) for each of the bodily fluid samples collected from the subject following administration of the test compound;

g) comparing the ratio of the levels of the miRNA calculated in steps (c) and (f), and h) (i) identifying that the test compound is useful for slowing down the progression or treating the neurodevelopmental disorder if the ratio of the levels of the miRNA calculated in step (f) is lower than the ratio of the levels of the miRNA calculated in step (c); (ii) identifying that the test compound is not useful for slowing down the progression or treating the neurodevelopmental disorder if the ratio of the levels of the miRNA calculated in step (f) is not lower than the ratio of the levels of the miRNAs calculated in step (c).

In one embodiment, the method comprises administering the test compound to the subject.

In one embodiment of any of the above methods, the neurodevelopmental disorder is Rett Syndrome (RTT). In another embodiment of any of the above methods, the neurodevelopmental disorder is selected from Landau-Kleffner Syndrome, Alexander Disease, Alpers' Disease, Alternating Hemiplegia, Angelman Syndrome, Ataxias and Cerebellar or Spinocerebellar Degeneration, Ataxia Telangiectasia, Attention Deficit-Hyperactivity Disorder, Autism Spectrum Disorders including Asperger Syndrome, Batten Disease, Canavan Disease, and Tourette Syndrome.

In one embodiment of any of the above methods, the second miRNA (i) is enriched in an organ or the organ area(s) which is not affected by the neurodevelopmental disorder, or (ii) is enriched in the organ cell type which is not affected by the neurodevelopmental disorder, or (iii) is enriched in the same organ area as the first miRNA, but its expression and/or secretion change differently than expression and/or secretion of the first miRNA during development of the neurodevelopmental disorder.

In one embodiment of any of the above methods, the first miRNA is a brain-enriched miRNA which is enriched in brain area(s) affected by the neurodevelopmental disorder.

In one specific embodiment of any of the above methods, the first miRNA is a synapse and/or neurite miRNA.

In one embodiment of any of the above methods wherein the first miRNA is a brain-enriched miRNA, the second miRNA is a brain-enriched miRNA, which (1) is enriched in brain area(s) which is not affected by the neurodevelopmental disorder or (2) is enriched in a brain cell type which is not affected by the neurodevelopmental disorder.

In one specific embodiment of any of the above methods involving the first and second miRNAs which are brain-enriched, the first brain-enriched miRNA is enriched in neurons and the second brain-enriched miRNA is enriched in glial cells.

In one embodiment of any of the above methods, the first miRNA is selected from miRNAs disclosed in Table 1.

In one embodiment of any of the above methods, wherein the neurodevelopmental disorder is RTT, the second miRNA is a brain-enriched miRNA selected from the group consisting of miRNAs which are mainly expressed in brain areas not involved in RTT, miRNAs which are mainly expressed in glial cells, and brain-enriched miRNAs downregulated in RTT.

In one embodiment of any of the above methods, wherein the neurodevelopmental disorder is RTT, the first miRNA is capable of inhibiting Mecp2 expression (e.g., miRNA disclosed in Table 2).

In one embodiment of any of the above methods, the first miRNA is a liver-enriched miRNA or a muscle-enriched miRNA (e.g., one or more liver- or muscle-enriched miRNAs disclosed in Table 1 such as, e.g., miR-122 [liver-enriched] or miR-206 [muscle-enriched]). In one specific embodiment, wherein the first miRNA is a liver- or muscle-enriched miRNA, the second miRNA is a brain-enriched miRNA or an inflammatory miRNA, wherein the concentration of said second miRNA is not changed or decreases, when level of the first miRNA increases.

In one embodiment of any of the above methods, the first miRNA is miR-146a or miR-155.

In one embodiment of any of the above methods, the first miRNA is involved in inflammatory processes in brain. In one embodiment of any of the above methods, the pair of the first miRNA and the second miRNA is selected from the group consisting of: miR-107/miR-323-3p, miR-107/miR-335-5p, miR-491-5p/miR-323-3p, miR-491-5p/miR-335-5p, miR-491-5p/miR-132, miR-491-5p/miR-411, miR-411/miR-335-5p, miR-411/miR-132, miR-107/miR-132, miR-323-3p/miR-335-5p, miR-323-3p/miR-132, miR-122/miR- 125b, miR-155/miR125b, miR-433/mir-323-3p, miR-181a/miR-491-5p, miR-181a/miR-125b, miR-181a/miR-16, miR-181a/let-7b, miR-181a/miR-132, miR-181a/miR-155, miR-181a/miR-29b, miR-432/miR-335-5p, miR-155/miR-125b, miR-155/let-7b, miR-155/miR-132, miR-122/miR-125b, miR-122/miR-155, miR-181a/let-7b, miR-122/miR-132, miR-181a/miR-132, miR-181a/miR-29b, miR-181a/miR-335-5p, miR-107/miR-491-5p, miR-122/miR-125b, miR-122/let-7b, miR-122/miR-29b, miR-122/miR-132, miR-433/miR-491-5p, miR-335-5p/miR-491-5p, miR-132/miR-206, miR-181a/miR-155, miR-146a/miR-132, miR-491-5p/miR-206, miR-107/miR-206, miR-29b/miR-206, miR-411/miR-125b, miR-432/miR-125b, miR-181a/miR-125b, miR-107/miR-125b, miR-433/miR-125b, miR-491-5p/miR-125b, miR-181a/miR-132, miR-181a/let-7b, miR-181a/miR-155, miR-411/miR-323-3p, miR-491-5p/miR-335-5p, miR-107/miR-335-5p, miR-433/miR-491-5p, miR-122/miR-107, miR-132/miR-491-5p, miR-132/miR-335-5p, miR-125b/miR-335-5p, and miR-122/miR-181a.

In one embodiment of any of the above methods, the pair of the first miRNA and the second miRNA is selected from the pairs provided in Tables 3-5 and 8-12, below.

In one embodiment of any of the above methods, the method comprises measuring the level and calculating the ratios of the levels for two or more different pairs of miRNA. In one specific embodiment, the method comprises measuring the level and calculating the ratios of the levels for one or more miRNA pair combinations selected from the group consisting of:

(a) miR-107/miR-323-3p and miR-107/miR-335-5p;

(b) miR-491-5p/miR-323-3p, miR-491-5p/miR-335-5p, miR-491-5p/miR-132, and miR-491-5p/miR-411;

(c) miR-411/miR-132, miR-107/miR-132 and miR-107/miR-335-5p;

(d) miR-323-3p/miR-335-5p and miR-323-3p/miR-132;

(e) miR-323-3p/miR-335-5p, miR-491-5p/miR-335-5p and miR-411/miR-335-5p;

miR-491-5p/miR-335-5p and miR-491-5p/miR-132;

(g) miR-181a/miR-125b, miR-122/miR-125b and miR-181a/miR-491-5p;

(h) miR-181a/miR-29b, miR-122/miR-125b and miR-411/miR-335-5p;

(i) miR-433/miR-125b, miR-122/miR-125b and miR-181a/miR-335-5p;

(j) miR-122/miR-125b, miR-181a/miR-491-5p and miR-155/miR-125b;

(k) miR-122/miR-125b, miR-181a/miR-491-5p and miR-107/miR-335-5p;

(l) miR-432/miR-335-5p, miR-155/miR-132 and miR-155/let-7b;

(m) miR-432/miR-335-5p, miR-155/let-7b and miR-433/miR-323-3p;

(n) miR-122/miR-125b, miR-181a/miR-29b and miR-107/miR-335-5p;

(o) miR-181a/miR-29b, miR-107/miR-335-5p and miR-122/let-7b;

(p) miR-122/miR-125b, miR-122/miR-29b and miR-433/miR-491-5p;

(q) miR-433/miR-491-5p, miR-122/miR-146a and miR-335-5p/miR-491-5p; and (r) miR-146a/miR-132, miR-107/miR-206 and miR-29b/miR-206.

In one embodiment of any of the above disease detection or differentiation methods, the method comprises measuring the levels of the miRNAs in two or more bodily fluid samples collected from the subject, wherein the samples have been collected at spaced apart time points.

In one embodiment of any of the above methods involving bodily fluid samples which have been collected at spaced apart time points, the bodily fluid samples are obtained several months apart (e.g., 3-6 months apart).

In one embodiment of any of the above methods, the method further comprises normalizing the levels of the first and second miRNAs to the level of a normalizer miRNA. In one specific embodiment, the normalizer miRNA is miRNA which is expressed in numerous tissues but is not significantly expressed in brain.

In one embodiment of any of the above methods, the subject does not have clinical symptoms of the neurological disorder.

In one embodiment of any of the above methods, the subject is human. In one specific embodiment, the human subject is an infant or a child. In another embodiment of any of the above methods, the subject is an experimental animal (e.g., an animal model of a neurodevelopmental disorder such as, e.g., RTT).

In one embodiment of any of the above methods, the bodily fluid is selected from the group consisting of blood plasma, serum, urine, and saliva. Any other bodily fluid can also be used, preferably, those bodily fluids that allow low cost non-invasive or minimally invasive collection and analysis.

In one embodiment of any of the above methods, the method comprises the step of collecting the bodily fluid sample(s) from the subject (e.g., prior to step (a)).

In one embodiment of any of the above methods, the level of the miRNAs is determined using a method selected from the group consisting of hybridization, polymerase chain reaction (PCR)-based detection (for example, RT-PCR), sequencing, and microfluidic technologies. Non-limiting examples of useful methods for measuring miRNA level in bodily fluids include hybridization with selective probes (e.g., using Northern blotting, bead-based flow-cytometry, oligonucleotide microchip [microarray], or solution hybridization assays such as Ambion mirVana miRNA Detection Kit), polymerase chain reaction (PCR)-based detection (e.g., stem-loop reverse transcription-polymerase chain reaction [RT-PCR], quantitative RT-PCR based array method [qPCR-array]), direct sequencing by one of the next generation sequencing technologies (e.g., Helicos small RNA sequencing, miRNA BeadArray (Illumina), Roche 454 (FLX-Titanium), and ABI SOLiD), or various microfluidic technologies. For review of additional applicable techniques see, e.g., Chen et al., BMC Genomics, 2009, 10:407; Kong et al., J Cell Physiol. 2009; 218:22-25. One of the preferred types of techniques are RT-PCR-based techniques as such techniques allow to achieve good sensitivity and specificity.

In one embodiment of any of the above methods, prior to measuring miRNA level, the miRNA is purified from the bodily fluid sample. miRNAs can be isolated and purified from bodily fluids by various methods, including, without limitation, the use of commercial kits (e.g., miRNeasy kit [Qiagen], MirVana RNA isolation kit [Ambion/ABI], miRACLE [Agilent], High Pure miRNA isolation kit [Roche], and miRNA Purification kit [Norgen Biotek Corp.]), Trizol extraction, concentration and purification on anion-exchangers, magnetic beads covered by RNA-binding substances, or adsorption of certain miRNA on complementary oligonucleotides.

In one embodiment of any of the above methods, the method further comprises reducing or eliminating degradation of the miRNAs. Useful methods for reducing or eliminating miRNA degradation include, without limitation, adding RNase inhibitors (e.g., RNasin Plus [Promega], SUPERase-In [ABI], etc.), use of guanidine chloride, guanidine isothiocyanate, N-lauroylsarcosine, sodium dodecylsulphate (SDS), or a combination thereof. Reducing miRNA degradation in bodily fluid samples is particularly important when sample storage and transportation is required prior to miRNA quantification.

To account for possible losses of a given miRNA during purification, and potentially RT-PCR inhibition, miRNA contaminants derived from dying or damaged blood or urine cells during sample isolation and treatment, variations in kidney filtration, etc., various additional methods of experimental data normalization can be employed. For example, the following quality control (QC) and/or normalization methods can be used in the present invention:

a) Ubiquitous miRNAs can be used for QC by comparing their concentrations in subject's bodily fluid with pre-established normal values.

b) Synthetic small RNA (e.g., non-human miRNA) oligonucleotides can be synthesized and used as controls for losses during purification and/or RT-PCR inhibition (e.g., by adding them to bodily fluid samples before RNA purification).

c) To account for variations in kidney filtration (when working with urine samples), miRNA concentration in urine can be normalized on creatinine and/or albumin level.

In one embodiment of any of the above methods, neurodevelopmental disorder detection based on miRNA levels is combined with additional methods of detection. Non-limiting examples of such additional methods include, e.g., genetic testing (e.g., MECP2 mutation determination for RTT), hearing test, eye and/or vision exam, positron emission tomography (PET), computed tomography (CT), magnetic resonance imaging (MM), multiphoton imaging, magnetoencephalography (MEG), and electroencephalography (EEG).

In one embodiment of any of the above disease detection or disease monitoring methods, the method further comprises administering a therapeutic or preventive treatment to the subject. Non-limiting examples of useful symptomatic and prophylactic treatments include, for example, gene therapies (e.g., to replace the defective MECP2 gene in case of RTT (e.g., using AAV delivery vectors and/or CRISPR/Cas9 technology and/or RNA editing using the natural editing capability of the adenosine deaminases acting on RNA (ADAR) to correct G>A mutations), reactivation of the inactivated X chromosome (Xi), or at least of the (normal) inactivated MECP2 allele, hydrotherapy, physical therapies, occupational therapies, speech-language therapies, nutritional support, controlling seizures, controlling muscle stiffness, GI treatments, liver treatments, heart treatments, cholesterol-lowering treatments, and treatments for breathing problems. The therapeutic or preventative treatment may be administered prior the appearance of one or more clinical symptoms of the neurodevelopmental disorder. In the case of when the neurodevelopmental disorder is RTT, effective treatment can mean RTT improvement (decrease of a monitored biomarker miRNA ratio) or prevention/inhibition of further development of RTT (monitored biomarker miRNA ratio stays the same or increases slower).

In one embodiment of any of the above disease detection or disease progression monitoring methods, the method further comprises recruiting the subject in a clinical trial.

In conjunction with the above methods of the invention, the invention also provides various kits. Non-limiting examples of the kits of the invention include:

1. A kit for detecting a neurodevelopmental disorder (e.g., RTT) comprising primers and/or probes specific for one or more pairs of miRNAs selected from the group consisting of: miR-107/miR-323-3p, miR-107/miR-335-5p, miR-491-5p/miR-323-3p, miR-491-5p/miR-335-5p, miR-491-5p/miR-132, miR-491-5p/miR-411, miR-411/miR-335-5p, miR-411/miR-132; miR-107/miR-132, miR-323-3p/miR-335-5p, miR-323-3p/miR-132, miR-122/miR-125b, miR-155/miR125b, miR-433/mir-323-3p, miR-181a/miR-491-5p, miR-181a/miR-125b, miR-181a/miR-16, miR-181a/let-7b, miR-181a/miR-132, miR-181a/miR-155, miR-181a/miR-29b, miR-432/miR-335-5p, miR-155/miR-125b, miR-155/let-7b, miR-155/miR-132, miR-122/miR-125b, miR-122/miR-155, miR-181a/let-7b, miR-122/miR-132, miR-181a/miR-132, miR-181a/miR-29b, miR-181a/miR-335-5p, miR-107/miR-491-5p, miR-122/miR-125b, miR-122/let-7b, miR-122/miR-29b, miR-122/miR-132, miR-433/miR-491-5p, miR-335-5p/miR-491-5p, miR-132/miR-206, miR-181a/miR-155, miR-146a/miR-132, miR-491-5p/miR-206, miR-107/miR-206, miR-29b/miR-206, miR-411/miR-125b, miR-432/miR-125b, miR-181a/miR-125b, miR-107/miR-125b, miR-433/miR-125b, miR-491-5p/miR-125b, miR-181a/miR-132, miR-181a/let-7b, miR-181a/miR-155, miR-411/miR-323-3p, miR-491-5p/miR-335-5p, miR-107/miR-335-5p, miR-433/miR-491-5p, miR-122/miR-107, miR-132/miR-491-5p, miR-132/miR-335-5p, miR-125b/miR-335-5p, and miR-122/miR-181a.

2. A kit for detecting a neurodevelopmental disorder (e.g., RTT) comprising primers and/or probes specific for one or more pairs of miRNAs selected from the pairs provided in Tables 3-5 and 8-12, below.

3. A kit for detecting a neurodevelopmental disorder comprising primers and/or probes specific for one or more combinations of pairs of miRNAs selected from the group consisting of:

(a) miR-107/miR-323-3p and miR-107/miR-335-5p;

(b) miR-491-5p/miR-323-3p, miR-491-5p/miR-335-5p, miR-491-5p/miR-132, and miR-491-5p/miR-411;

(c) miR-411/miR-132, miR-107/miR-132 and miR-107/miR-132;

(d) miR-323-3p/miR-335-5p and miR-323-3p/miR-132;

(e) miR-323-3p/miR-335-5p, miR-491-5p/miR-335-5p and miR-411/miR-335-5p;

(f) miR-491-5p/miR-335-5p and miR-491-5p/miR-132;

(g) miR-181a/miR-125b, miR-122/miR-125b and miR-181a/miR-491-5p;

(h) miR-181a/miR-29b, miR-122/miR-125b and miR-411/miR-335-5p;

(i) miR-433/miR-125b, miR-122/miR-125b and miR-181a/miR-335-5p;

(j) miR-122/miR-125b, miR-181a/miR-491-5p and miR-155/miR-125b;

(k) miR-122/miR-125b, miR-181a/miR-491-5p and miR-107/miR-335-5p;

(l) miR-432/miR-335-5p, miR-155/miR-132 and miR-155/let-7b;

(m) miR-432/miR-335-5p, miR-155/let-7b and miR-433/miR-323-3p;

(n) miR-122/miR-125b, miR-181a/miR-29b and miR-107/miR-335-5p;

(o) miR-181a/miR-29b, miR-107/miR-335-5p and miR-122/let-7b;

(p) miR-122/miR-125b, miR-122/miR-29b and miR-433/miR-491-5p;

(q) miR-433/miR-491-5p, miR-122/miR-146a and miR-335-5p/miR-491-5p; and (r) miR-146a/miR-132, miR-107/miR-206 and miR-29b/miR-206.

Any of the above kits can further comprise miRNA isolation means and/or miRNA purification means and/or instructions for use.

These and other aspects of the present invention will be apparent to those of ordinary skill in the art in the following description, claims and drawings.

BRIEF DESCRIPTION OF THE DRAWINGS

FIGS. 4A-4H are graphs showing additional biomarker miRNA pairs effectively distinguishing wild type and Mecp2$^{tm1.1Bird}$ Null mice. miRNA ratios are presented as log 10 of $2^{\Delta Ct}$. Average for each pair is indicated.

FIGS. 6A-6F are graphs showing ratios of miRNA levels (biomarker miRNA pairs) in plasma of wild type and Mecp2$^{tm1.1Jae}$ Het mice. miRNA ratios are presented as log 10 of $2^{\Delta Ct}$. Average for each pair is indicated.

FIGS. 8A-8E are graphs showing biomarker miRNA pairs effectively distinguishing wild type and Mecp2$^{tm1.1Bird}$ Het mice. miRNA ratios are presented as log 10 of $2^{\Delta Ct}$. Average for each pair is indicated.

DETAILED DESCRIPTION OF THE INVENTION

Figure 1A:
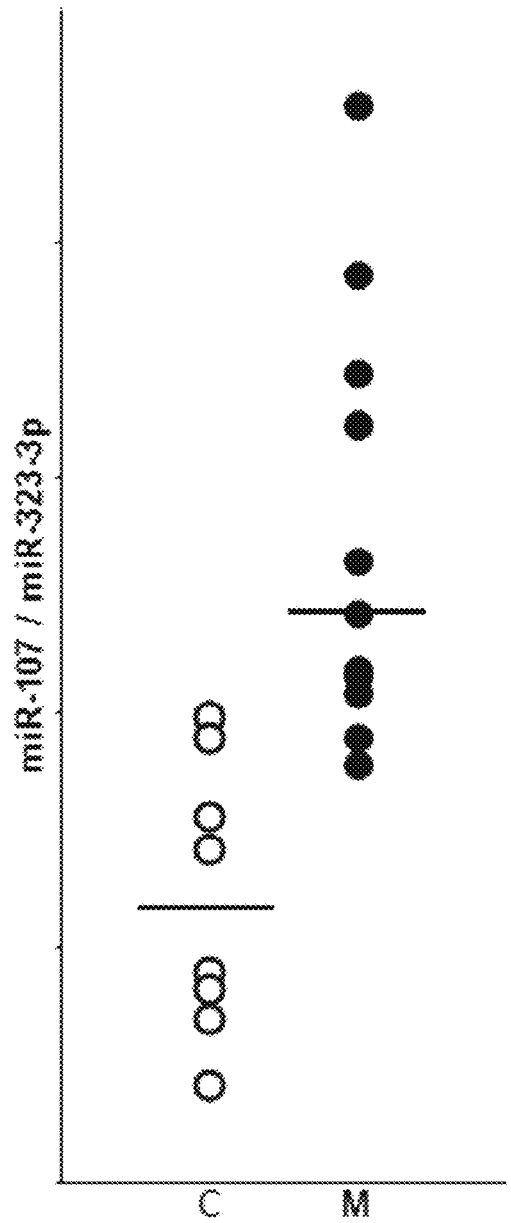
FIGS. 1A-1E are graphs showing ratios of miRNA levels (biomarker miRNA pairs) in plasma of wild type and Mecp2$^{tm1.1Jae}$ Null mice. miRNA ratios are presented as log 10 of $2^{\Delta Ct}$. Average for each pair is indicated.
Figure 1B:
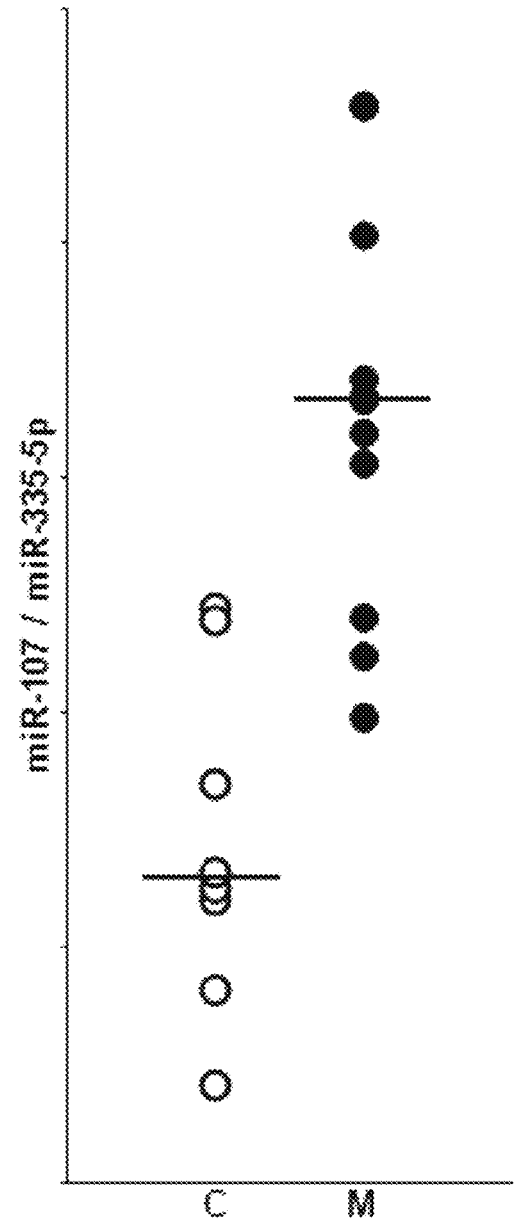
Figure 1C:
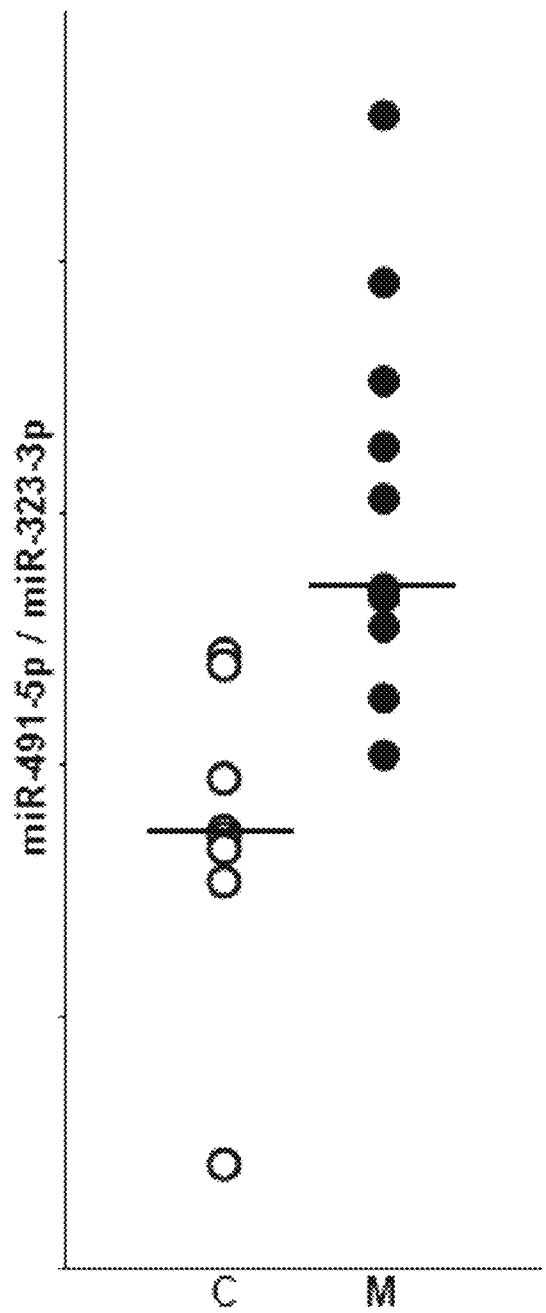
Figure 1D:
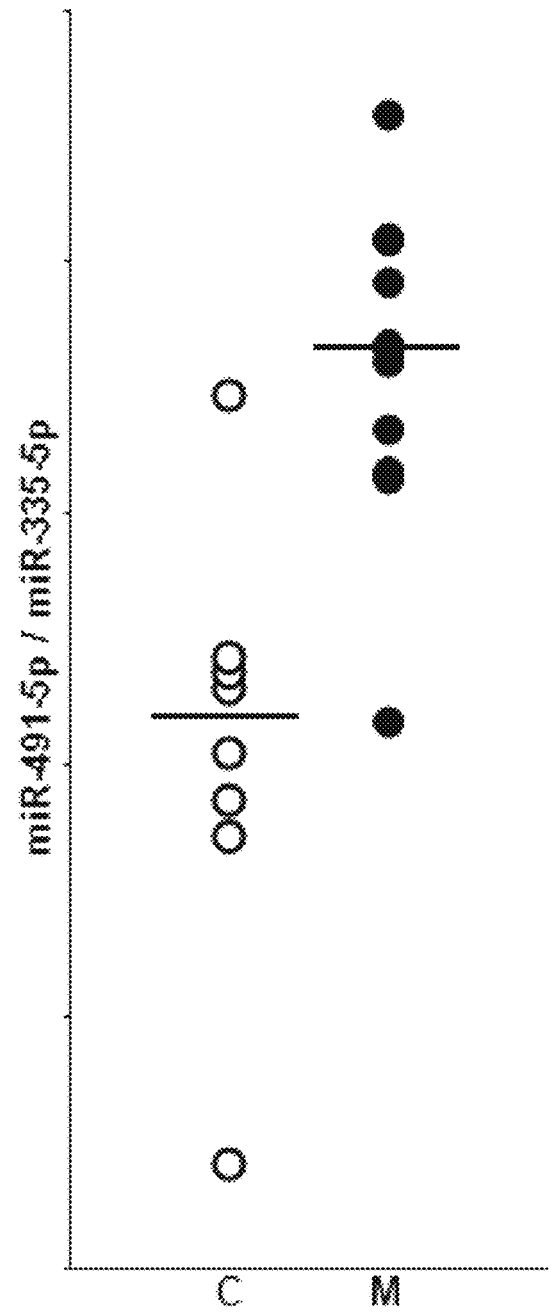
Figure 1E:
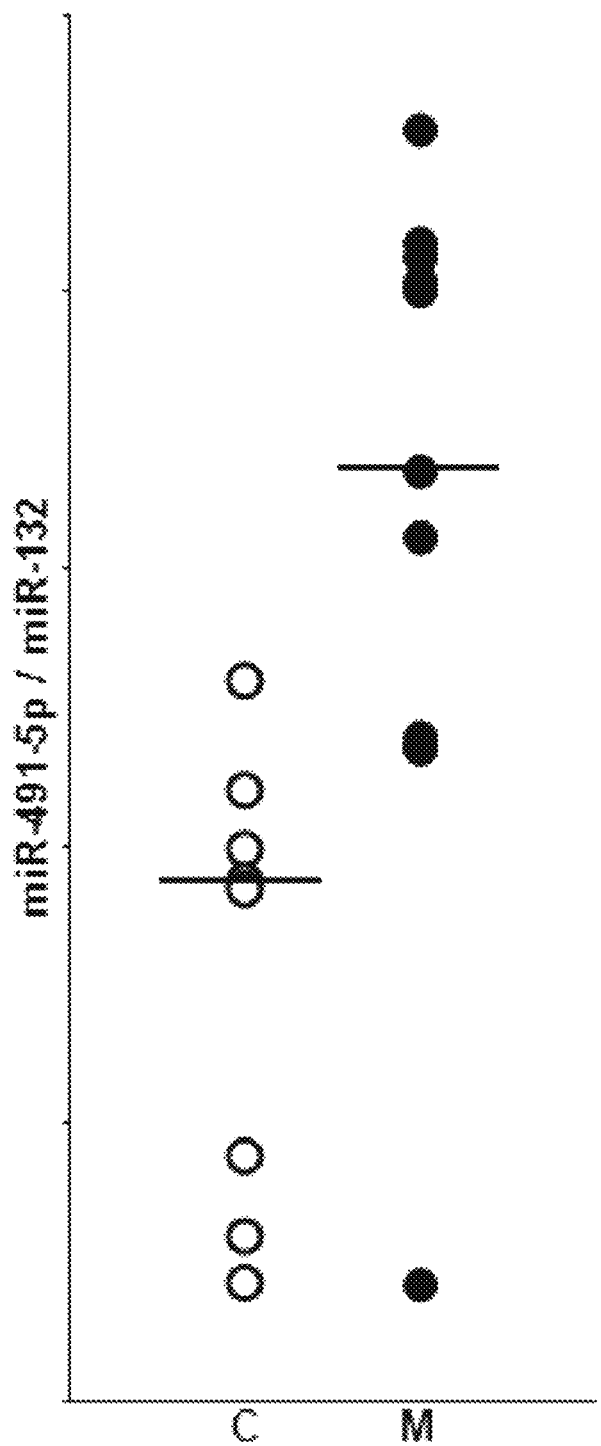

NDDs differ from neurodegenerative diseases by no or very limited neuronal death [Armstrong et al. Selective Dendritic Alterations in the Cortex of Rett Syndrome. J. Neuropathol. Exp. Neurol. 54, 195 (1995); Katz D M et al. Preclinical research in Rett syndrome: setting the foundation for translational success. Dis. Models and Mechanisms, 5, 733-745 (2012)]. NDDs are characterized by synapse and/or neurite dysfunction in particular brain areas. The present inventors have hypothesized that such synapse and/or neurite dysfunction can be accompanied by changes in miRNA expression and secretion, leading to increased or decreased levels of particular miRNAs in plasma/serum or other bodily fluids, such as, e.g., urine or saliva. The present inventors have hypothesized that, since miRNAs are evolutionary conserved, one can expect that same miRNAs may be used as biomarkers of RTT in human, mouse and other animals. Data on miRNA expression in brain of RTT subjects are limited and obtained mainly in various mouse models with mutant MECP2 [Wu et al. Genome-wide analysis reveals methyl-CpG-binding protein 2-dependent regulation of microRNAs in a mouse model of Rett syndrome. Proc. Natl. Acad. Sci. 107, 18161-18166 (2010); Urdinguio et al. Disrupted microRNA expression caused by Mecp2 loss in a mouse model of RTT. Epigenetics, 5, 656-663 (2010)]. Several factors cause changes in miRNA expression due to inactivation of Mecp2. First, being involved in transcription regulation Mecp2 affects synthesis of some miRNAs [Leon-Guerrero et al. In sickness and in health: the role of methyl-CpG binding protein 2 in the central nervous system. Europ. J. Neurosci. 33, 1563-1574, (2011)] and its inactivation changes transcription of those miRNAs. Second, expression of some miRNAs can be changed indirectly due to other cellular effects of Mecp2 inactivity. Since the presently proposed approach for developing RTT diagnostics is based on analysis of brain-enriched miRNAs and other miRNAs circulating in bodily fluids (e.g., miR-122 and miR-206 highly enriched in liver and muscle, respectively, two organs involved in RTT pathology, as well as miR-155 and miR-146 associated with inflammatory processes in brain and other organs), changes in miRNA secretion/excretion caused by inactivity of Mecp2 are also very important. Several brain areas, such as substantia nigra/midbrain (Gantz et al. J. Neurosci. 2011; 31: 12629-12637; Panayotis et al. Neurobiol. Dis. 2011, 41: 385-397), frontal cortex (Gibson et al. BMC Neurosci. 2010; 11:53), hippocampus (Toloe et al. Mol. Cell Neurosci. 2014; 59: 47-56), and hypothalamus (Sakai et al. Eur. J. Med. Genet. 2013; 56: 475-483) are affected in RTT. In addition, it is important that RTT development leads to pathologies of liver, muscles, cholesterol metabolism (Philppart, Am J Med Genet Suppl. 1986; 1:111-118; Buchovecky et al., Nat. Genet. 2013; 45:1013-1020; Justice et al., Rare Dis. 2013; 1:e27265; Killian et al., Pediatr Neurol. 2017: 70:20-25; Conti V et al. PLoS One. 2015; 10:e0130183; Gold V A et al. Mitochondrion. 2014; 15:10-7; Leonard H. et al. Nat Rev Neurol. 2017; 13:37-51) and respectively circulating miR-NAs, enriched in these organs and/or involved in related metabolic processes can be potential biomarkers of different RTT stages.

Taken together, the present invention is based on the following ideas and findings made by the present inventors:
(1) changes in concentrations of circulating miRNAs enriched in the brain, and more specifically in brain areas involved in a particular pathology, are more likely to reflect associated pathologic processes in the brain than ubiquitous or other brain-enriched miRNAs;
(2) miRNAs present in neurites and synapses should be analyzed, because dysfunction and destruction of neurites and synapses is characteristic of NDDs, and therefore, can affect expression and secretion of these miRNAs;

(3) to compensate for processes unrelated directly to a particular pathology, e.g., changes in blood supply or blood-brain barrier permeability, the present inventors used the "biomarker miRNA pair" approach normalizing miRNAs enriched in neurons of damaged brain area(s) by other brain-enriched miRNAs, such as, e.g., (i) miRNAs enriched in a brain area(s) which is not affected by the NDD which is being diagnosed, or (ii) miRNAs enriched in a brain cell type which is not affected by the NDD which is being diagnosed, or (iii) miRNAs enriched in the same brain area as the biomarker miRNA, but its expression and/or secretion change differently than expression and/or secretion of the biomarker miRNA during development of the NDD which is being diagnosed;

(4) high correlation of plasma concentrations of miRNAs used as numerator and denominator in a biomarker miRNA pair is very important for its sensitivity and specificity;

(5) pathology of other organs can be detected by analysis of circulating in bodily fluids miRNAs which are enriched in respective organs or are involved in related metabolic pathways.

The present invention is based on analysis of the ratios of the levels for pairs of circulating cell-free miRNA in bodily fluids, wherein, for example, both miRNA in the pair are brain-enriched, and either (i) are enriched in certain brain areas, which are (for one miRNA in the pair) or are not (for the other miRNA in the pair) affected by the NDD (e.g., by being involved in NDD development), or (ii) are enriched in different cell types (e.g., neurons and glial cells), or (iii) are enriched in the same brain area but whose expression and/or secretion change differently due to NDD development. Brain-enriched miRNAs which are particularly useful as numerators in the biomarker miRNA pairs of the invention include neuronal miRNAs present in neurites and synapses (i.e., synapse and/or neurite miRNAs), whose normal functioning suffers in RTT or other NDDs. Since various NDDs are characterized by neuronal pathology in different brain areas such biomarker miRNA pairs can be used for differentiating those pathologies from each other independent of their clinical symptoms, if any. Since the diseases progression also leads to pathological changes in organs and tissues outside of brain (e.g., liver, muscle) and/or pathological changes in various metabolic pathways (e.g., cholesterol metabolism, inflammatory processes), miRNAs enriched in those organs or involved in respective pathways (for example, miRNAs inhibiting Mecp2 expression disclosed in Table 2, inflammatory miR-146a and miR-155, miR-122 highly enriched in liver and involved in the cholesterol metabolism) can also be used for prognostic, diagnostic and monitoring purposes. In addition, discovered biomarker miRNA pairs, reflecting important events in pathology development, could be used for patient selection and stratification for clinical trials, early patient treatment, disease and treatment monitoring as well as for drug screening. Due to evolutionary conservation of miRNAs the same biomarker miRNA pairs may be also used in animal models for preclinical phase of drug development.

Use of brain-enriched miRNA in the methods of the invention significantly increases chances that changes of their levels in bodily fluids are caused by brain pathology, and changes in bodily fluid concentration of miRNA enriched in a particular brain area should be indicative of pathology in that brain part. For example, changes in levels of midbrain- or cortex-enriched miRNA would be associated with RTT, reflecting synapse and neuronal dysfunctions in these brain areas. In addition, concentrations of brain-enriched miRNA in blood cells are low, which decreases contamination of plasma and serum by miRNA leakage during purification of these bodily fluids. Use of liver- and/or muscle-enriched miRNAs as additional biomarkers is related to the fact that liver and muscle are involved in the Rett development (see, e.g., Amir, R. E., et al. Rett syndrome is caused by mutations in X-linked MECP2, encoding methyl-CpG-binding protein. Nat Genet., 23, 185-188 (1999); Armstrong D D. Rett syndrome neuropathology review 2000. Brain Dev. 23 Suppl 1, S72-76 (2001); Lyst, M. J., Bird, A. Rett syndrome: a complex disorder with simple roots. Nat. Rev. Genet., 16, 261-275 (2015).

The concentrations of miRNAs detected in bodily fluids depend on many biological and technical factors. Biological factors include miRNA levels in various tissues, intensity of secretion and excretion into extracellular space, forms of circulating miRNAs (exosomes and other vesicles, complexes with proteins and lipids) affecting their ability to cross various barriers, e.g. blood-brain, placental, and kidney barriers, and miRNA stability and half-life in the bloodstream. Technical factors include variability in methods of bodily fluid collection and storage, methods used for miRNA extraction, and presence in bodily fluids of various factors affecting miRNA purification and quantitation. As a consequence, the importance of miRNA normalization is broadly recognized (Meyer et al., Biotechnol. Lett. 2010; 32: 1777-1788). At the same time, no single normalization method is commonly accepted.

The present invention is based on the use of specific biomarker/normalizer miRNA pairs instead of (or in addition to) normalization per ubiquitous RNA or an average of numerous miRNAs. The use of brain-enriched biomarker miRNA pairs (one as a numerator and another one as a denominator in a ratio) has several advantages. First, any pathology is usually associated with up-regulation of some miRNAs and down-regulation of other miRNAs, thus considering miRNA pairs of up- and down-regulated miRNAs may increase test sensitivity and specificity. Second, the use of a pair of brain-enriched miRNAs, rather than one brain-enriched miRNA, decreases potential overlap with pathologies of other organs. Third, one can expect that changes unrelated to or non-specific for a pathology of interest, such as, e.g., changes in blood supply, blood-brain permeability and others, will be better compensated for by using the pair of miRNAs enriched in the same organ. In addition, changes in relative concentrations of miRNAs enriched in different brain areas or different cell types (e.g., neurons and glial cells) may be an indicator of disease progression. Concentration of miRNAs enriched in other organs suffering in Rett progression (e.g., liver or muscle) can be normalized on experimentally found miRNAs (see, for example, Tables 9C and 12A-C), which provide pairs most effectively separating Rett from control or various Rett stages from each other.

Another innovative aspect of the present invention is the use of probabilistic approach in addition to or instead of calculating ratios of miRNA concentrations in plasma. The use of integral distribution curves, which characterize probabilities of a subject belonging to control or having a pathology has such advantages as better definition of diagnostic uncertainty zone, simplicity of combining biomarkers of different nature (e.g., protein levels, imaging techniques and miRNA levels) and others.

In the present invention, since various miRNA are involved in regulation of different processes, combination of several miRNA pairs were also tested to find out the groups of miRNA pairs providing the highest test accuracy. Non-limiting examples of such groups for RTT detection include:
(a) miR-107/miR-323-3p and miR-107/miR-335-5p;
(b) miR-491-5p/miR-323-3p, miR-491-5p/miR-335-5p, miR-491-5p/miR-132, and miR-491-5p/miR-411;
(c) miR-411/miR-132 and miR-107/miR-132;
(d) miR-323-3p/miR-335-5p and miR-323-3p/miR-132;
(e) miR-323-3p/miR-335-5p, miR-491-5p/miR-335-5p and miR-411/miR-335-5p.
(f) miR-181a/miR-125b+miR-122/miR-125b+miR-181a/miR-491-5p;
(g) miR-181a/miR-29b+miR-122/miR-125b+miR-411/miR-335-5p;
(h) miR-433/miR-125b+miR-122/miR-125b+miR-181a/miR-335-5p;
(i) miR-122/miR-125b+miR-181a/miR-491-5p+miR-155/miR-125b;
(j) miR-122/miR-125b+miR-181a/miR-491-5p+miR-107/miR-335-5p;
(k) miR-409-3p/miR-134+miR-433/miR-323-3p+miR-335-5p/let-7b;
(l) miR-29b/miR-125b+miR-409-3p/miR-134+miR-433/miR-323-3p;
(m) miR-181a/miR-335-5p+miR-107/miR-335-5p+miR-122/miR-132;
(n) miR-181a/miR-155+miR-181a/miR-335-5p+miR-107/miR-335-5p;
(o) miR-122/miR-146a+miR-132/miR-491-5p;
(p) miR-122/miR-491-5p+miR-122/miR-29b+miR-132/miR-491-5p.

Definitions

As used herein, the term "organ-enriched" means that miRNA concentration in a given organ is at least 4-5 times higher than in other organs. For example, "brain-enriched" means that miRNA concentration in brain is at least 4-5 times higher than in other organs.

As used herein in connection with miRNA enrichment in a certain area of the brain, the term "enriched" means that miRNA concentration in said area of the brain is higher (preferably, at least 2-fold higher, more preferably at least 5-fold higher, most preferably at least 10-fold higher) than in brain in general. The term refers to the difference in concentrations within the brain areas (e.g., as measured using qRT-PCR).

Within the meaning of the present invention, the term "synapse and/or neurite miRNA" refers to miRNA which (i) is "brain-enriched" and (ii) is present in a synapse and/or neurite (i.e., axon and/or dendrite and/or spine). To be useful in the methods of the present invention, synapse and/or neurite miRNAs should be detectable in bodily fluids as a result of their release from neurons (e.g., due to secretion, neurite/synapse destruction or neuronal death).

The term "neurite" as used herein refers to any projection from the cell body of a neuron. This projection can be an axon, a dendrite, or a spine.

The term "axon" refers to a long, slender projection of a neuron that conducts electrical impulses away from the neuron's cell body or soma. Axons are distinguished from dendrites by several features, including shape (dendrites often taper while axons usually maintain a constant radius), length (dendrites are restricted to a small region around the cell body while axons can be much longer), and function (dendrites usually receive signals while axons usually transmit them). Axons and dendrites make contact with other cells (usually other neurons but sometimes muscle or gland cells) at junctions called synapses.

The term "dendrite" refers to a branched projection of a neuron that acts to conduct the electrochemical stimulation received from other neural cells to the cell body of the neuron from which the dendrites project.

The term "synapse" refers to specialized junctions, through which neurons signal to each other and to non-neuronal cells such as those in muscles or glands. A typical neuron gives rise to several thousand synapses. Most synapses connect axons to dendrites, but there are also other types of connections, including axon-to-cell-body, axon-to-axon, and dendrite-to-dendrite. In the brain, each neuron forms synapses with many others, and, likewise, each receives synaptic inputs from many others. As a result, the output of a neuron may depend on the input of many others, each of which may have a different degree of influence, depending on the strength of its synapse with that neuron. There are two major types of synapses, chemical synapses and electrical synapses. In electrical synapses, cells approach within about 3.5 nm of each other, rather than the 20 to 40 nm distance that separates cells at chemical synapses. In chemical synapses, the postsynaptic potential is caused by the opening of ion channels by chemical transmitters, while in electrical synapses it is caused by direct electrical coupling between both neurons. Electrical synapses are therefore faster than chemical synapses.

The term "normalizer miRNA" as used herein refers to miRNA which is used for normalization of biomarker miRNA concentration to account for factors that affect appearance and/or stability of miRNA in bodily fluids but are not related to a target pathology.

The terms "neurodevelopmental disorders", "neurodevelopmental diseases" and "NDDs" refer to pathologies caused by disturbances of the nervous system development such as, e.g., Rett Syndrome, Landau-Kleffner Syndrome, Alexander Disease, Alpers' Disease, Alternating Hemiplegia, Angelman Syndrome, Ataxias and Cerebellar or Spinocerebellar Degeneration, Ataxia Telangiectasia, Attention Deficit-Hyperactivity Disorder, Autism Spectrum Disorders including Asperger Syndrome, Batten Disease, Canavan Disease, and Tourette Syndrome.

The term "development of a neurodevelopmental disorder" is used herein to refer to any negative change in the extent/severity of a metabolic and/or structural change in individual neurons and/or any increase in the number of neurons affected. The phrase "improvement of a neurodevelopmental disorder" and similar terms refer to any positive change in the extent/severity of a metabolic and/or structural change in individual neurons and/or any decrease in the number of neurons affected.

The term "associated with" is used to encompass any correlation, co-occurrence and any cause-and-effect relationship.

The terms "microRNA" or "miRNA" as used herein refer to a class of small approximately 22 nt long non-coding RNA molecules. They play important roles in the regulation of target genes by binding to complementary regions of messenger transcripts (mRNA) to repress their translation or regulate degradation (Griffiths-Jones Nucleic Acids Research, 2006, 34, Database issue: D140-D144) Frequently, one miRNA can target multiple mRNAs and one mRNA can be regulated by multiple miRNAs targeting different regions of the 3' UTR. Once bound to an mRNA, miRNA can modulate gene expression and protein production by affecting, e.g., mRNA translation and stability (Baek et al., Nature 455(7209):64 (2008); Selbach et al., Nature 455(7209):58 (2008); Ambros, 2004, Nature, 431, 350-355; Bartel, 2004, Cell, 116, 281-297; Cullen, 2004, Virus Research., 102, 3-9; He et al., 2004, Nat. Rev. Genet., 5, 522-531; and Ying et al., 2004, Gene, 342, 25-28). Unless otherwise noted, the name of a specific miRNA refers to a mature miRNA sequence. Under current nomenclature rules, human miRNAs are preceded with the prefix "hsa-" (i.e., an abbreviation for *Homo sapiens*). Throughout the specification and figures the hsa- prefix may be dropped for purposes of abbreviation, thus, for example, "hsa-miR-155" and "miR-155" would represent the same RNA sequence.

Examples of miRNAs useful in the methods of the present invention include, without limitation, miR-107, miR-323-3p, miR-491-5p, miR-335-5p, miR-132, and miR-411. Information on most currently known miRNAs can be found in the miRNA database miRBase (available at the world wide web at mirbase.org). See also Burside et al., BMC Genomics 9:185 (2008); Williams et al., BMC Genomics 8:172 (2007); Landgraf et al., Cell 129:1401 (2007).

The term "miRNA array" refers to a multiplex technology used in molecular biology and in medicine. It consists of an arrayed series of multiple (e.g., thousands) microscopic spots of oligonucleotides, each containing a specific sequence (probe) complementary to a particular target miRNA. After probe-target hybridization under high-stringency conditions the resulting hybrids are usually detected and quantified by quantifying fluorophore-, silver-, or chemiluminescence-labeled targets to determine relative abundance of miRNA. In the methods of the present invention, both custom-made and commercially available miRNA arrays can be used. Examples of useful commercially available miRNA arrays (based on various methods of target labeling, hybrid detection and analysis) include arrays produced by Agilent, Illumina, Invitrogen, Febit, and LC Sciences.

The term "next generation sequencing technologies" broadly refers to sequencing methods which generate multiple sequencing reactions in parallel. This allows vastly increased throughput and yield of data. Non-limiting examples of commonly used next generation sequencing platforms include Helicos small RNA sequencing, miRNA BeadArray (Illumina), Roche 454 (FLX-Titanium), and ABI SOLiD.

An "individual" or "subject" or "animal", as used herein, refers to humans, veterinary animals (e.g., cats, dogs, cows, horses, sheep, pigs, etc.) and experimental animal models of neurodevelopmental diseases. In a preferred embodiment, the subject is a human.

The term "purified" as used herein refers to material that has been isolated under conditions that reduce or eliminate the presence of unrelated materials, i.e., contaminants, including native materials from which the material is obtained. For example, RNA purification includes elimination of proteins, lipids, salts and other unrelated compounds present in bodily fluids. Besides, for some methods of analysis a purified miRNA is preferably substantially free of other RNA oligonucleotides contained in bodily fluid samples (e.g., rRNA and mRNA fragments, ubiquitous miR-NAs, which are expressed at high levels in almost all tissues [e.g., miR-16], etc.). As used herein, the term "substantially free" is used operationally, in the context of analytical testing of the material. Preferably, purified material substantially free of contaminants is at least 50% pure; more preferably, at least 90% pure, and still more preferably at least 99% pure. Purity can be evaluated by chromatography, gel electrophoresis, composition analysis, biological assay, and other methods known in the art.

As used herein, the term "similarly processed" refers to samples (e.g., bodily fluid samples or purified miRNAs) which have been obtained using the same protocol.

In the context of the present invention insofar as it relates to any of the disease conditions recited herein, the terms "treat", "treatment", and the like mean to relieve or alleviate at least one symptom associated with such condition, or to slow or reverse the progression of such condition, or to arrest, delay the onset (i.e., the period prior to clinical manifestation of a disease) and/or reduce the risk of developing or worsening a disease. Within the meaning of the present invention, the term "treat" also encompasses preventing and/or reducing a positive symptom associated with neurodevelopmental disorders, such as, e.g., seizures, muscle stiffness, GI, heart, and breathing problems.

The term "about" or "approximately" means within a statistically meaningful range of a value. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art.

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition. Cold Spring Harbor, N.Y.: Cold Spring Harbor Laboratory Press, 1989 (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; B. Perbal, A Practical Guide To Molecular Cloning (1984); Ausubel, F. M. et al. (eds.). Current Protocols in Molecular Biology. John Wiley & Sons, Inc., 1994. These techniques include site directed mutagenesis as described in Kunkel, Proc. Natl. Acad. Sci. USA 82: 488-492 (1985), U.S. Pat. No. 5,071,743, Fukuoka et al., Biochem. Biophys. Res. Commun. 263: 357-360 (1999); Kim and Maas, BioTech. 28: 196-198 (2000); Parikh and Guengerich, BioTech. 24: 4 28-431 (1998); Ray and Nickoloff, BioTech. 13: 342-346 (1992); Wang et al., BioTech. 19: 556-559 (1995); Wang and Malcolm, BioTech. 26: 680-682 (1999); Xu and Gong, BioTech. 26: 639-641 (1999), U.S. Pat. Nos. 5,789,166 and 5,932,419, Hogrefe, Strategies 14. 3: 74-75 (2001), U.S. Pat. Nos. 5,702,931, 5,780,270, and 6,242,222, Angag and Schutz, Biotech. 30: 486-488 (2001), Wang and Wilkinson, Biotech. 29: 976-978 (2000), Kang et al., Biotech. 20: 44-46 (1996), Ogel and McPherson, Protein Engineer. 5: 467-468 (1992), Kirsch and Joly, Nucl. Acids. Res. 26: 1848-1850 (1998), Rhem and Hancock, J. Bacteriol. 178: 3346-3349 (1996), Boles and Miogsa, Curr. Genet. 28: 197-198 (1995), Barrenttino et al., Nuc. Acids. Res. 22: 541-542 (1993), Tessier and Thomas, Meths. Molec. Biol. 57: 229-237, and Pons et al., Meth. Molec. Biol. 67: 209-218.

Methods for Identification of Diagnostic miRNA Pairs

To identify the most promising biomarker miRNA pairs, the present inventors used the following approach: selection of a numerator and a denominator for each pair from those circulating miRNAs, which significantly correlate (Spearman's rank correlation coefficient r>0.8) in a respective bodily fluid of different individuals. Concentrations of miRNAs in plasma depend on numerous factors, including (i) levels of miRNA expression in various organs and tissues; (ii) levels of miRNA secretion from different cell types; (iii) stability of miRNAs in extracellular space and their appearance in plasma in different forms, such as exosomes and other microvesicles, complexes with proteins, lipids and, possibly, other molecules; and (iv) blood-brain barrier permeability for brain-enriched miRNAs. A pathological process may affect some or all of these factors. The present inventors suggest that a nominator and a denominator of an effective biomarker miRNA pair should share some of these basic common factors (e.g., both are brain-enriched and secreted in exosomes) and would change differently in response to a pathology. This does not mean that any correlated miRNA will form a good biomarker pair, since if they are similarly changed by pathology their ratio will mask those changes. The miRNA correlation in a pair is less important if the level of a biomarker miRNA used as a numerator is significantly (more than 3-5 times) changed due to pathology development.

The present invention provides a method of "promising" miRNA pair selection, which method comprises the following steps:

1. Concentrations of miRNAs pre-selected on the basis of their enrichment in an organ of interest (e.g., brain) are measured in a bodily fluid (e.g., plasma, serum, saliva, urine) of at least two comparative cohorts (e.g., a disease and control for a diagnostic test, two diseases for a test capable of differentiating two pathologies, a disease at different stages of pathologic process development, or a disease before and after treatment for monitoring tests).

2. Means of each miRNA concentrations are calculated for comparative cohorts.

3. The difference between the means for each miRNA from two comparative cohorts is calculated and miRNAs are divided in two groups: (i) with high difference values; and (ii) with low or with opposite sign difference values.

4. miRNAs from different groups are combined as potential biomarker pairs if parameters determined in step 3 differ at least 1.5 times. One miRNA is used as a numerator and another miRNA is used as a denominator in a potential "promising" miRNA pair.

5. To further reduce an impact of individual variations of each particular miRNA concentration in plasma or other bodily fluid, miRNA with high positive correlation (Spearman's rank correlation coefficient r calculated for all samples in compared groups is >0.8) are selected as a numerator and a denominator for the biomarker pair. This step significantly decreases the number of potential biomarker miRNA pairs, reduces variance of selected biomarkers caused by factors unrelated to processes differentiating two comparative cohorts and significantly increases test sensitivity and specificity.

The order of steps 3-4 and step 5 can be switched as follows: After step 1, calculate Spearman's rank correlation coefficient (r) for all possible pairs of individual miRNA measured in step 1 in all bodily fluid samples. Then select as potential biomarker pairs of miRNA with a high positive correlation (r≥0.8), compare a ratio of miRNA concentrations in two subject cohorts for each selected miRNA pair and determine a miRNA pair as a suitable biomarker if this pair differentiates two subject cohorts with a statistically significant P-value.

Selection of miRNAs for biomarker pairs is an important step in developing screening, diagnostic and monitoring tests based on analysis of cell-free circulating miRNAs in bodily fluids. The present invention addresses this issue by providing the following methods for selection of effective biomarker pairs.

In one embodiment, the invention provides a method for selecting a biomarker miRNA pair for diagnosis and/or monitoring of a pathology, said method comprising the following steps:

(a) selecting at least four miRNAs known to be enriched in an organ affected by the pathology;

(b) measuring the level of each miRNA selected in step (a) in bodily fluid samples from two subject cohorts;

(c) calculating the mean level of each miRNA measured in step (b);

(d) calculating the difference between the mean miRNA levels calculated in step (c);

(e) comparing the differences between the mean miRNA levels calculated in step (d) between all studied miRNAs and selecting as potential biomarker pairs those miRNA pairs for which the difference calculated in step (d) for one miRNA is at least 1.5 times the difference calculated for the other miRNA;

(f) calculating Spearman's rank correlation coefficient (r) for each potential biomarker miRNA pair selected in step (e), and (g) identifying the miRNA pair as a suitable biomarker pair for diagnosis and/or monitoring of said pathology if its (r) value calculated in step (f) is at least 0.8.

In another embodiment, the invention provides a method for selecting a biomarker miRNA pair for diagnosis and/or monitoring of a pathology, said method comprising the following steps:

(a) selecting at least four miRNAs known to be enriched in an organ affected by the pathology;

(b) measuring the level of each miRNA selected in step (a) in bodily fluid samples from two subject cohorts;

(c) calculating Spearman's rank correlation coefficient (r) for all possible pairs of individual miRNAs measured in step (b);

(d) selecting as potential biomarker pairs those miRNA pairs which have the (r) value calculated in step (c) of at least 0.8;

(e) calculating the mean level of each miRNA selected in step (d);

(f) calculating the difference between the mean miRNA levels calculated in step (e);

(g) identifying a miRNA pair as a suitable biomarker pair for diagnosis and/or monitoring of said pathology if the difference calculated in step (f) for one miRNA is at least 1.5 times the difference calculated for the other miRNA.

In a further embodiment, the invention provides a method for selecting a biomarker miRNA pair for diagnosis and/or monitoring of a pathology, said method comprising the following steps:

(a) selecting at least four miRNAs known to be enriched in an organ affected by the pathology;

(b) measuring the level of each miRNA selected in step (a) in bodily fluid samples from two subject cohorts;

(c) calculating Spearman's rank correlation coefficient (r) for all possible pairs of individual miRNAs measured in step (b);

(d) selecting as potential biomarker pairs those miRNA pairs which have the (r) value calculated in step (c) of at least 0.8;

(e) calculating P-value of two subject cohorts separation for each miRNA pair selected in step (d), and (f) identifying a miRNA pair as a suitable biomarker pair for diagnosis and/or monitoring of said pathology if this pair differentiates two subject cohorts with a statistically significant P-value.

In another embodiment, the invention provides a computer-implemented method for selecting a biomarker miRNA pair for diagnosis and/or monitoring of a pathology, said method comprising the following steps:

(a) selecting a group of miRNAs known to be enriched in an organ affected by the pathology;

(b) measuring the level of each miRNA selected in step (a) in bodily fluid samples from two subject cohorts;

(c) electronically calculating the mean level of each miRNA measured in step (b);

(d) electronically calculating a difference between the mean miRNA levels calculated in step (c);

(e) selecting from the group of measured miRNAs a set of potential miRNA pairs each comprising a first miRNA and a second miRNA, wherein the calculated difference in the mean level in step (d) of the first miRNA is at least 1.5 times the calculated difference in the mean level of the second miRNA;

(f) electronically calculating the Spearman's rank correlation coefficient (r) for each potential miRNA pair selected in (e);

(g) selecting from the set of potential miRNA pairs those miRNA pairs, which are suitable for the diagnosis and/or monitoring of the pathology, wherein the (r) value calculated in step (f) is at least 0.8, and (h) displaying all or part of the miRNA pairs selected in step (g).

In yet another embodiment, the invention provides a computer-implemented method for selecting a biomarker miRNA pair for diagnosis and/or monitoring of a pathology, said method comprising the following steps:

(a) selecting a group of miRNAs known to be enriched in an organ affected by the pathology;

(b) measuring the level of each miRNA selected in step (a) in bodily fluid samples from two subject cohorts;

(c) electronically calculating the Spearman's rank correlation coefficient (r) for all possible pairs of individual miRNAs measured in step (b);

(d) selecting from the group of measured miRNAs a set of potential biomarker miRNA pairs, wherein the (r) value calculated in step (c) is at least 0.8;

(e) electronically calculating the mean level of each miRNA selected in step (d);

(f) electronically calculating the difference between the mean miRNA levels calculated in step (e);

(g) selecting from the group of measured miRNAs a set of suitable miRNA biomarker pairs each comprising a first miRNA and a second miRNA, wherein for each suitable biomarker miRNA pair, the calculated difference in the mean level in step (f) of the first miRNA is at least 1.5 times the calculated difference in the mean level of the second miRNA, and (h) displaying all or part of the suitable biomarker miRNA pairs selected in step (g). In a further embodiment, the invention provides a computer-implemented method for selecting a biomarker miRNA pair for diagnosis and/or monitoring of a pathology, said method comprising the following steps:

(a) selecting a group of miRNAs known to be enriched in an organ affected by the pathology;

(b) measuring the level of each miRNA selected in step (a) in bodily fluid samples from two subject cohorts;

(c) electronically calculating the Spearman's rank correlation coefficient (r) of the levels measured in step (b) for all possible pairs of individual miRNAs;

(d) selecting from the group of measured miRNAs a set of potential biomarker miRNA pairs, wherein the (r) value calculated in step (c) is at least 0.8;

(e) electronically calculating P-value of two subject cohorts separation for each miRNA pair selected in step (d);

(f) selecting a miRNA pair as a suitable biomarker pair for diagnosis and/or monitoring of said pathology if this miRNA pair differentiates two subject cohorts with a statistically significant P-value, and (g) displaying all or part of the suitable biomarker miRNA pairs selected in step (f).

Non-limiting examples of the methods which can be used to measure miRNA level in any of the above methods of the invention include, e.g., RT-PCR-based methods, miRNA array-based methods, new generation sequencing, and hybridization.

Non-limiting examples of the bodily fluid samples which can be used in any of the above methods of the invention include, e.g., plasma, serum, urine, and saliva.

In any of the above methods of the invention, the subjects can be, e.g., humans or experimental animals.

In any of the above methods of the invention, any two cohorts can be compared. Non-limiting examples of such cohorts include, e.g., pathology versus control [e.g., age, gender, and/or race/ethnicity-matched healthy subjects], one pathology of the organ versus another pathology of the same organ, two age groups, males versus females [e.g., age and/or race/ethnicity-matched], two different ethnic or racial groups [e.g., age and/or gender-matched], etc.).

Spearman's correlation algorithm used in the methods of the invention (Graham J. Borradaile. Statistics of Earth Science Data, Springer, 2003, p. 159).

A minimal number of samples sufficient for obtaining a statistically significant difference between two cohorts in the above methods of the invention can be calculated by a standard formula for case-control study (see, e.g. Eng J. Radiology 2003, 227:309-313).

In the methods of the invention, a statistically significant P-value can be calculated using any method known in the art. Non-limiting examples of such methods are Student's t-test (for samples with normal distribution) and Mann-Whitney test (for samples with non-random distribution) (Mann and Whitney, Annals Math Stat. 1947, 18: 50-60). P-value >0.05 is usually accepted as statistically significant. If numerous potential biomarkers are tested Bonferroni correction can be applied.

Kits of the Invention

In conjunction with the above diagnostic, monitoring and screening methods, the present invention provides various kits comprising one or more primer and/or probe sets specific for the detection of the biomarker miRNA pairs.

Such kits can further include primer and/or probe sets specific for the detection of additional normalizer miRNAs.

Such kits can be useful for direct miRNA detection in bodily fluid samples isolated from patients or can be used on purified total RNA or miRNA samples.

A kit of the invention can also provide reagents for primer extension and amplification reactions. For example, in some embodiments, the kit may further include one or more of the following components: a reverse transcriptase enzyme, a DNA polymerase enzyme (such as, e.g., a thermostable DNA polymerase), a polymerase chain reaction buffer, a reverse transcription buffer, and deoxynucleoside triphosphates (dNTPs). Alternatively (or in addition), a kit can include reagents for performing a hybridization assay. The detecting agents can include nucleotide analogs and/or a labeling moiety, e.g., directly detectable moiety such as a fluorophore (fluorochrome) or a radioactive isotope, or indirectly detectable moiety, such as a member of a binding pair, such as biotin, or an enzyme capable of catalyzing a non-soluble colorimetric or luminometric reaction. In addition, the kit may further include at least one container containing reagents for detection of electrophoresed nucleic acids. Such reagents include those which directly detect nucleic acids, such as fluorescent intercalating agent or silver staining reagents, or those reagents directed at detecting labeled nucleic acids, such as, but not limited to, ECL reagents. A kit can further include miRNA isolation or purification means as well as positive and negative controls. A kit can also include a notice associated therewith in a form prescribed by a governmental agency regulating the manufacture, use or sale of diagnostic kits. Detailed instructions for use, storage and troubleshooting may also be provided with the kit. A kit can also be optionally provided in a suitable housing that is preferably useful for robotic handling in a high throughput setting.

The components of the kit may be provided as dried powder(s). When reagents and/or components are provided as a dry powder, the powder can be reconstituted by the addition of a suitable solvent. It is envisioned that the solvent may also be provided in another container. The container will generally include at least one vial, test tube, flask, bottle, syringe, and/or other container means, into which the solvent is placed, optionally aliquoted. The kits may also comprise a second container means for containing a sterile, pharmaceutically acceptable buffer and/or other solvent.

Where there is more than one component in the kit, the kit also will generally contain a second, third, or other additional container into which the additional components may be separately placed. However, various combinations of components may be comprised in a container.

Such kits may also include components that preserve or maintain DNA or RNA, such as reagents that protect against nucleic acid degradation. Such components may be nuclease or RNase-free or protect against RNases, for example. Any of the compositions or reagents described herein may be components in a kit.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1: Selection of miRNAs for Testing

The methods of the instant invention are based on the use of miRNAs enriched in different brain areas as numerators and denominators as well as in liver and muscle, which significantly improves test sensitivity and specificity. Table 1 below presents lists of brain-enriched miRNAs, miRNAs enriched in synapses, axons, dendrites and spines ("synapse and/or neurite miRNAs") and miRNAs enriched in different brain areas, liver and muscles.

TABLE 1 miRNAs enriched in organs most affected in subjects with Rett syndrome (brain, different brain areas and neuronal compartments, liver, muscle)

| Organ/region | Enriched miRNAs |
| --- | --- |
| Brain | Let-7a, c, e, 7, 9, 19a, b (?), 92b (?), 96, 98, 99a, b, 103, 105, 106a (?), 107, 124a, 125a, 125b, 126 (?), 127, 128a, 129, 132, 134, 135a, 137, 138, 139, 149, 151 (?), 153, 154, 181a, 181b, 181c, 182 (?), 183 (?), 184, 190 (?), 195 (?), 197, 204, 211, 212, 213, 218, 219(-2-3p)(-5p), 221 (?), 222 (?), 299-3p, 299-5p, 323-3p, 324-5p, 326, 328, 329, 330, 331, 335-5p, 337, 338-5p, 340, 342, 346, 361 (?), 363 (?), 369-3p, 369-5p, 370, 377, 379, 381, 382, 383, 409-3p, 410, 411, 423-5p (?), 425, 432, 433-5p, 453, 485-3p, 485-5p, 487a, b, 488, 491-5p, 494, 495, 496, 497 (?), 504, 522, 539, 541 (?), 543, 544, 551b (?), 572, 577, 584, 592, 598, 625, 628, 652(?), 654, 655, 656, 668, 671, 672, 708, 744, 758, 769-3p, -5p, 770, 873, 874, 876-3p, 885-3p, -5p, 889, 935, 939(?), 941, 1193, 1197, 9*, let-7d*, 7*, 99b*, 1224-3p, -5p, 1225-3p (?), 1237, 125b-2*, 129*, 138-2*, 340*, 380*, 411*, 425*, 488*, 744* |
| Brain, enriched in synapses, axons, dendrites, spines | Let-7e, 7, 9, 98, 99a, 100 (?), 124a, 125a, 125b, 128a, 129, 132, 134, 135a, 137, 138, 154, 182, 183, 204, 213, 218, 323-3p, 329, 337, 342-3p, 369-3p, 369-5p, 370, 381, 382, 409-3p, 425, 433-5p, 483-3p, 485-5p, 487b, 491-5p, 494, 495, 496, 541, 543, 656, 668, 874, 889, 935, 939, 9*, 181a-1* (axon) |
| Cortex | 9, 98, 103, 107, 124a, 125a, 125b, 126 (?), 128a, 129, 132, 134, 138, 149, 154, 181a, b, c, d, 197, 212, 213, 222, 323, 330-3p, 338-3p, -5p, 342, 370, 381, 382, 411, 425, 433, 491-5p, 539, 885 |
| Hippocampus | 9, 96, 99a, 103, 107, 124a, 125b, 126 (?), 128a, 132, 134, 137, 138, 153, 181a, 181b, c, 184, 197, 212 (?), 218, 219, 221, 222, 324-5p, 328, 330 (?), 331, 335-5p, 338, 369-3p, 379, 381, 382, 383, 411, 425, 433-5p, 485-5p, 488, 491-5p, 574, 874, 885 (?) |
| Hypothalamus | Let-7a, b, c, 103, 124a, 125a, 128a, 132, 136, 138, 212, 338, 451 |
| Cerebellum | 9, 98, 103, 124a, 125b, 128 (?), 132, 134, 137, 138, 181a, 181b, 181c, 204, 212, 213, 218, 338, 381, 382 (?), 425, 432, 489, 592, 874, 885 |
| Amygdala | 103, 134, 138, 182, 183, 222, 323-3p, 369, 381, 382 |
| Spinal cord | 218, 219, 338, 451, 486 |
| Pituitary gland | Let-7c, 7, 9, 92a, b, 96, 99a, b, 103, 107, 125a, b, 127, 128, 132, 134, 135a, 154, 181a-c, 182, 183, 184, 195, 197, 200a, b, c (?), 204, 212, 213, 218, 322 (?), 323, 324, 328, 329, 335-5p, 369, 370, 375, 377, 379, 381, 410, 411, 432, 433, 487b, 491, 494, 508, 514, 539, 542 (?), 603 (?), 618, 628, 652, 663 (?), 665, 885, 890 (?) |
| Midbrain, Substantia nigra | Let-7a, b, c, d, e, 9, 98, 99a, b, 100, 107, 125a, b (?), 126, 127-3p, 129-3p, 134, 138, 149, 181a, 197, 204, 323, 329, 338, 340, 340*, 379, 383, 410, 424, 425, 432, 433, 487a, b, 539, 744 (?), 760, 9*, 99b*, 129*; |
| Medulla oblongata | 10a, b, 34a, 451 (all not brain-enriched), 219, 338 |
| Liver | 30e-3p, 122a, 130b, 136, 148a, 192 (?), 194, 362-3p, 376c, 455-3p, 483-5p, 505, 518b, 571, 616, 622, 801, 885-5p, 17*, 30d*, 194* |
| Muscle | 1, 22, 95, 133a, 133b, 140, 206, 486-5p; 208, 208b, 499 |

(?) - Insufficient or contradictory data.

Tested miRNAs were initially selected by the present inventors based on literature data on their enrichment in brain compartments and presence in neurites (i.e., axons and/or dendrites and/or spines) and/or synapses (Hua et al. BMC Genomics. 2009; 10: 214; Liang et al. BMC Genomics. 2007; 8:166; Landgraf et al. Cell. 2007; 129: 1401-1414;

Lee et al. RNA. 2008; 14: 35-42; Schratt et al. Nature. 2006; 439: 283-289; Lugli et al. J. Neurochem. 2008; 106: 650-661; Bicker and Schratt. J. Cell Mol. Med. 2008; 12: 1466-1476; Smalheiser and Lugli. Neuromolecular Med. 2009; 11: 133-140; Rajasethupathy. Neuron. 2009; 63: 714-716; Kye. RNA. 2007; 13: 1224-1234; Yu et al. Exp. Cell Res. 2008; 314: 2618-2633; Cougot et al. J. Neurosci. 2008; 28: 13793-13804; Kawahara. Brain Nerve. 2008; 60: 1437-1444; Schratt. Rev. Neurosci. 2009; 10: 842-849; Pichardo-Casas et al. Brain Research. 2012; 1436: 20-33) as well as on their suggested involvement in neurite- and synapse-associated processes (the miR-Ontology Data Base: ferrolab.dmi.unict.it/miro/; Landgraf et al., Cell, 2007, 129:1401-1414; Liang et al., BMC Genomics, 2007, 8:166; Jovičić, J. Neurosci., 2013, 33:5127-5137; Ludwig et al., Nucleic Acids Res., 2016, 44:3865-3877; Martini et al., PLoS One, 2014, 9:e89755; Penso-Dolfin et al., PLoS One, 2016, 11:e0153453). Similarly liver- and muscle-enriched miRNAs were selected. Ubiquitous apoptosis-related miR-16 was also tested as a potential denominator. miR-146a and miR-155 were tested due their involvement in inflammatory pathways. Then the present inventors analyzed literature and their own data to find out which miRNAs are detectable in plasma. Due to limited amount of plasma, 8 different miRNAs were analyzed in the animal and 19 different miRNAs were tested in human studies (Table 2).

Example 2: Quantitative Analysis

Mann-Whitney U-test was used to evaluate significance of differentiation of any two patient groups by various biomarker miRNA pairs. Bonferroni correction was applied for estimating significant P-values. In all experiments (differentiation of RTT mouse model from wild type control) 8 miRNAs were tested, thus P-value<0.002 (calculated as 0.05/28; 28 here indicates the total number of miRNA pairs examined) was considered significant. A standard formula for a case-control study (Eng J. Radiology. 2003; 227:309-313) was applied for estimating the sample size required to produce statistical power 0.90. Two approaches for comparison of two cohorts, namely ratios of two miRNA concentrations and described above probability-based method, were used and gave similar results, although the latter is much more convenient for combining several miRNA pairs or other biomarkers.

Example 3: Differentiation of Mecp2$^{tm1.1Jae}$ Mouse RTT Model from Wild Type Controls Two mouse models were used, namely Mecp2$^{tm1.1Jae}$ and Mecp2$^{tm1.1Bird}$. Both models are male mice (Null) with nonfunctional Mecp2 due to deletion of exon 3 in Mecp2$^{tm1.1Jae}$ (Guy, J., Hendrich, B., Holmes, M., Martin, J. E. and Bird, A. (2001). A mouse Mecp2-null mutation causes neurological symptoms that mimic Rett syndrome. Nat. Genet. 27, 322-326) or exon 3-4 in Mecp2$^{tm1.1Bird}$ (Chen, R. Z., Akbarian, S., Tudor, M. and Jaenisch, R.

TABLE 2 miRNAs used in the study

| # | miRNA | Brain enrichment | Enriched in synapses | Animal study | Human study | Comments |
|---|---|---|---|---|---|---|
| 1 | Let-7b-5p | Ubiquitous | | | + | Inhibits Mecp2 expression |
| 2 | miR-16 | Ubiquitous | | + | + | |
| 3 | miR-29b-3p | PG (not brain-enriched) | | | + | |
| 4 | miR-107 | FC, PG, Hip, MB | + | + | + | |
| 5 | miR-122 | Liver-enriched | | | + | |
| 6 | miR-125b | FC, MB, PG, Hip | + | | + | |
| 7 | miR-132-3p | PG, Hip | + | + | + | Inhibits Mecp2 expression |
| 8 | miR-134 | MB, Hip, PG | + | | + | |
| 9 | miR-146a | Inflammatory | | | + | |
| 10 | miR-155 | Inflammatory | | | + | Inhibits Mecp2 expression |
| 11 | miR-181a-5p | MB, FC | + | | + | Inhibits Mecp2 expression |
| 12 | miR-206 | Muscle, Cer | | | + | |
| 13 | miR-323-3p | FC, Hip, MB | + | + | + | |
| 14 | miR-335-5p | PG, Hip | | + | + | |
| 15 | miR-370 | PG, FC | + | + | − | |
| 16 | miR-409-3p | Hip | + | | + | |
| 17 | miR-411-5p | PG, Hip, FC | | + | + | |
| 18 | miR-432-5p | PG, MB, Cer | | | + | Inhibits Mecp2 expression |
| 19 | miR-433-3p | PG, MB | + | | + | |
| 20 | miR-491-5p | MB, FC | + | + | + | |

Cer—Cerebellum;
FC—Frontal Cortex;
Hip—Hippocampus;
MB—Midbrain;
PG—Pituitary Gland (2001). Deficiency of methyl-CpG binding protein-2 in CNS neurons results in a Rett-like phenotype in mice. Nat. Genet. 27, 327-331), respectively. Since the total amount of plasma that can be obtained from a mouse is relatively low, 8 miRNAs expressed in different brain regions were tested (see Table 2, above).

0.2 ml plasma samples were obtained from 11 Mecp2$^{tm1.1Jae}$ mice and 9 wild type controls of the same age. Concentrations of miRNAs in plasma were analyzed using RT-qPCR with primers and probes for each individual miRNA (Life Technologies). The amount of RNA equivalent to 25 of plasma were taken in each RT reaction, and the amount of miRNA (cDNA) equivalent to 2 plasma was taken into final PCR. The results obtained for each miRNA were converted into Relative Concentration (RC) of miRNA according to the ABI protocol ($2^{-\Delta Ct}$), normalized per potential normalizer miRNA, and this ratio was compared with respective control values. The biomarker miRNA pairs were selected as described above.

Figure 2A:
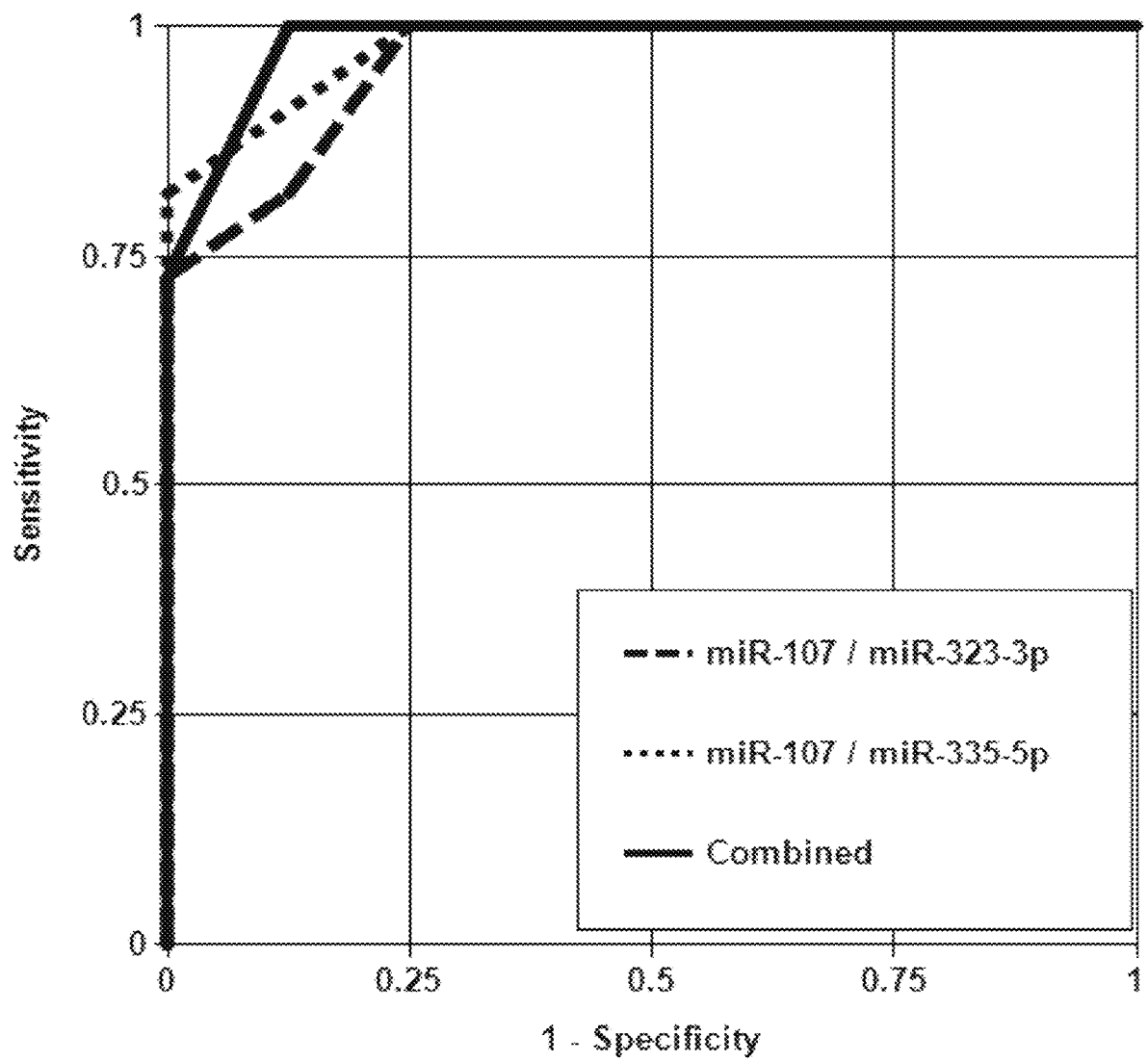
FIGS. 2A-2B are graphs presenting ROC curves for differentiation between wild type and Mecp2$^{tm1.1Jae}$ Null mice with miRNA pairs.
Figure 2B:
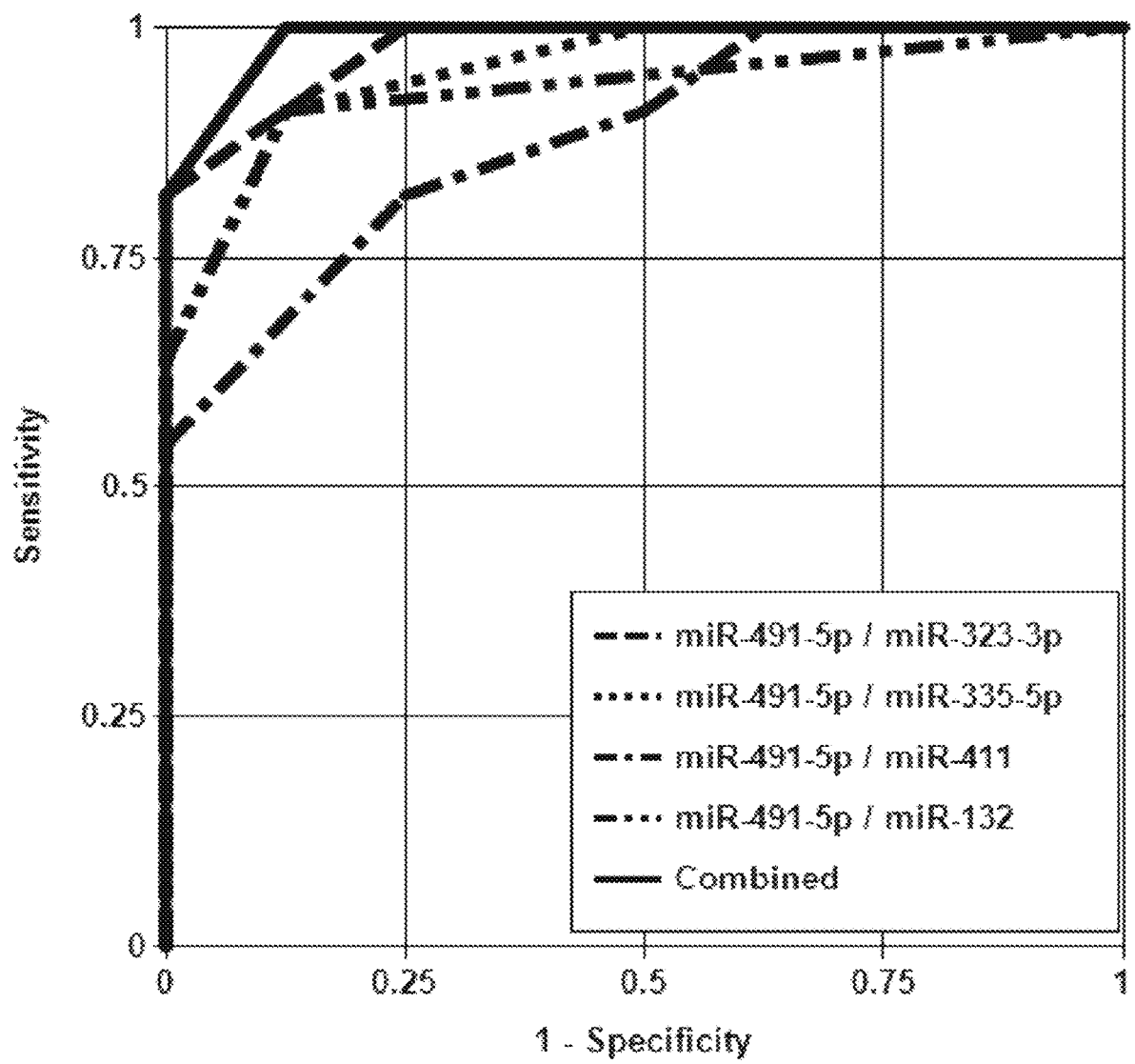
Figure 3A:
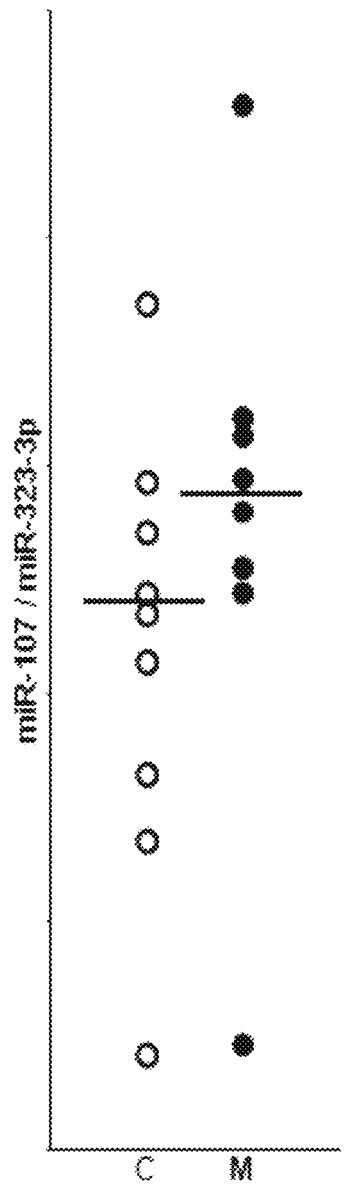
FIGS. 3A-3E are graphs showing ratios of miRNA levels (biomarker miRNA pairs identified in Example 3 for differentiating Mecp2$^{tm1.1Jae}$ Null and wild type mice) in plasma of wild type and Mecp2$^{tm1.1Bird}$ mice. miRNA ratios are presented as log 10 of 2ΔCt. Average for each pair is indicated.
Figure 3B:
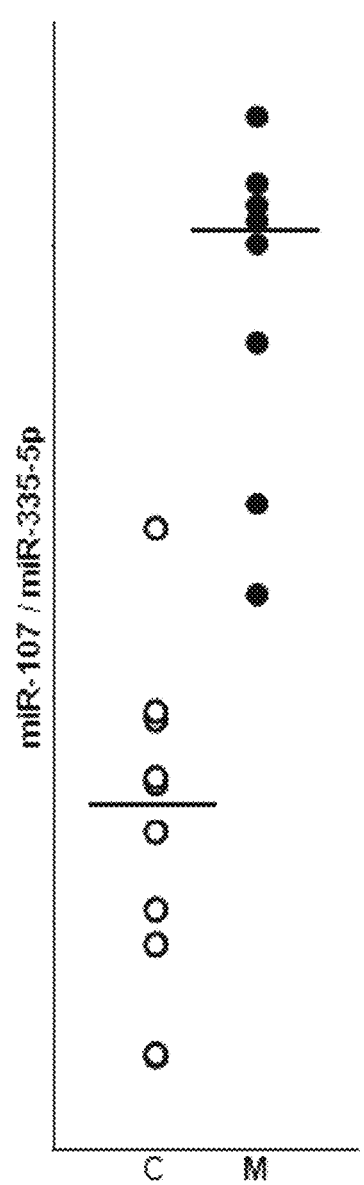
Figure 3C:
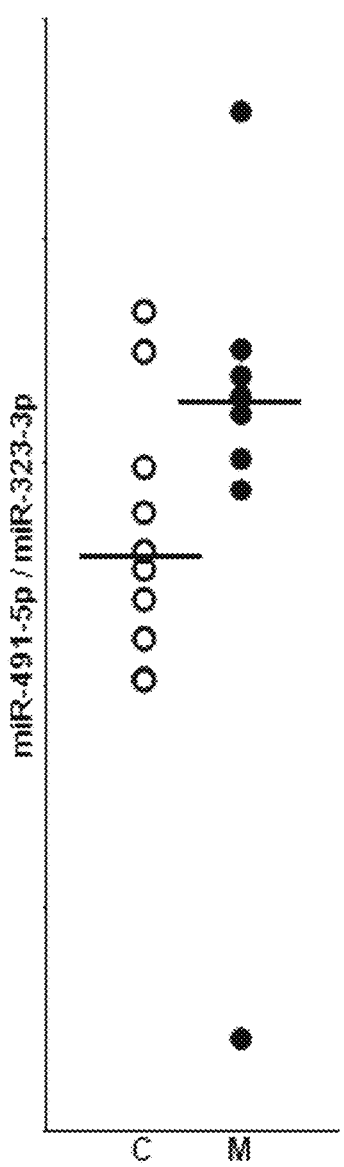
Figure 3D:
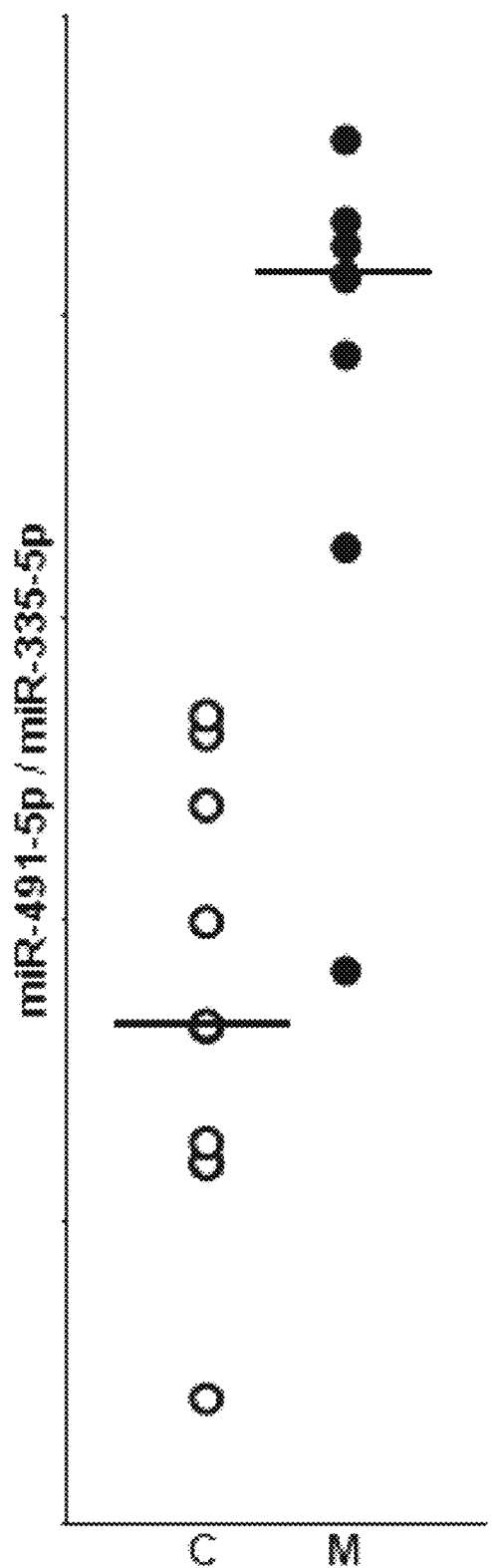
Figure 3E:
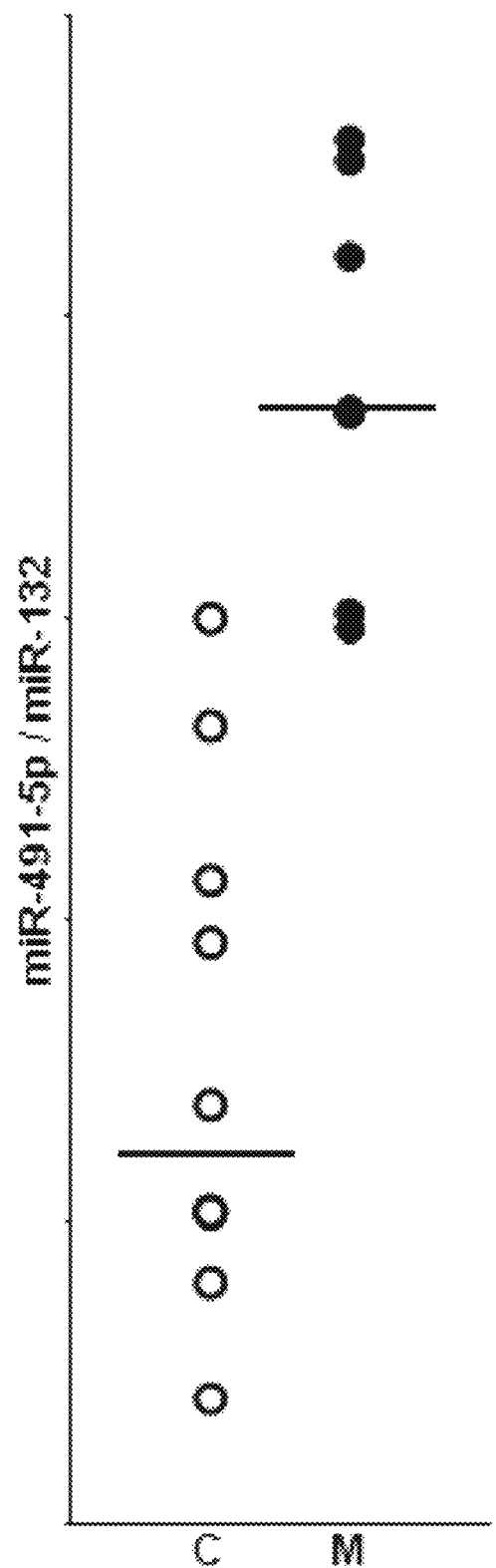
Figure 4E:
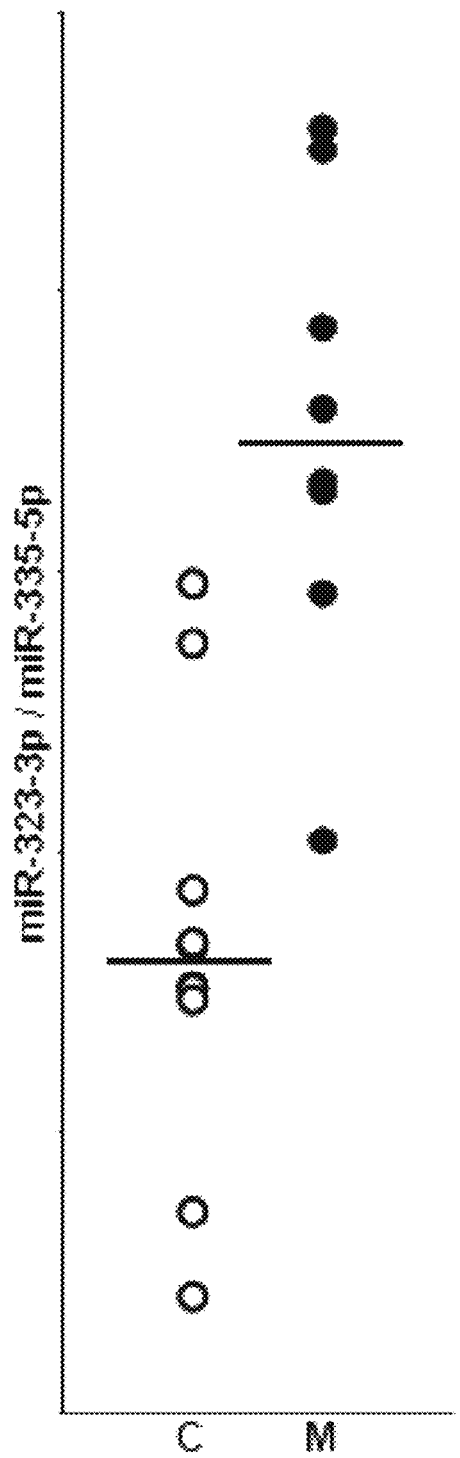
Figure 4F:
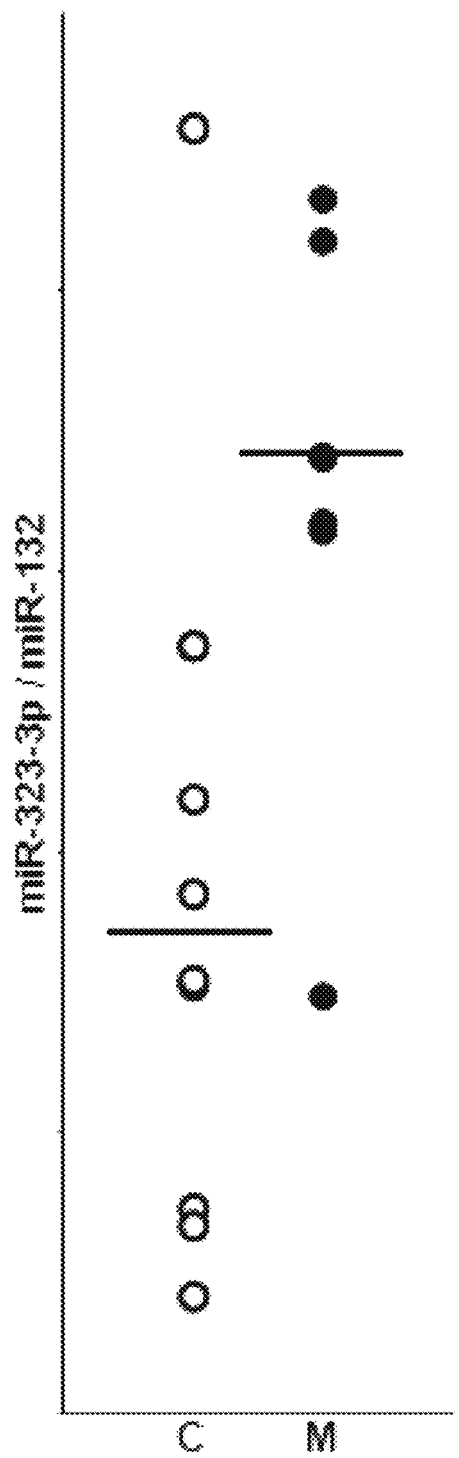
Figure 4G:
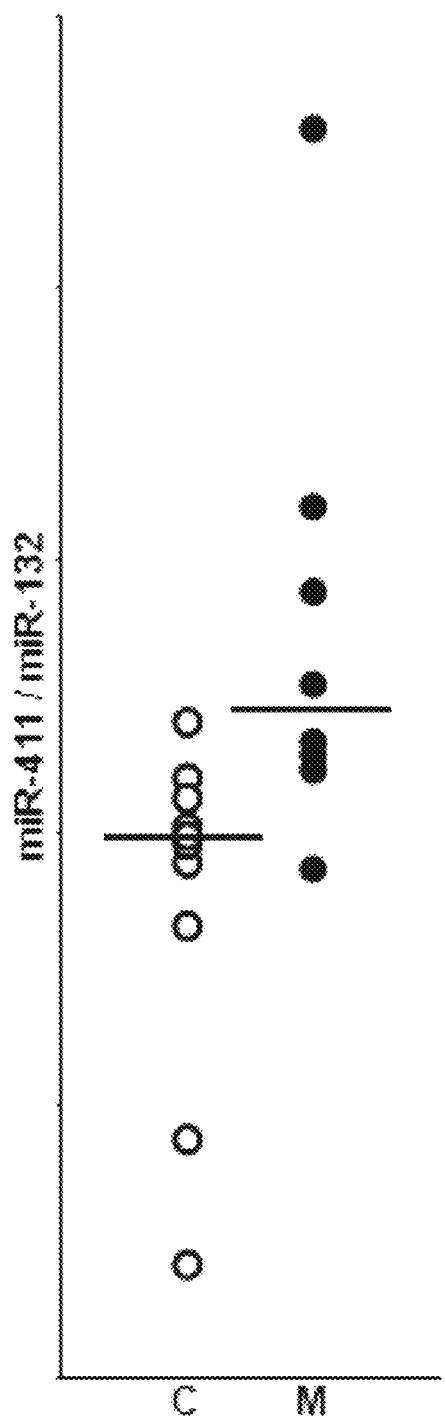
Figure 4H:
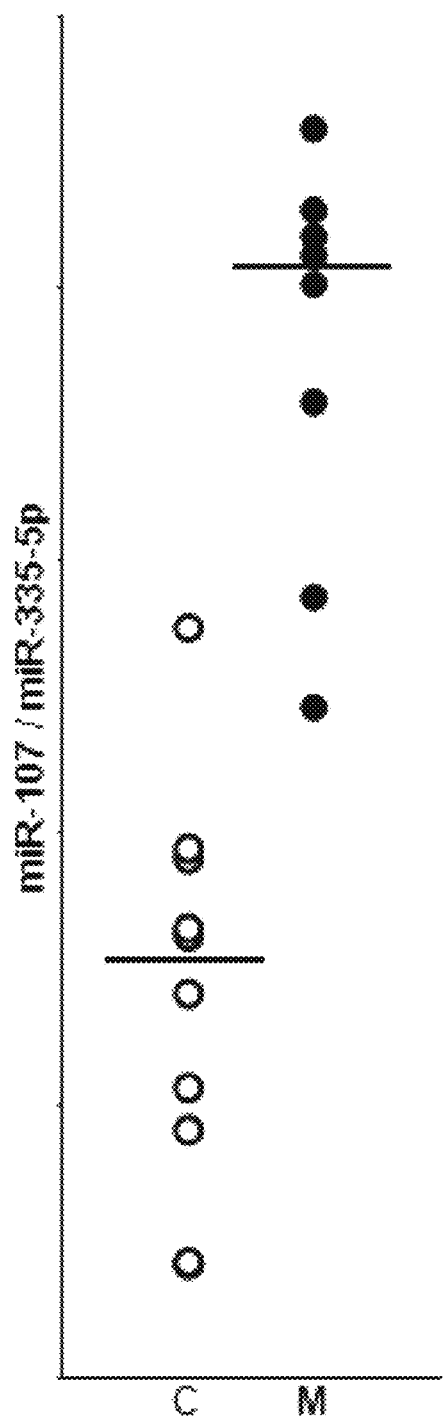

Comparison of brain-enriched miRNA pair ratios in mutant and control mice are presented in FIG. 1. P-values for differentiation of RTT mice model from wild type controls and AUC (Area under ROC curve) for best miRNA pairs are presented in Table 3 and in FIG. 2. miR-107 and miR-491-5p enriched in midbrain and frontal cortex and present in synapses behave as the best numerators, which is in a good agreement with known involvement of these brain regions in the RTT pathology. Hippocampus-enriched miR-132 and miR-335-5p are good denominators. Interestingly, miR-323-3p, whose presence in midbrain and cortex has been described in literature behaves as a good denominator. Most likely miR-323-3p is present in different brain regions and its plasma concentration depends on involvement of these areas in pathology and respective changes in miR-323-3p expression and secretion. Although accuracy for individual miRNA pairs is sufficiently high (up to 0.89), their combination gives even higher accuracy (0.95).

TABLE 3

Differentiation of Mecp2$^{tm1.1Jae}$ Null and control mice by miRNA pairs and their combinations

| miRNA pair | AUC | Sensitivity | Specificity | Accuracy | P-value |
|---|---|---|---|---|---|
| miR-107/miR-323-3p | 0.98 | 0.82 | 1.0 | 0.89 | <0.0002 |
| miR-107/miR-335-5p | 0.96 | 1.0 | 0.75 | 0.89 | <0.0003 |
| Combined | 0.98 | 1.0 | 0.88 | 0.95 | |
| miR-491-5p/miR-323-3p | 0.98 | 0.82 | 1.0 | 0.89 | <0.0002 |
| miR-491-5p/miR-335-5p | 0.95 | 0.91 | 0.88 | 0.89 | <0.0006 |
| miR-491-5p/miR-132 | 0.93 | 0.91 | 0.88 | 0.89 | <0.0025 |
| miR-491-5p/miR-411 | 0.88 | 0.82 | 0.75 | 0.79 | <0.0079 |
| Combined | 0.99 | 1.0 | 0.88 | 0.95 | |

Figure 5A:
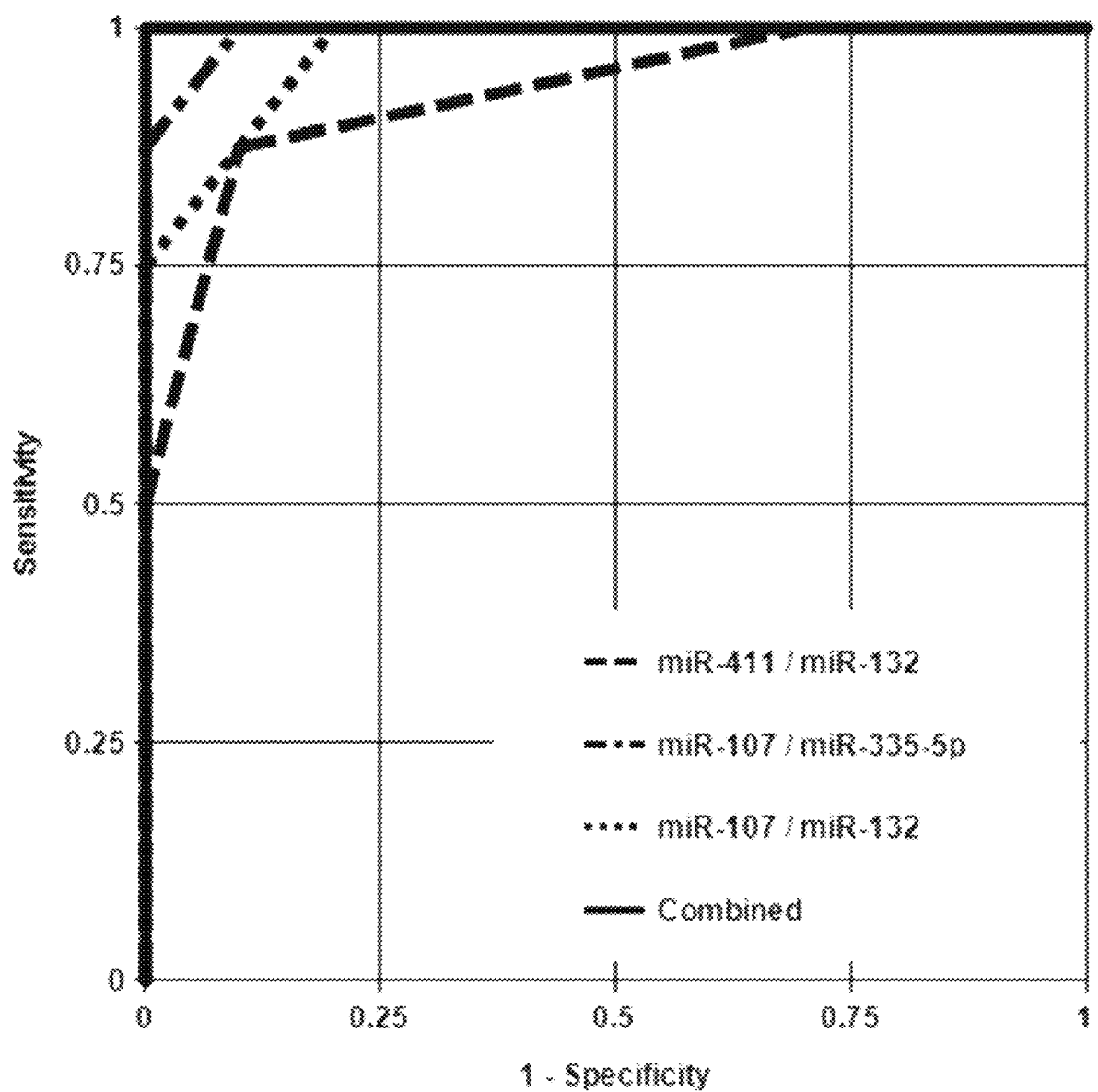
FIGS. 5A-5B are graphs presenting ROC curves for differentiation between wild type and Mecp2$^{tm1.1Bird}$ Null mice with miRNA pairs.
Figure 5B:
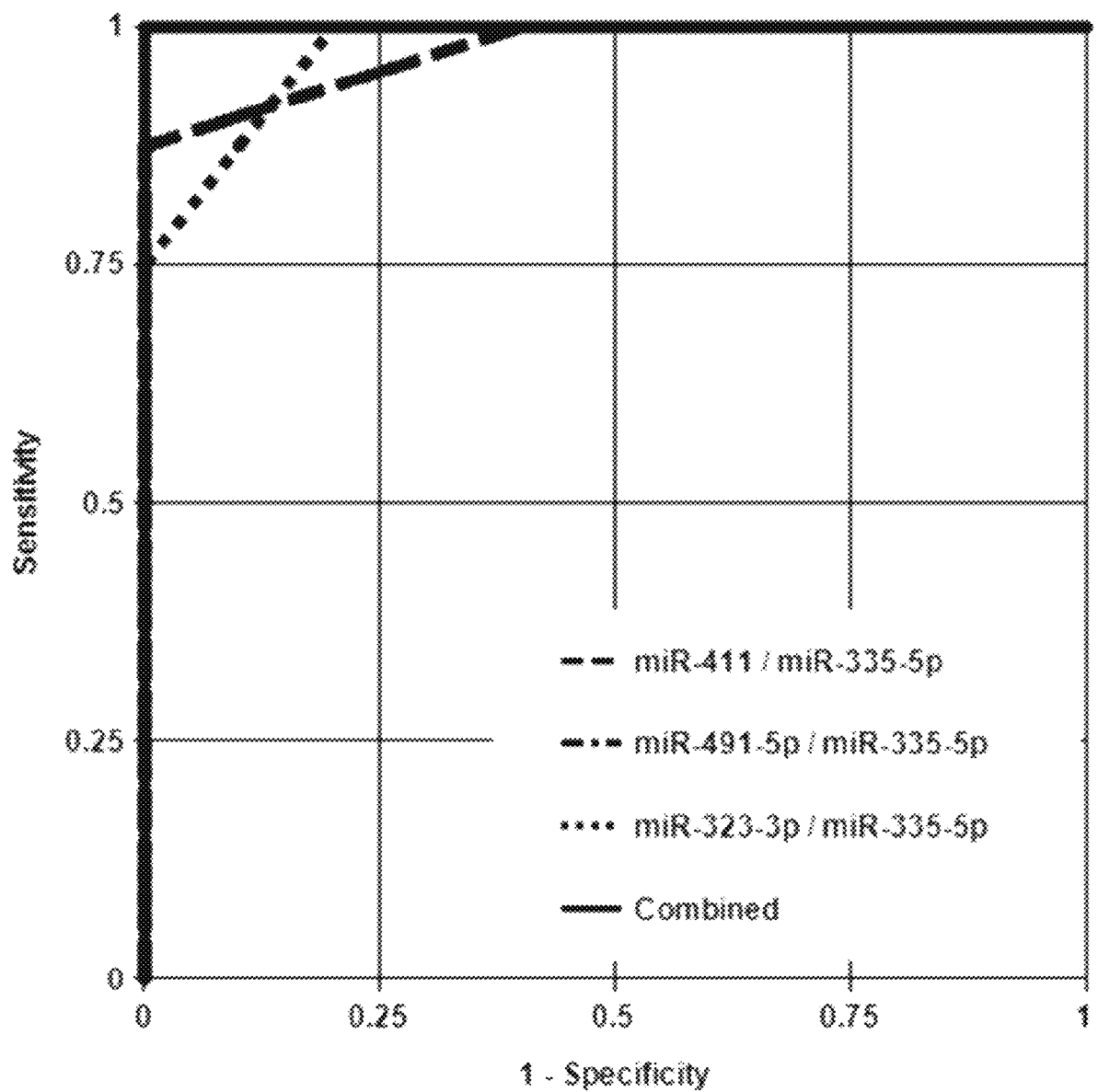

Example 4: Differentiation of Mecp2$^{tm1.1Bird}$ Null Mouse RTT Model from Wild Type Controls 0.2 ml plasma samples were obtained from 8 Mecp2$^{tm1.1Bird}$ mouse and 10 wild type controls of the same age. Same 8 miRNAs were tested and experiments were performed as described above in Example 3. Data obtained are presented in FIGS. 3-5 and Table 4. Again miR-107 and miR-491-5p are very good numerators, while miR-132 and miR-335-5p, enriched in hippocampus are among the best denominators. miR-323-3p is still a good denominator for miR-491-5p but also behaves as a numerator being combined with miR-132 and miR-335-5p, which again agrees with its expression in various brain areas.

TABLE 4

Differentiation of Mecp2$^{tm1.1Bird}$ Null and control mice by miRNA pairs and their combinations (Bold row indicates miRNA pairs common for two RTT mice models).

| miRNA pair | AUC | Sensitivity | Specificity | Accuracy | P-value |
|---|---|---|---|---|---|
| miR-411/miR-132 | 0.93 | 0.88 | 0.9 | 0.89 | <0.0032 |
| miR-107/miR-132 | 0.98 | 0.88 | 0.9 | 0.89 | <0.0002 |
| Combined | 1 | 1 | 1 | 1 | <0.0001 |
| miR-491-5p/miR-335-5p | 0.98 | 0.88 | 1 | 0.94 | <0.0003 |
| miR-491-5p/miR-132 | 0.99 | 0.88 | 1 | 0.94 | <0.0001 |
| Combined | 0.99 | 0.88 | 1 | 0.94 | <0.0001 |
| miR-323-3p/miR-335-5p | 0.98 | 0.75 | 1 | 0.89 | <0.0002 |
| miR-323-3p/miR-132 | 0.91 | 0.88 | 0.9 | 0.89 | <0.0078 |
| Combined | 0.95 | 0.88 | 0.9 | 0.89 | <0.001 |
| miR-323-3p/miR-335-5p | 0.98 | 0.75 | 1 | 0.89 | <0.0002 |
| miR-491-5p/miR-335-5p | 0.98 | 0.88 | 1 | 0.94 | <0.0003 |
| miR-411/miR-335-5p | 0.98 | 0.88 | 1 | 0.94 | <0.0003 |
| Combined | 1 | 1 | 1 | 1 | <0.0001 |

Figure 6F:
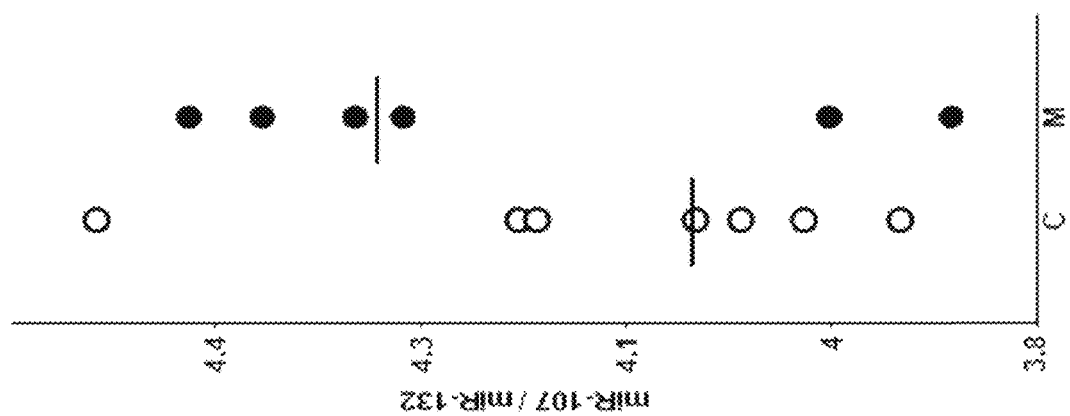
Figure 6E:
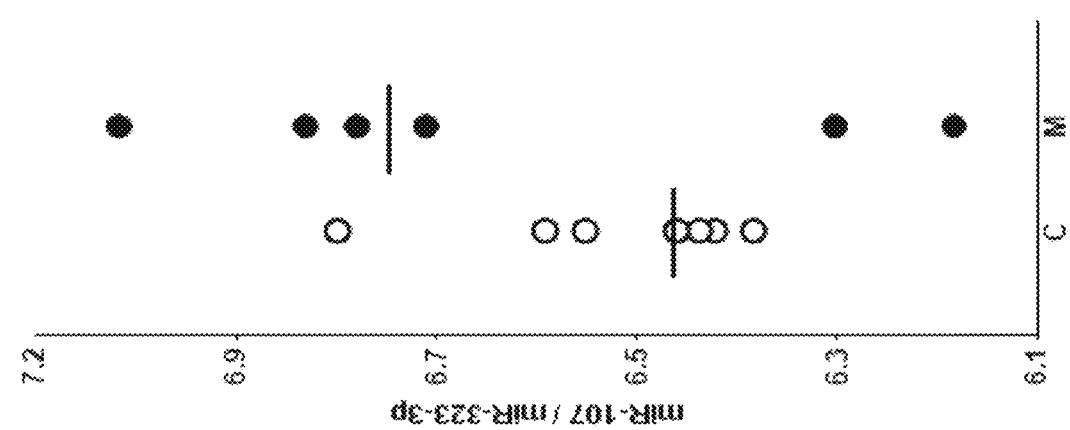
Figure 6D:
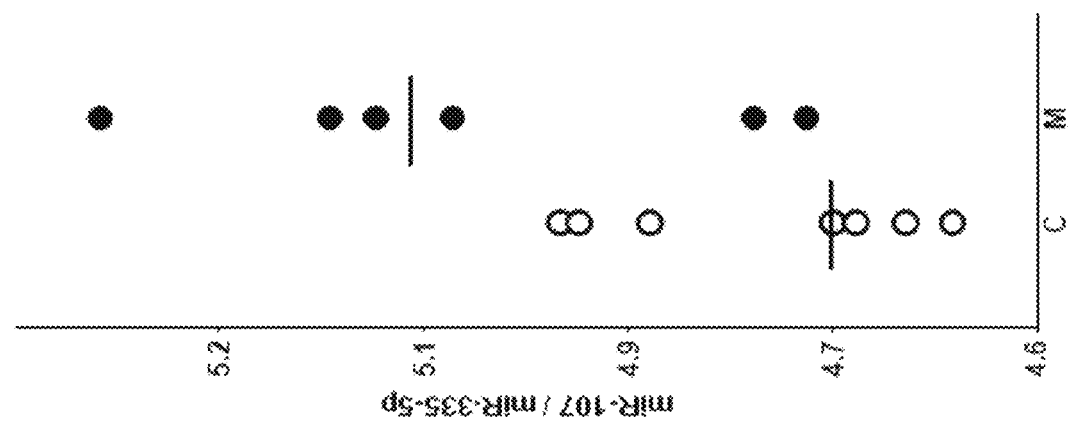
Figure 7A:
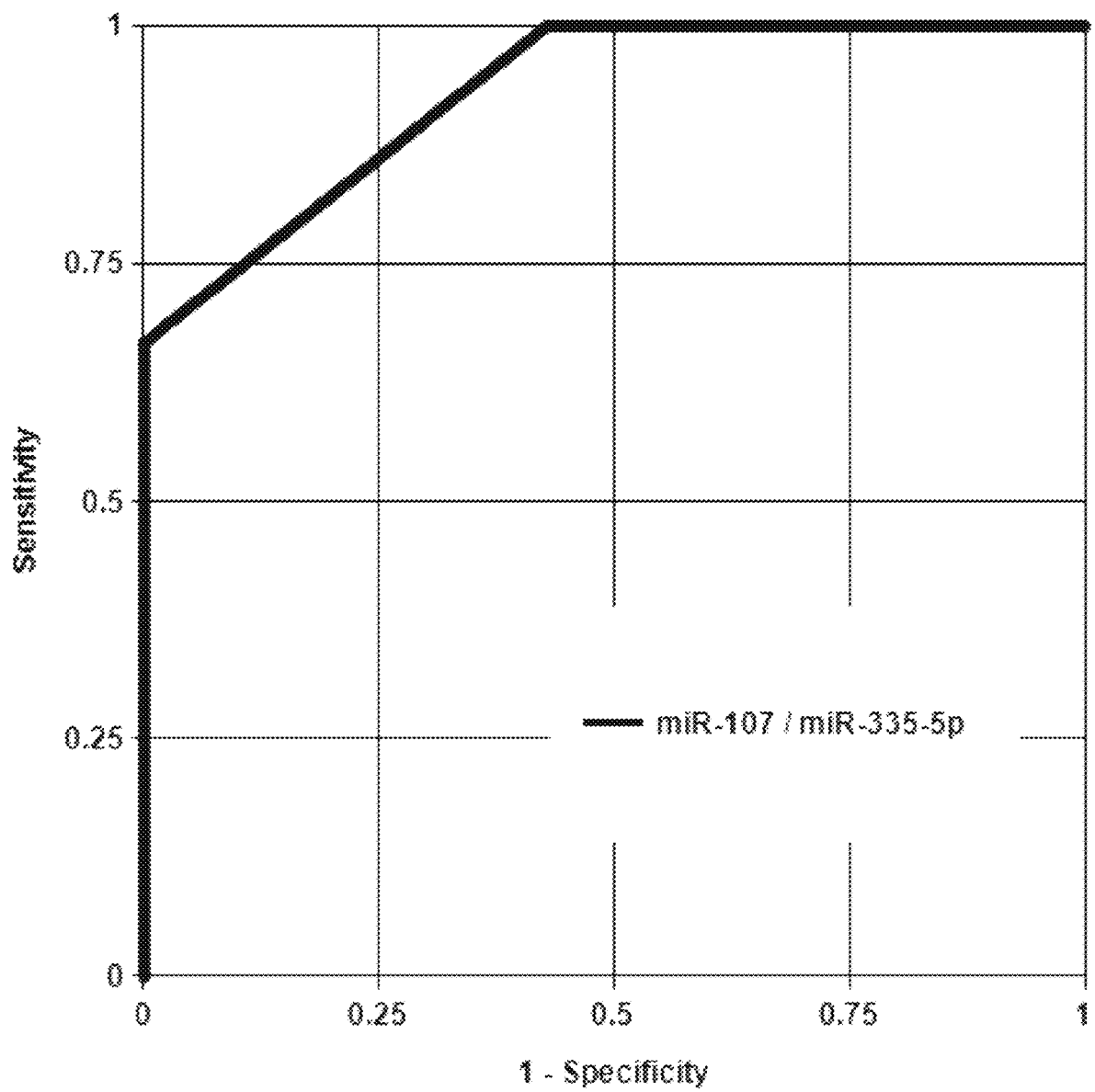
FIGS. 7A-7B are graphs presenting ROC curves for differentiation between wild type and Mecp2$^{tm1.1Jae}$ Het mice with miRNA pairs.
Figure 7B:
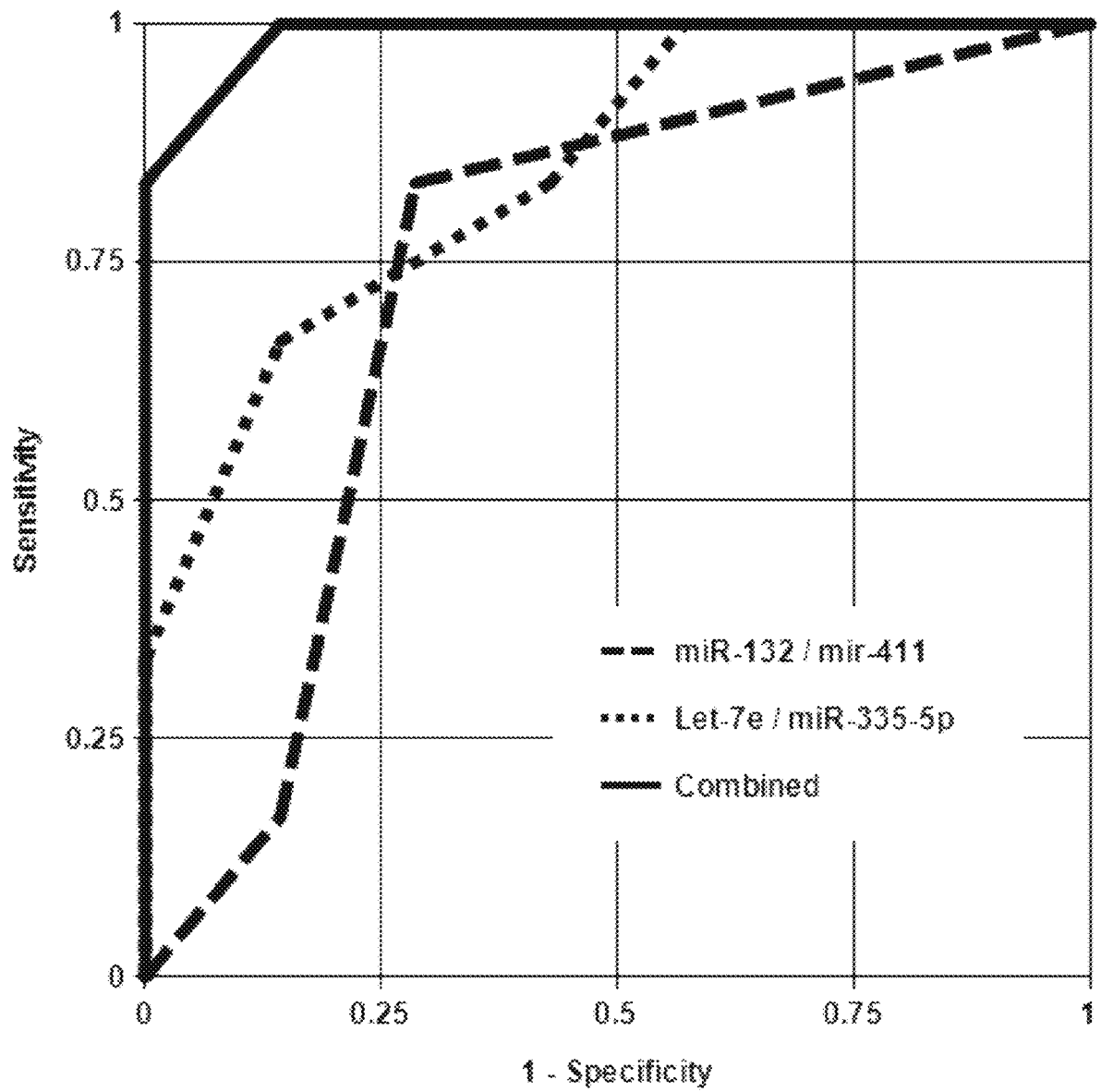
Figure 8D:
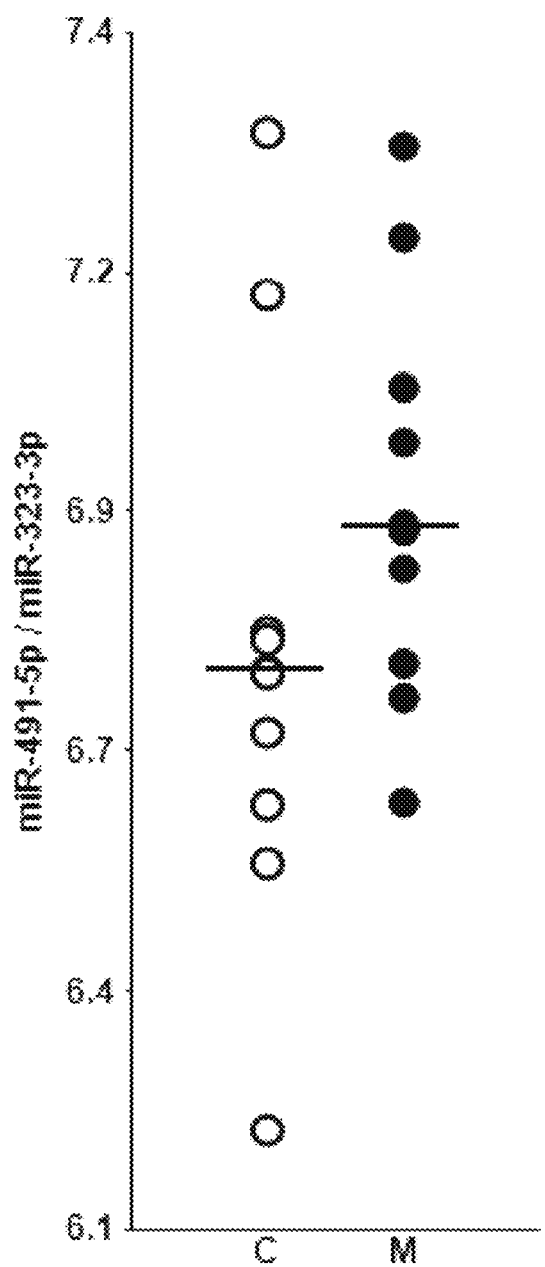
Figure 8E:
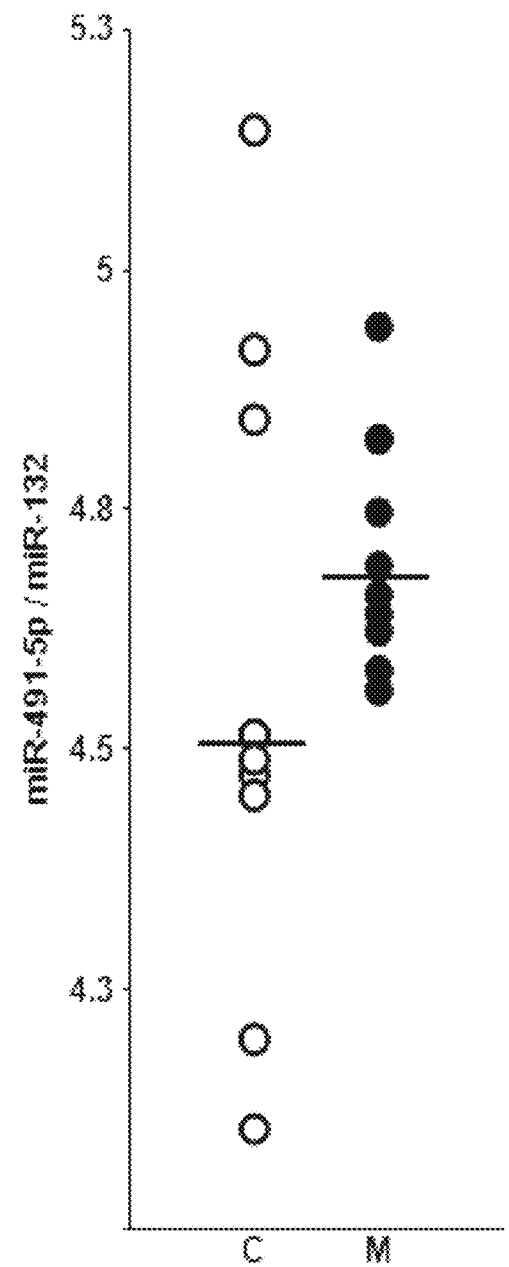
Figure 9:
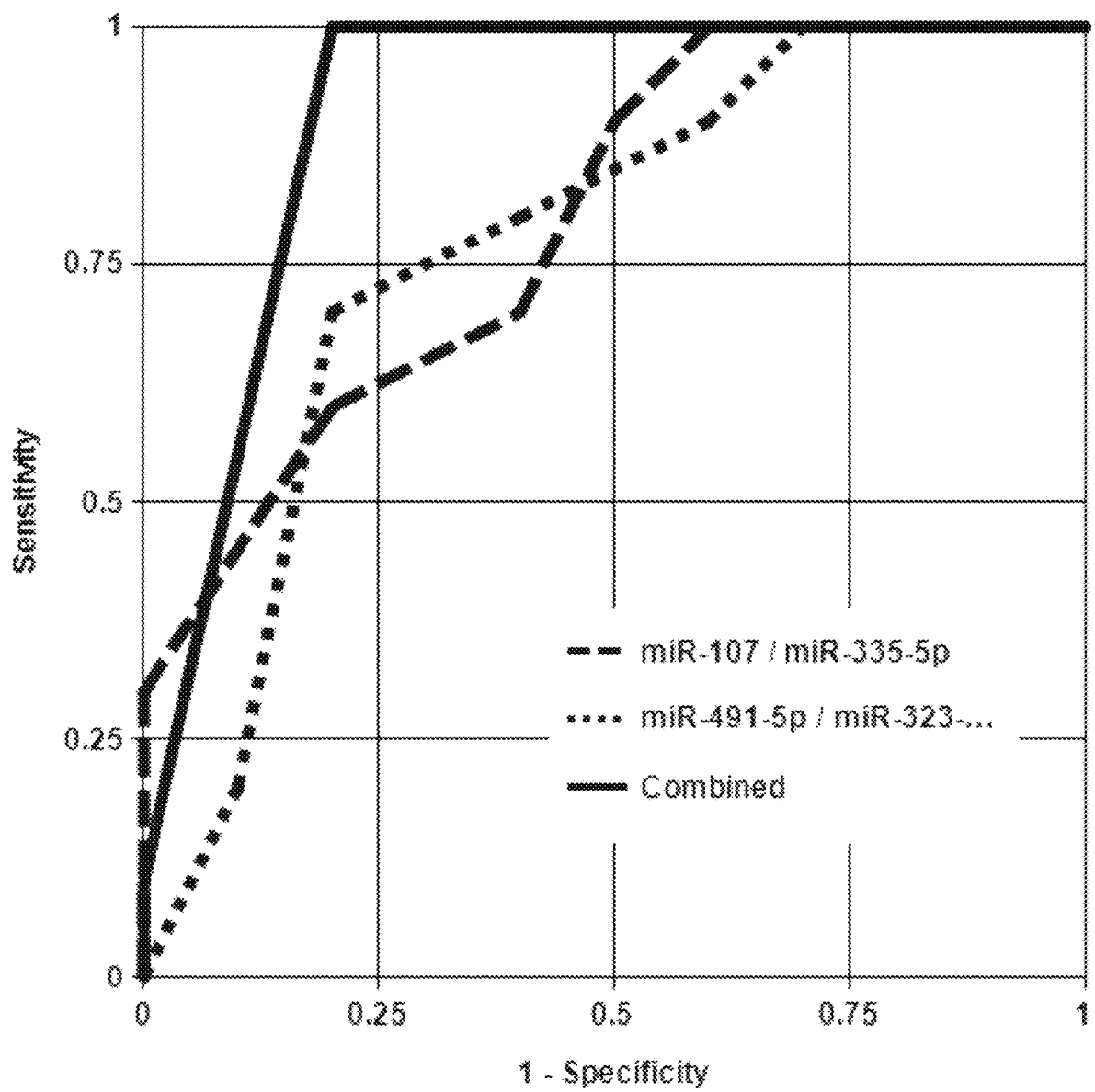
FIG. 9 is a graph presenting ROC curves for differentiation between wild type and Mecp2$^{tm1.1Bird}$ Het mice with miRNA pairs.

Example 5. Differentiation of Mecp2$^{tm1.1Jae}$ Het and Mecp2$^{tm1.1Bird}$ Het Mouse RTT Models from Wild Type Controls The levels of the eight miRNA in two cohorts of female heterozygous (Het) and wild type (Wt) mice: Mecp2$^{tm1.1Jae}$ Het n=6, Wt n=7 (6 months old), and Mecp2$^{tm1.1Bird}$ Het n=10, Wt n=10 (18 weeks old) were compared. The two pairs of mutant and Wt cohorts were tested at different ages, and therefore were analyzed independently. Same 8 miRNAs were tested and experiments were performed as described above in Example 3. FIG. 6 and FIG. 8, respectively, present the data from these two experiments as dot-plots and FIG. 7 and FIG. 9 demonstrate the associated ROC curves. As expected, in Het, the AUC and its associated accuracy representing the ability of miRNA pairs to distinguish mutant from wild type mice, were lower than in Null mice, since female heterozygotes retain some normal MeCP2 expression. However, signatures consisting of combined miRNA pairs provide >90% overall accuracy in female heterozygous Mecp2$^{tm1.1Jae}$ and Mecp2$^{tm1.1Bird}$ mouse models.

The AUC for all four experiments are summarized in Table 5. Notably, certain miRNA pairs effectively distinguish between mutant and wild type mice consistently in all four animal models (Jae Null and Het and Bird Null and Het).

TABLE 5

Data summary for effective miRNA pairs. The table lists miRNA pairs identified in the four studies of Mecp2$^{tm1.1Bird}$, Null and Wt (male and female). Areas Under the ROC Curves (AUC) are presented.

| | Male (Number) | | Female (Number) | |
|---|---|---|---|---|
| Pairs | 1 (n = 19) | 2 (n = 18) | 3 (n = 13) | 4 (n = 20) |
| miR-107/miR-323-3p | 0.96 | 0.82 | 0.79 | 0.8 |
| miR-107/miR-335-5p | 0.96 | 0.99 | 0.93 | 0.8 |
| miR-107/miR-411 | 0.92 | | 0.75 | |
| miR-107/miR-132 | 0.86 | 0.98 | 0.71 | 0.82 |
| miR-107/miR-16 | 0.83 | | 0.71 | |
| miR-107/miR-491-5p | 0.73 | | 0.80 | |
| miR-491-5p/miR-323-3p | 0.97 | 0.81 | | 0.77 |
| miR-491-5p/miR-370 | 0.89 | | | |

TABLE 5-continued

Data summary for effective miRNA pairs. The table lists miRNA pairs identified in the four studies of Mecp2$^{tm1.1Bird}$, Null and Wt (male and female). Areas Under the ROC Curves (AUC) are presented.

|  | Male (Number) | | Female (Number) | |
| --- | --- | --- | --- | --- |
| Pairs | 1 (n = 19) | 2 (n = 18) | 3 (n = 13) | 4 (n = 20) |
| miR-491-5p/miR-335-5p | 0.96 | 0.98 | 0.79 | 0.78 |
| miR-491-5p/miR-411 | 0.87 | | 0.70 | |
| miR-491-5p/miR-132 | 0.87 | 0.99 | | 0.82 |
| miR-491-5p/miR-16 | 0.97 | 0.75 | | 0.71 |
| miR-16/miR-323-3p | 0.88 | 0.79 | 0.73 | 0.75 |
| miR-16/miR-335-5p | 0.91 | 0.98 | 0.95 | 0.75 |
| miR-16/miR-411 | 0.76 | | 0.79 | |
| miR-16/miR-132 | 0.70 | 1 | | |
| miR-132/miR-323-3p | 0.82 | | 0.81 | |
| miR-132/miR-335-5p | 0.84 | 0.89 | 0.96 | |
| miR-411/miR-323-3p | 0.77 | 0.84 | | |
| miR-411/miR-132 | | 0.93 | | |

Keeping in mind different gender and age of mouse in four experiments data are highly reproducible.

Example 6: Human Rett Syndrome Study

Introductory Comments

Rett diagnosis is currently based on clinical data and the analysis of the Mecp2 gene. There is a need for additional Rett diagnostic tests to meet the following needs:

1. Prediction of the disease outcome.
2. Prediction and diagnosis of pathology in different organs.
3. Enrollment of patients into clinical trials
4. Disease monitoring.
5. Drug development and treatment monitoring.

The search for Rett-related biomarkers was complicated by the fact that the disease develops in young age, when numerous parameters change even in controls due to organism growth, puberty and related processes.

Thus, all data were compared with respective age-matched controls (AMC).

Materials and Methods

Blood samples from RTT subjects and age matched girl controls (AMC) were collected at Montefiore Medical Center of Albert Einstein College of Medicine. Plasma was separated by centrifugation and frozen at −70° C. not later than two hours after blood collection. Concentrations of miRNAs in plasma were analyzed using RT-qPCR with primers and probes for each individual miRNA (TermoFisher). The amount of RNA equivalent to 25 µL of plasma were taken in each RT reaction, and the amount of miRNA (cDNA) equivalent to 2 µL plasma was taken into final PCR. The results obtained for each miRNA were converted into Relative Concentration (RC) of miRNA according to the ABI protocol ($2^{-\Delta C_t}$), normalized per potential normalizer miRNA (preselected using a computer program based on pre-selected AUC values), and this ratio was compared with respective control values.

Tables 6A-6C describe clinical data and demographics of the subjects who participated in the study. RTT phenotypes were presented as: 1. "Younger" (2-6 y.o., 10 girls); 2. "Classical Rett" (7-15 y.o., 10 girls); 3. "Adult" (18-33 y.o., 5 subjects); and 4. "High functioning" (10, 15, 15, 23, and 34 y.o., 5 subjects). Controls were presented as 3 groups: 1. "Younger" (3-5 y.o., 9 girls); 2. 6-17 y.o., 16 girls; and 3. Adult (18, 22, 24, 24, and 30 y.o., 5 subjects).

TABLE 6

Demographics of Rett syndrome subjects and clinical data (Bold indicates higher than normal levels of Cholesterol or ALT).

| # | Age at Blood Draw | Phenotype | Seizures | Ambulatory | Cholesterol (mg/dL) | ALT liver enyzmes (U/L) |
| --- | --- | --- | --- | --- | --- | --- |
| 1 | 3 | classical Rett | yes | yes | 190 (108-193) mg/dL | 13 (<=25) U/L |
| 2 | 15 | high functioning | no | yes | 144 (108-170) mg/dL | 12 (0-20) U/L |
| 3 | 13 | classical Rett | yes | walking w/ assistance | 171 (108-170) mg/dL | 15 (0-20) U/L |
| 4 | 32 | classical Rett | no | no | 166 (100-199) mg/dL | 38 (0-32) U/L |
| 5 | 7 | classical Rett | no | yes | 154 (106-193) mg/dL | 20 (10-35) U/L |
| 6 | 10 | classical Rett | yes | no | 143 (105-218) mg/dL | 26 (0-20) U/L |
| 7 | 9 | classical Rett | no | yes | 156 (105-218) mg/dL | 14 (<=25) U/L |
| 8 | 9 | classical Rett | no | yes | 116 (108-170) mg/dL | 20 (<=25) U/L |
| 9 | 14 | classical Rett | yes | yes | 133 (108-170) mg/dL | 29 (<=25) U/L |
| 10 | 21 | classical Rett | yes | yes | 147 (122-200) mg/dL | 10 (0-20) U/L |
| 11 | 18 | classical Rett | yes | yes | 125 (110-170) mg/dL | 18 (0-20) U/L |
| 12 | 5 | classical Rett | yes | yes | 203 (106-193) mg/dL | 13 (0-20) U/L |
| 13 | 15 | classical Rett | yes | yes | 146 (<170) mg/dL | 23 (0-31) U/L |
| 14 | 8 | classical Rett | no | yes | 141 (105-218) mg/dL | 17 (0-20) U/L |
| 15 | 13 | classical Rett | no | yes | 111 (105-218) mg/dL | 23 (0-20) U/L |

TABLE 6-continued

Demographics of Rett syndrome subjects and clinical data (Bold indicates higher than normal levels of Cholesterol or ALT).

| # | Age at Blood Draw | Phenotype | Seizures | Ambulatory | Cholesterol (mg/dL) | ALT liver enyzmes (U/L) |
|---|---|---|---|---|---|---|
| 16 | 6 | classical Rett | yes | yes | 98 (106-198) mg/dL | 14 (0-20) U/L |
| 17 | 8 | classical Rett | no | yes | 143 (105-218) mg/dL | 19 (0-20) U/L |
| 18 | 23 | high functioning | no | yes | 104 (<200) mg/dL | 29 (5-45) U/L |
| 19 | 15 | high functioning | no | yes | 175 (108-170) mg/dL | 8 (0-20) U/L |
| 20 | 3 | classical Rett | yes | no | 199 (108-193) mg/dL | 9 (0-20) U/L |
| 21 | 33 | classical Rett | yes | no | 217 (128-200) mg/dL | 9 0-20) U/L |
| 22 | 3 | classical Rett | no | standing wth support | 154 (76-216) mg/dL | 16 (0-20) U/L |
| 23 | 4 | classical Rett | no | yes | 118 (108-193) mg/dL | 14 (0-20) U/L |
| 24 | 2 | classical Rett | no | no | 144 (76-216) mg/dL | 15 (0-20) U/L |
| 25 | 5 | classical Rett | no | standing w/ support | 230 (106-193) mg/dL | 11 (0-20) U/L |
| 26 | 19 | classical Rett | yes | no | 127 (<200) mg/dL | 60 (9-32) U/L |
| 27 | 2 | classical Rett | no | standing w/ support | 182 (108-193) mg/dL | 30 (0-20) U/L |
| 28 | 5 | classical Rett | no | yes | 99 (106-193) mg/dL | 17 (0-20) U/L |
| 29 | 34 | high functioning | no | yes | 135 (125-200) mg/dL | 28 (6-29) U/L |
| 30 | 10 | high functioning | no | yes | 89 (105-218) mg/dL | 9 (0-20) U/L |

All subjects were divided into 3 age groups: 2-5 y.o., 6-15 y.o. and >15 y.o. To match ages in RTT and control groups, group boundaries were aligned (Table 7). "High functioning" overlaps those boundaries and was presented as a separate group.

TABLE 7

Age matched RTT and Control Groups

| Phenotype | Classical Rett | | | HF |
|---|---|---|---|---|
| Years range | 2-5 | 6-15 | >15 | >6 |
| RTT years | 3.6 ± 1.24 | 10.2 ± 3.06 | 24.6 ± 7.3 | 19.4 ± 9.3 |
| RTT cohort size | 9 | 11 | 5 | 5 |
| CNTR years | 3.6 ± 1.74 | 10.2 ± 3.0 | 20.8 ± 4.7 | |
| CNTR cohort size | 8 | 13 | 9 | |

Results and Data Analysis

All Rett Versus all Controls

Figure 10A:
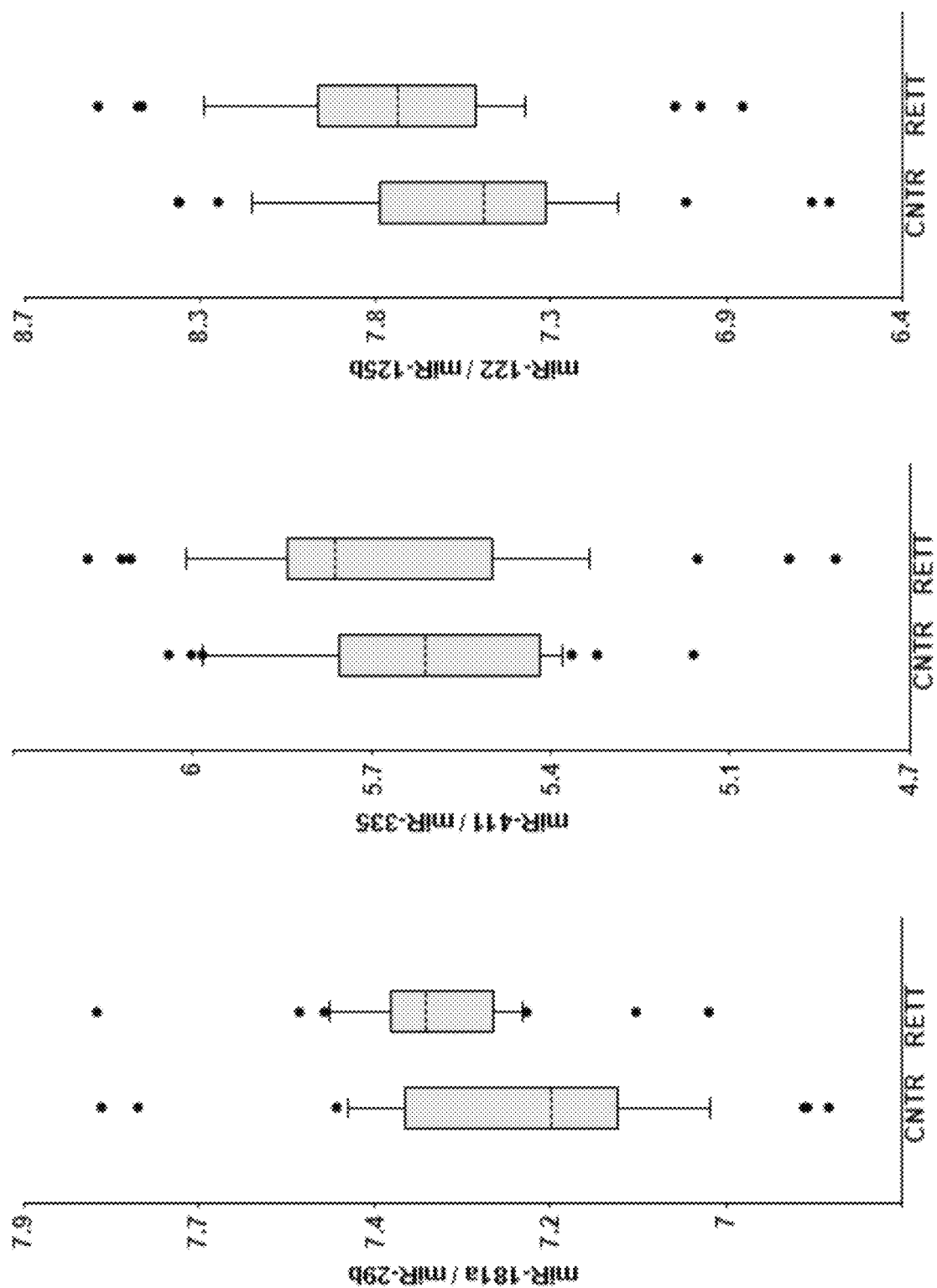
FIG. 10A is a plot showing biomarker miRNA pairs effectively distinguishing Rett subjects (RETT) and Control subjects (CNTR). miRNA ratios are presented as log 10 of $2^{\Delta Ct}$. Average for each pair is indicated.
Figure 10B:
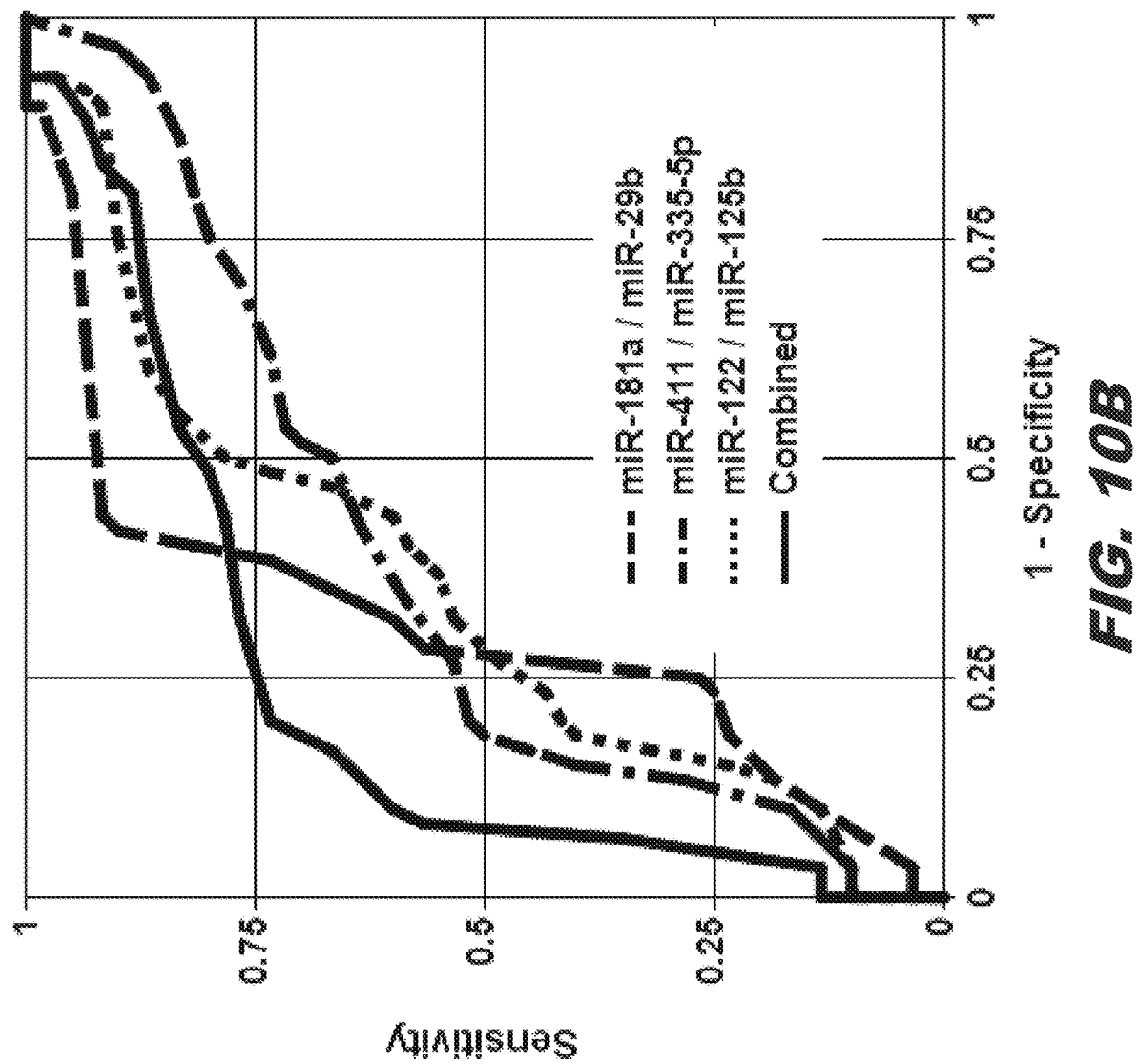
FIG. 10B is a graph presenting ROC curves for differentiation between Rett subjects (RETT) and Control subjects (CNTR) with individual miRNA pairs or their combination.

Initially a search for miRNA pairs and their combinations capable of differentiating all Rett subjects from all controls was performed. FIG. 10 and Table 8 demonstrate that the accuracy for individual pairs and their combinations is up to 66% and 75%, respectively depending on different stages of the disease development.

TABLE 8

Differentiation of all Rett subjects from all Controls by miRNA pairs and their combinations.

| | Pair | P_val | Sens | Spec | Acc | AUC |
|---|---|---|---|---|---|---|
| Rett_FULL(30)/ CNTR_FULL(30) | miR-411/miR-335p | 5.30E−02 | 0.65 | 0.55 | 0.6 | 0.66 |
| | miR-107/miR-335p | 4.20E−02 | 0.52 | 0.65 | 0.59 | 0.66 |
| | miR-122/miR-125b | 2.00E−02 | 0.56 | 0.62 | 0.59 | 0.68 |
| | miR-155/miR-125b | 2.70E−02 | 0.68 | 0.54 | 0.61 | 0.67 |
| | miR-433/miR-323-3p | 3.40E−02 | 0.6 | 0.54 | 0.57 | 0.67 |
| | miR-181a/miR-491-5p | 2.40E−02 | 0.63 | 0.6 | 0.62 | 0.68 |
| | miR-181a/miR-125b | 3.30E−03 | 0.69 | 0.63 | 0.66 | 0.73 |
| | miR-181a/miR-16 | 6.90E−03 | 0.64 | 0.68 | 0.66 | 0.71 |
| | miR-181a/let-7b | 3.20E−03 | 0.59 | 0.69 | 0.64 | 0.73 |
| | miR-181a/miR-132 | 3.30E−03 | 0.62 | 0.69 | 0.65 | 0.73 |
| | miR-181a/miR-155 | 1.20E−03 | 0.65 | 0.65 | 0.65 | 0.76 |

TABLE 8-continued

Differentiation of all Rett subjects from all Controls by miRNA pairs and their combinations.

| Pair | P_val | Sens | Spec | Acc | AUC |
|---|---|---|---|---|---|
| miR-181a/miR-29b | 4.20E−03 | 0.68 | 0.64 | 0.66 | 0.73 |
| miR-181a/miR-125b + miR-122/miR-125b + miR-181a/miR-491-5p | 9.50E−05 | 0.8 | 0.67 | 0.73 | 0.8 |
| miR-181a/miR-29b + miR-122/miR-125b + miR-411/miR-335 | 1.30E−04 | 0.77 | 0.73 | 0.75 | 0.81 |
| miR-433/miR-125b + miR-122/miR-125b + miR-181a/miR-335 | 1.30E−04 | 0.77 | 0.73 | 0.75 | 0.81 |
| miR-122/miR-125b + miR-181a/miR-491-5p + miR-155/miR-125b | 9.50E−05 | 0.8 | 0.7 | 0.75 | 0.81 |
| miR-122/miR-125b + miR-181a/miR-491-5p + miR-107/miR-335 | 8.40E−05 | 0.73 | 0.77 | 0.75 | 0.81 | miRNA Pairs and their Combinations Differentiating all Rett Subjects from all Controls (from Table 8):

miRNA Pairs:
miR-122/miR-125b, miR-155/miR125b, miR-433/mir-323-3p, miR-181a/miR-491-5p, miR-181a/miR-125b, miR-181a/miR-16, miR-181a/let-7b, miR-181a/miR-132, miR-181a/miR-155, miR-181a/miR-29b.

miRNA Pair Combinations:
miR-181a/miR-125b+miR-122/miR-125b+miR-181a/miR-491-5p;
miR-181a/miR-29b+miR-122/miR-125b+miR-411/miR-335-5p;
miR-433/miR-125b+miR-122/miR-125b+miR-181a/miR-335-5p;
miR-122/miR-125b+miR-181a/miR-491-5p+miR-155/miR-125b;
miR-122/miR-125b+miR-181a/miR-491-5p+miR-107/miR-335-5p.

Differentiation of Various Rett Age Cohorts from AMC (Age Matched Controls)

Figure 11A:
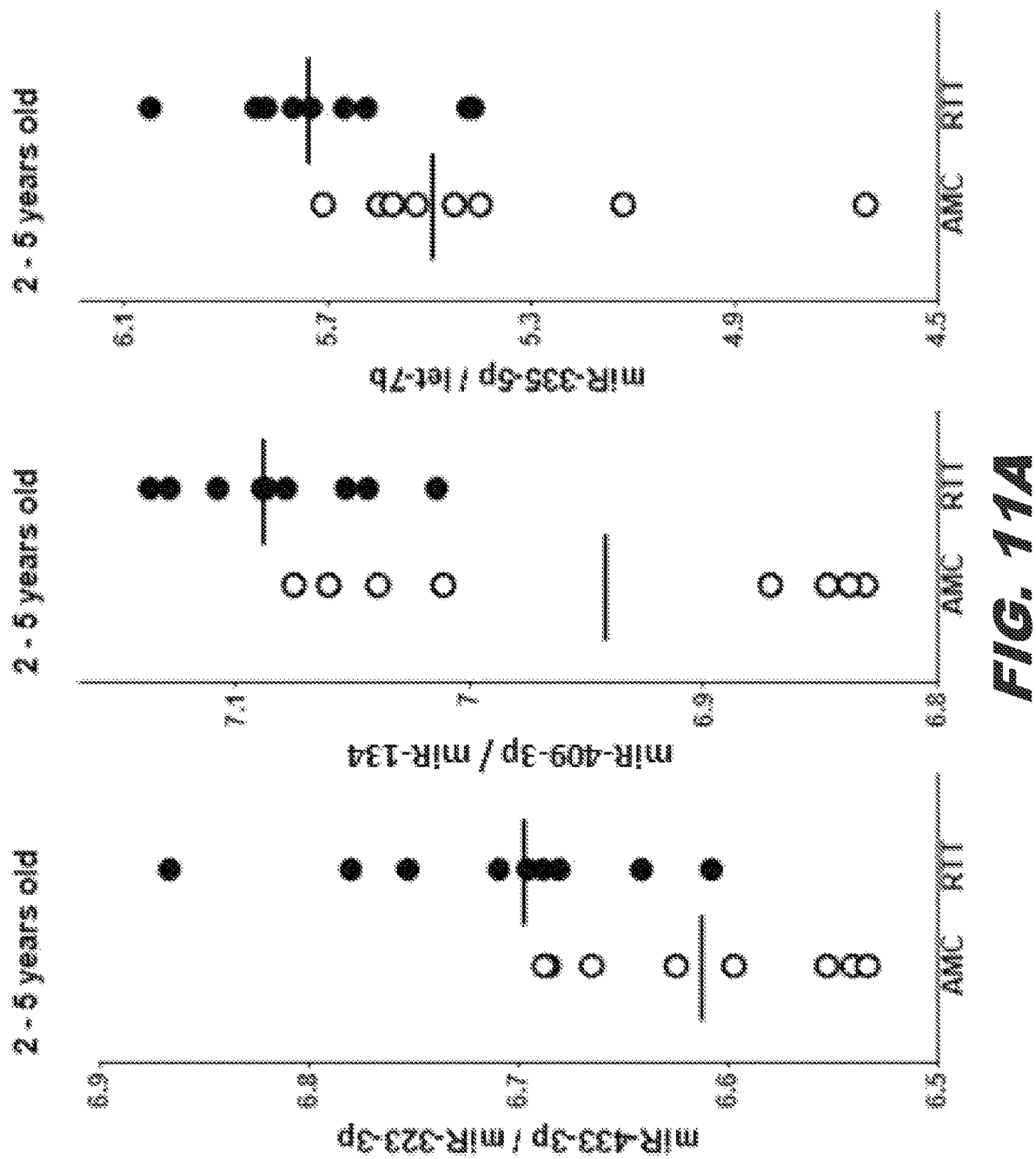
FIGS. 11A-C show plots differentiating between Rett groups and corresponding age-matched control (AMC) groups. A: differentiation between the control and Rett 2-5 y.o. groups. B: differentiation between the control and Rett 6-15 y.o. group. C: differentiation between the control and Rett >15 y.o. groups.
Figure 11B:
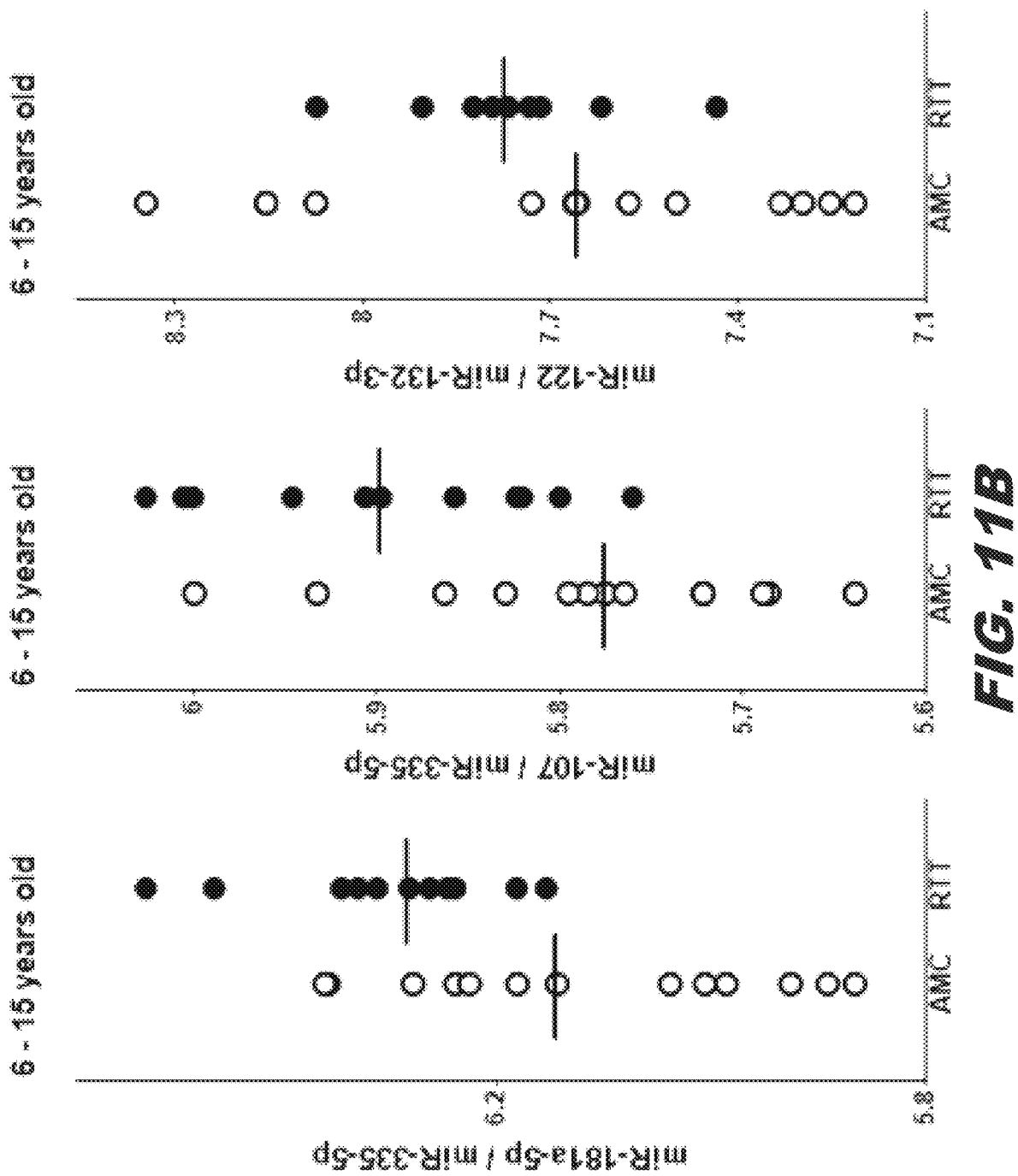
Figure 11C:
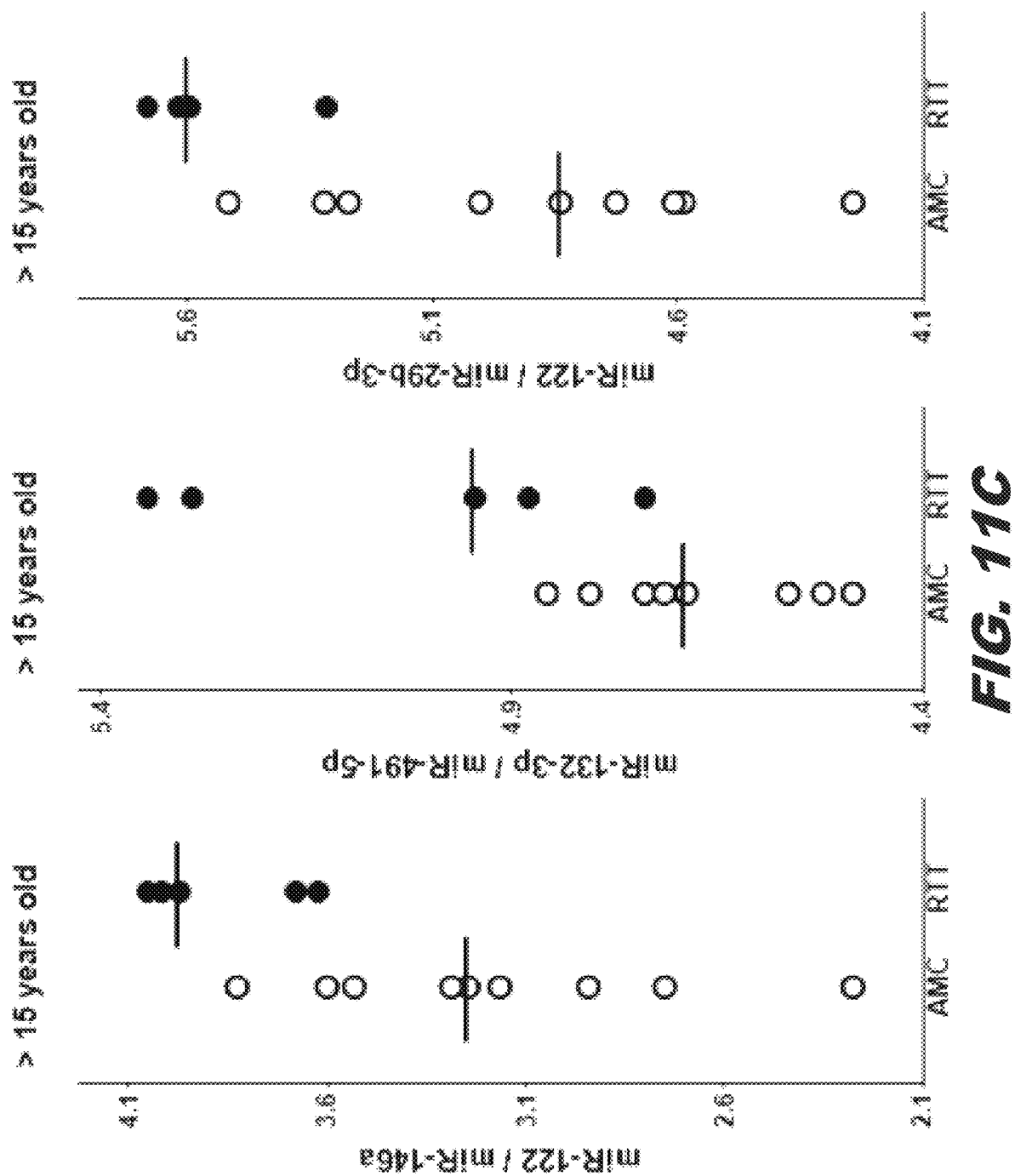
Figure 12A:
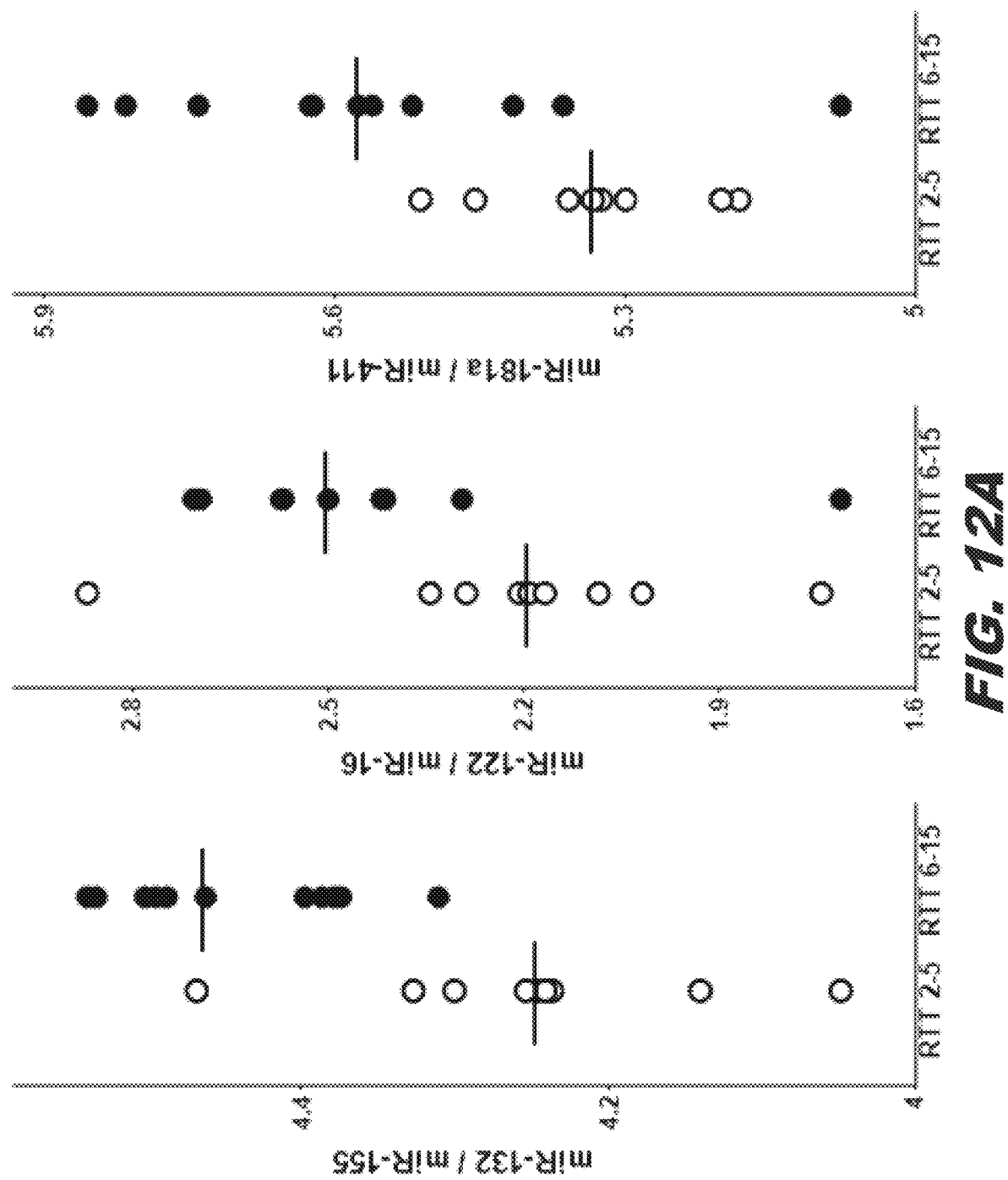
FIGS. 12A-C show plots differentiating between various Rett groups. A: differentiation between the Rett 6-15 and Rett 2-5 y.o. groups. B: differentiation between the Rett >15 y.o. and Rett 6-15 y.o. groups. C: differentiation between the Rett>15 y.o. and Rett 2-5 y.o. groups.
Figure 12B:
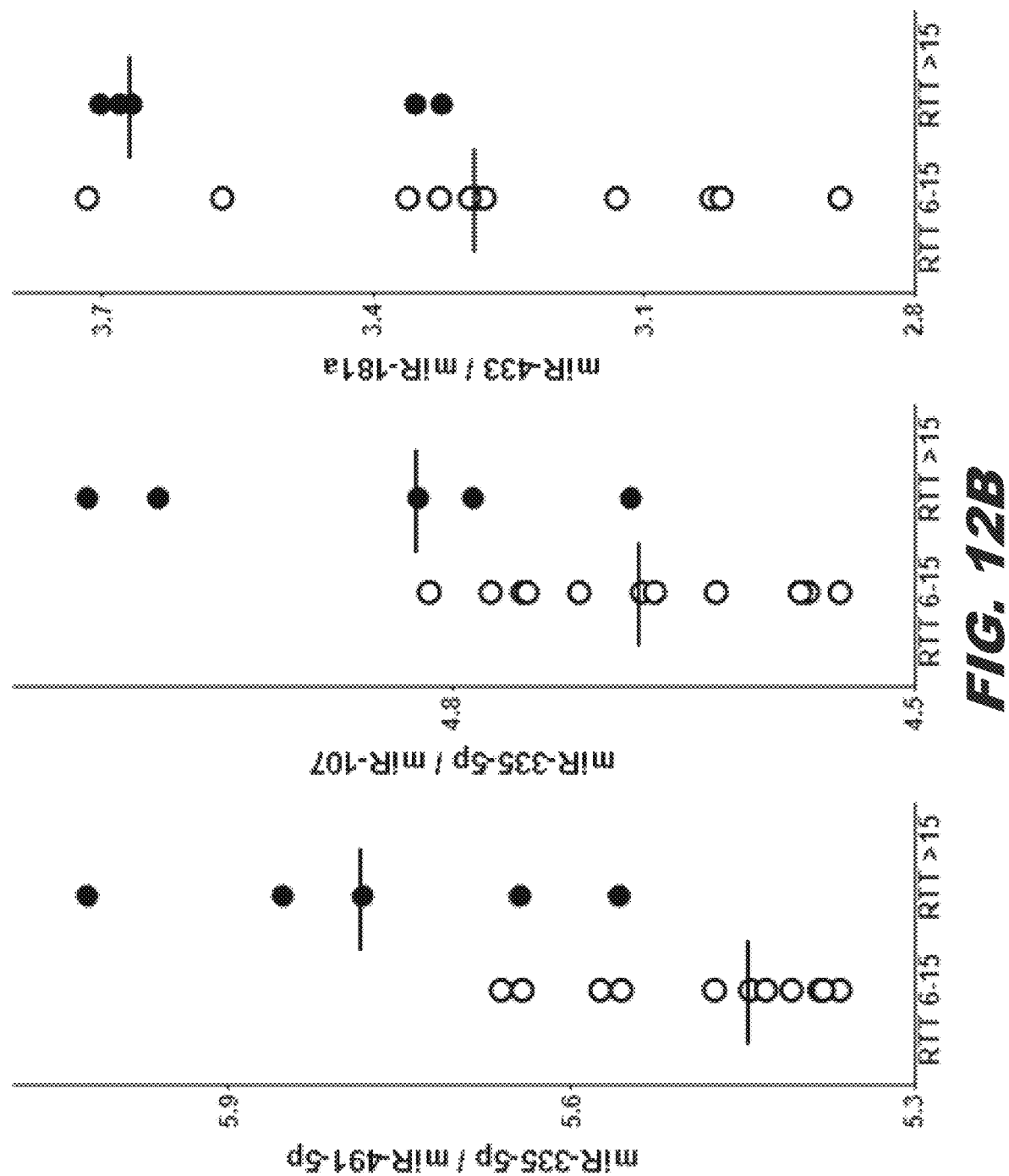
Figure 12C:
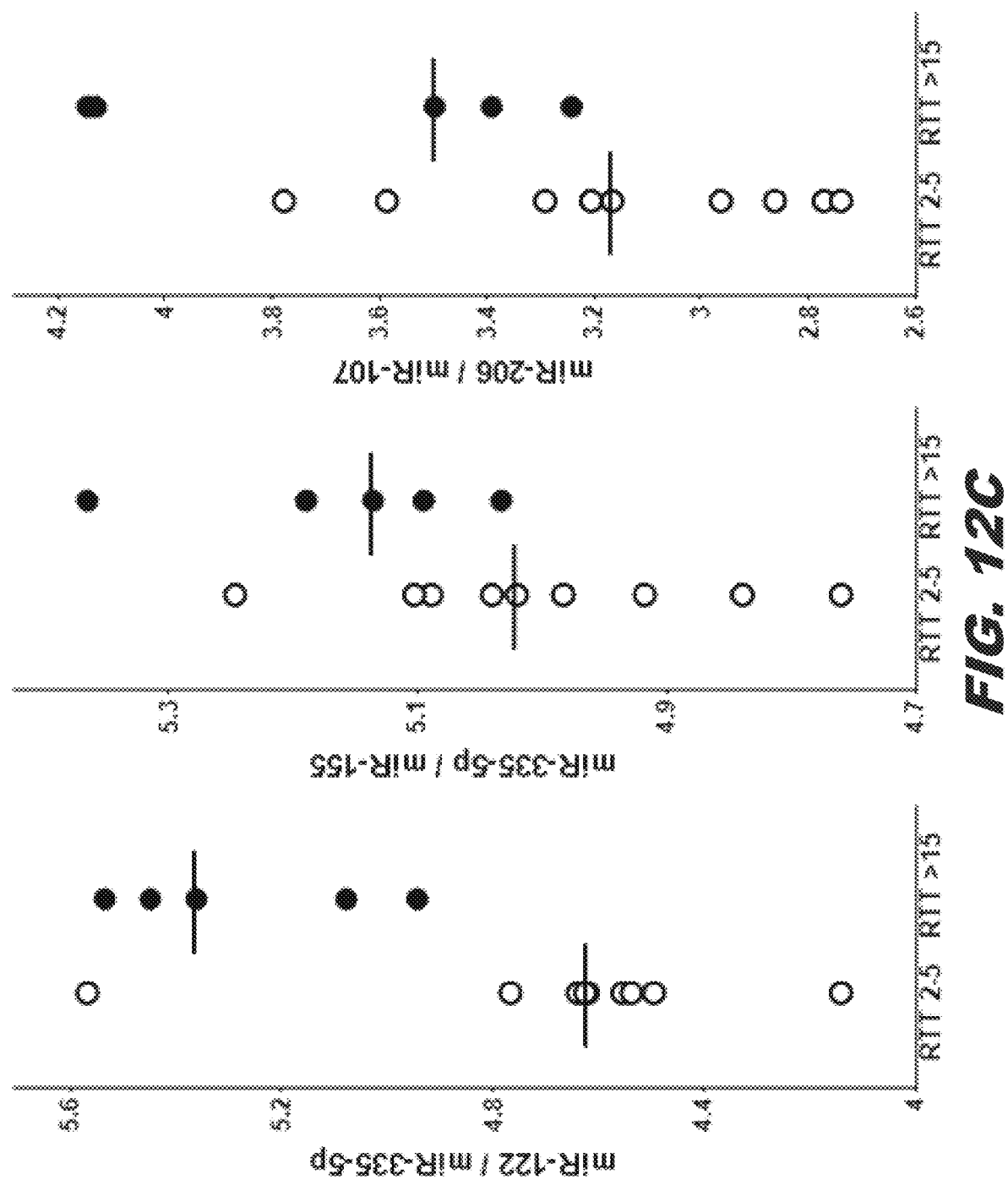
Figure 12D:
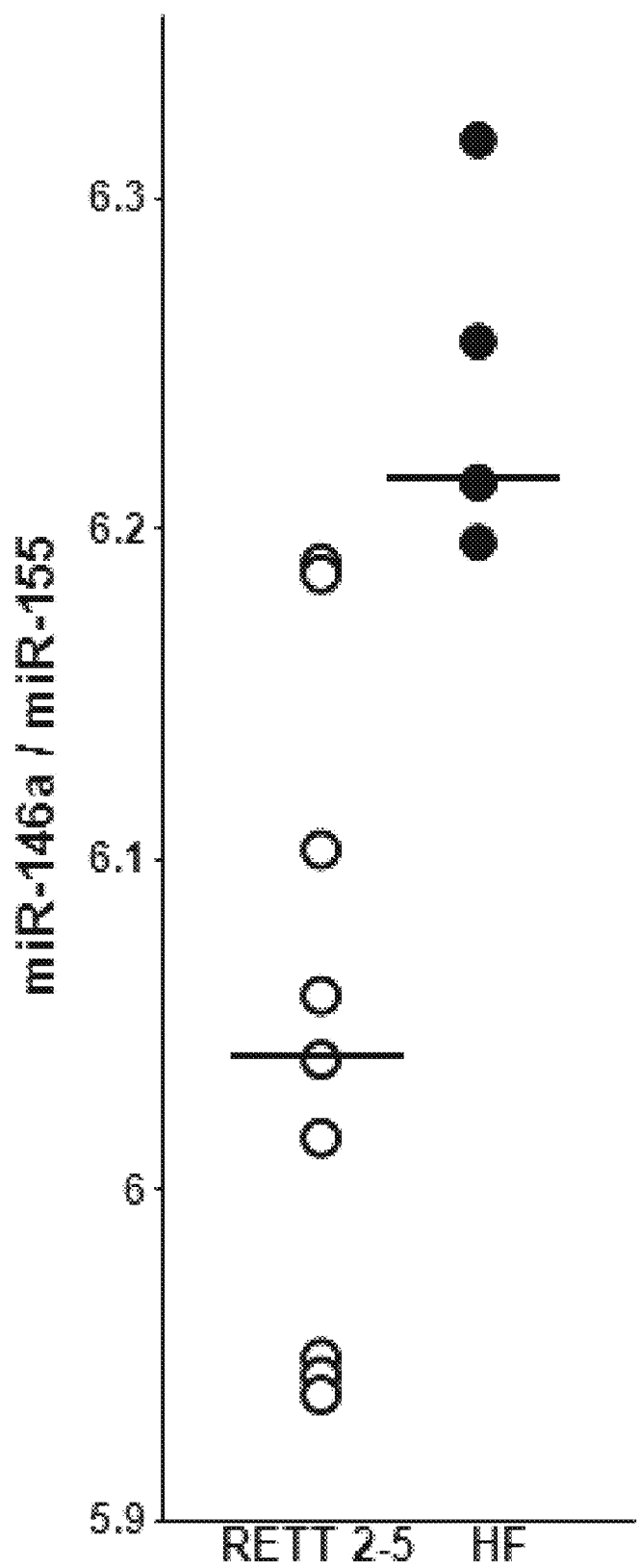
FIGS. 12D-F are plots showing the differentiation of "high functioning" Rett from the Rett 2-5 y.o., 6-15 y.o. and >15 y.o. groups, respectively.
Figure 12E:
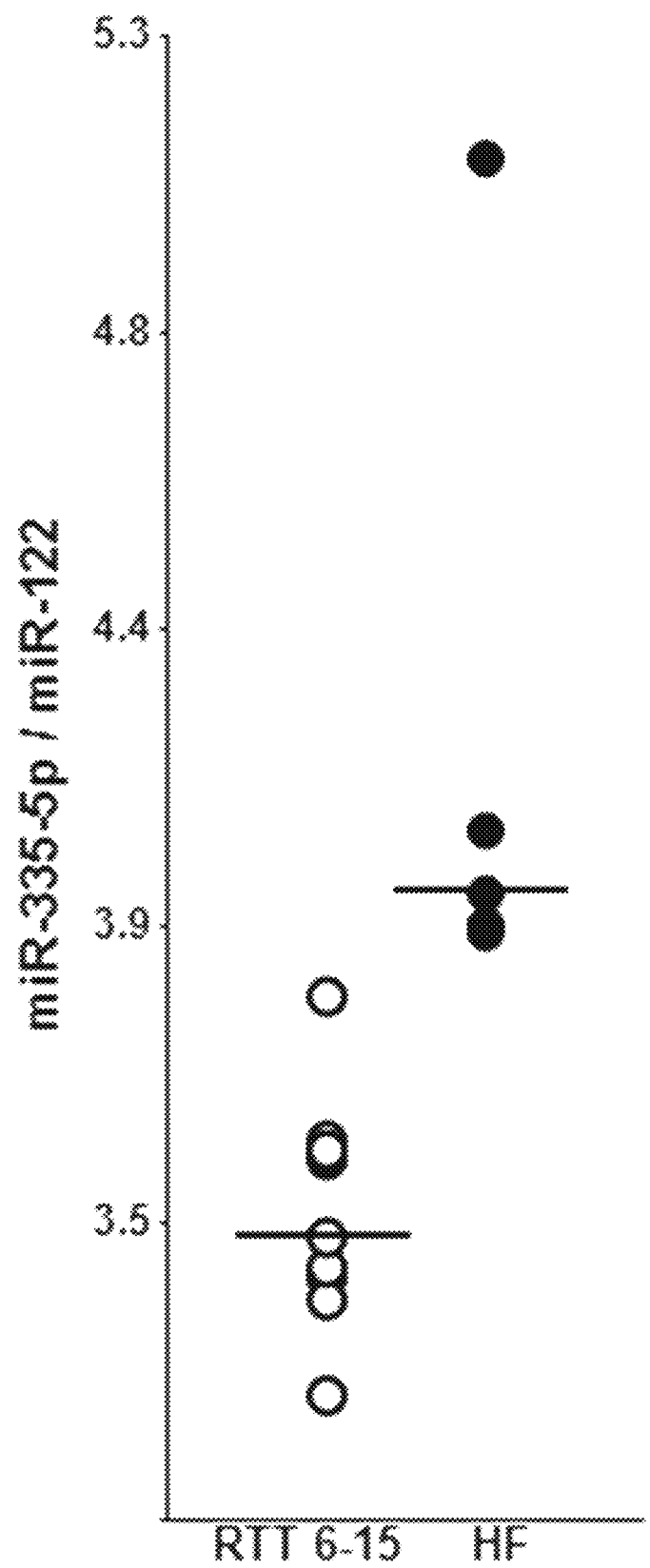
Figure 12F:
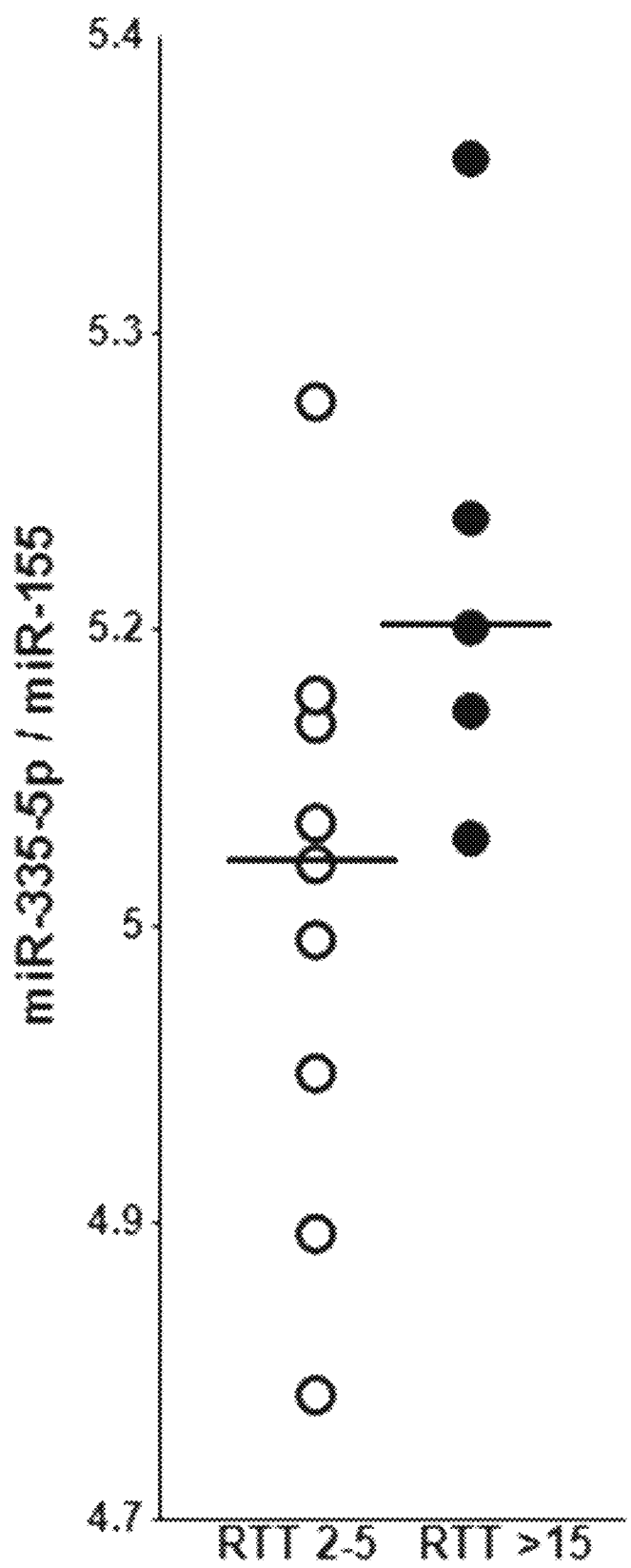

Further comparison of various Rett and AMC cohorts was performed (FIG. 11 A-C and Table 9A-C).

High functioning subjects were excluded for this part of the study since they belonged to various groups and significantly affected correlations.

TABLE 9

Differentiation of various age Rett cohorts from AMC. A - 2-5 y.o.; B - 6-15 y.o.; C - >15 y.o. groups

| | Pair | Sens | Spec | Acc | AUC | P_val |
|---|---|---|---|---|---|---|
| A | | | | | | |
| RTT 2-5 y.o.( | miR-155/miR-132 | 0.89 | 0.88 | 0.88 | 0.95 | 1.70E−03 |
| | miR-411/miR-134 | 1.00 | 0.63 | 0.82 | 0.94 | 4.10E−03 |
| | miR-409-3p/miR-134 | 0.72 | 0.81 | 0.76 | 0.94 | 2.30E−03 |
| | miR-432/miR-134 | 0.79 | 0.76 | 0.78 | 0.93 | 2.30E−03 |
| | miR-433/miR-323-3p | 0.75 | 0.72 | 0.74 | 0.90 | 4.10E−03 |
| | miR-335-5p/let-7b | 0.82 | 0.53 | 0.68 | 0.90 | 9.20E−03 |
| | miR-491-5p/miR-132 | 0.89 | 0.63 | 0.76 | 0.90 | 9.20E−03 |
| | miR-411/miR-323-3p | 0.82 | 0.53 | 0.68 | 0.88 | 1.90E−02 |
| | miR-491-5p/miR-16 | 0.78 | 0.75 | 0.76 | 0.87 | 1.50E−02 |
| | miR-409-3p/miR-134 + miR-433/miR-323-3p + miR-335-5p/let-7b | 1.00 | 1.00 | 1.00 | 1.00 | 2.20E−04 |
| | miR-29b/miR-125b + miR-409-3p/miR-134 + miR-433/miR-323-3p | 1.00 | 1.00 | 1.00 | 1.00 | 2.20E−04 |
| B | | | | | | |
| RTT 6-15 y.o. (11)/ CNTR_6-15 y.o. (13) | miR-181a/miR-155 | 0.82 | 0.69 | 0.75 | 0.88 | 4.50E−03 |
| | miR-181a/miR-335-5p | 0.85 | 0.64 | 0.74 | 0.85 | 5.30E−03 |
| | miR-181a/miR-29b | 0.82 | 0.77 | 0.79 | 0.85 | 4.50E−03 |
| | miR-107/miR-335-5p | 0.62 | 0.75 | 0.69 | 0.84 | 5.30E−03 |
| | miR-122/miR-132 | 0.62 | 0.74 | 0.69 | 0.81 | 3.60E−02 |

TABLE 9-continued

Differentiation of various age Rett cohorts from AMC. A - 2-5 y.o.; B - 6-15 y.o.; C - >15 y.o. groups

| | Pair | Sens | Spec | Acc | AUC | P_val |
|---|---|---|---|---|---|---|
| | miR-491-5p/miR-335-5p | 0.64 | 0.62 | 0.62 | 0.81 | 1.80E-02 |
| | miR-411/miR-323-3p | 0.64 | 0.62 | 0.62 | 0.71 | 1.00E-01 |
| | miR-181a/miR-335-5p + miR-107/miR-335-5p + miR-122/miR-132 | 0.91 | 0.69 | 0.79 | 0.97 | 1.00E-04 |
| | miR-181a/miR-155 + miR-181a/miR-335-5p + miR-107/miR-335-5p | 0.91 | 0.85 | 0.88 | 0.94 | 3.10E-04 |
| C | | | | | | |
| RTT >15 y.o. (5)/ CNTR >15 y.o. (9) | miR-122/miR-491-5p | 1.00 | 0.89 | 0.93 | 0.99 | 1.60E-03 |
| | miR-122/miR-107 | 0.83 | 0.93 | 0.89 | 0.98 | 2.50E-03 |
| | miR-122/miR-146a | 1.00 | 0.78 | 0.86 | 0.98 | 2.50E-03 |
| | miR-122/miR-335-5p | 0.83 | 0.81 | 0.82 | 0.94 | 5.60E-03 |
| | miR-122/miR-29b | 0.83 | 0.93 | 0.89 | 0.98 | 2.50E-03 |
| | miR-122/miR-155 | 0.85 | 0.83 | 0.84 | 0.97 | 3.80E-03 |
| | miR-122/miR-181a | 0.85 | 0.83 | 0.84 | 0.96 | 3.80E-03 |
| | miR-122/miR-411 | 0.80 | 0.78 | 0.79 | 0.92 | 8.10E-03 |
| | miR-122/miR-409-3p | 0.64 | 0.82 | 0.76 | 0.92 | 8.10E-03 |
| | miR-122/miR-432 | 0.64 | 0.82 | 0.76 | 0.92 | 8.10E-03 |
| | miR-122/miR-134 | 0.80 | 0.78 | 0.79 | 0.96 | 5.60E-03 |
| | miR-16/miR-491-5p | 0.83 | 0.81 | 0.82 | 0.94 | 8.10E-03 |
| | miR-433/miR-491-5p | 0.64 | 0.82 | 0.76 | 0.92 | 8.10E-03 |
| | miR-132/miR-491-5p | 0.85 | 0.83 | 0.84 | 0.97 | 3.80E-03 |
| | miR-122/miR-146a + miR-132/miR-491-5p | 1.00 | 1.00 | 1.00 | 1.00 | 1.10E-03 |
| | miR-122/miR-491-5p + miR-122/miR-29b + miR-132/miR-491-5p | 1.00 | 1.00 | 1.00 | 1.00 | 1.10E-03 | miRNA pairs distinguishing different age Rett subjects from AMC reflect disease dynamics: in the youngest 2-5 y.o. groups brain-enriched miRNAs dominate, reflecting brain pathology, then liver-enriched miR-122 appears, which became the best numerator in >15 y.o. group. It is important to mention that many pairs of miRNAs tested in animal and human Rett subjects are overlapping (Table 10), which indicates the similarity of brain pathology in both systems and possibility to use the same miRNAs for pre-clinical and clinical studies and drug development.

TABLE 10

Areas Under the ROC Curves (AUC) in animal and human studies.

| | Animals, 4 genotypes | | | | Humans, 3 age ranges | | |
|---|---|---|---|---|---|---|---|
| | Male (Number) | | Female (Number) | | 2-5 | 6-15 | >15 |
| Pairs | 1 (n = 19) | 2 (n = 18) | 3 (n = 13) | 4 (n = 20) | years n = 17 | years n = 24 | years n = 14 |
| miR-107/miR-323-3p | 0.96 | 0.82 | 0.79 | 0.8 | 0.76 | | |
| miR-107/miR-335-5p | 0.96 | 0.99 | 0.93 | 0.8 | 0.72 | 0.84 | |
| miR-107/miR-411 | 0.92 | | 0.75 | | | | |
| miR-107/miR-132 | 0.86 | 0.98 | 0.71 | 0.82 | 0.85 | 0.65 | |
| miR-107/miR-16 | 0.83 | | 0.71 | | 0.88 | | |
| miR-107/miR-491-5p | 0.73 | | 0.8 | | 0.70 | 0.67 | 0.91 |
| miR-491-5p/miR-323-3p | 0.97 | 0.81 | | 0.77 | 0.65 | | |
| miR-491-5p/miR-335-5p | 0.96 | 0.98 | 0.79 | 0.78 | | 0.81 | |
| miR-491-5p/miR-370 | 0.89 | | | | | | |
| miR-491-5p/miR-411 | 0.87 | | 0.7 | | | | |
| miR-491-5p/miR-132 | 0.87 | 0.99 | | 0.82 | 0.90 | 0.67 | |
| miR-491-5p/miR-16 | 0.97 | 0.75 | | 0.71 | 0.87 | | |
| miR-16/miR-323-3p | 0.88 | 0.79 | 0.73 | 0.75 | | | 0.72 |
| miR-16/miR-335-5p | 0.91 | 0.98 | 0.95 | 0.75 | | | 0.80 |
| miR-16/miR-411 | 0.76 | | 0.79 | | | | 0.77 |
| miR-16/miR-132 | 0.7 | 1 | | | | | 0.70 |
| miR-132/miR-323-3p | 0.82 | | 0.81 | | | | |

TABLE 10-continued

Areas Under the ROC Curves (AUC) in animal and human studies.

| | Animals, 4 genotypes | | | | Humans, 3 age ranges | | |
|---|---|---|---|---|---|---|---|
| | Male | | Female | | 2-5 | 6-15 | >15 |
| | (Number) | | (Number) | | years | years | years |
| Pairs | 1 (n = 19) | 2 (n = 18) | 3 (n = 13) | 4 (n = 20) | n = 17 | n = 24 | n = 14 |
| miR-132/miR-335-5p | 0.84 | 0.89 | 0.96 | | | | 0.91 |
| miR-411/miR-323-3p | 0.77 | 0.84 | | | 0.88 | 0.71 | |
| miR-411/miR-132 | | 0.93 | | | 0.81 | 0.65 | | miRNA Pairs Differentiating Various Rett Subjects from AMCs (from Table 9):

2-5 y. o. Rett Subjects:

miR-411/miR-125b, miR-432/miR-125b, miR-181a/miR-125b, miR-107/miR-125b, miR-433/miR-125b, miR-491-5p/miR-125b.

6-15 y. o. Rett Subjects:

miR-181a/miR-132, miR-181a/let-7b, miR-181a/miR-155, miR-411/miR-323-3p, miR-491-5p/miR-335-5p, miR-107/miR-335-5p.

>15 y.o. Rett Subjects:
miR-433/miR-491-5p, miR-122/miR-107, miR-132/miR-491-5p, miR-132/miR-335-5p, miR-125b/miR-335-5p, miR-122/miR-181a.

Differentiation of Various Rett Groups from Each Other

Then the ability of miRNA pairs and their combinations to differentiate consecutive age Rett cohorts from each other was tested. FIG. 12 and Table 11 demonstrates that they are effectively distinguished by many miRNA pairs with up to 80%-90% accuracy. It is important that the same miRNA pairs practically do not differentiate the same age control groups from each other (Table 11), which means that the positive results with Rett subjects reflects disease progression, not the age-dependent changes.

TABLE 11

Differentiation of various Rett consecutive age cohorts and inability of the same miRNA pairs to distinguish the same age Controls from each other.

| | | RTT | | | | |
|---|---|---|---|---|---|---|
| | Pair | Sens | Spec | Acc | AUC | P-val |
| RTT 6-15 y.o. (11)/2-5 y.o. pairs (9) | miR-122/miR-155 | 0.91 | 0.89 | 0.90 | 0.95 | 9.10E−04 |
| | miR-122/miR-335-5p | 0.91 | 0.89 | 0.90 | 0.94 | 1.50E−03 |
| | miR-132-3p/miR-155 | 0.91 | 0.89 | 0.90 | 0.96 | 5.40E−04 |
| | miR-122/miR-146a | 0.82 | 0.89 | 0.85 | 0.92 | 3.10E−03 |
| | miR-122/miR-491-5p | 0.82 | 0.89 | 0.85 | 0.92 | 3.10E−03 |
| | miR-122/miR-16 | 0.84 | 0.80 | 0.83 | 0.89 | 9.20E−03 |
| | miR-122/miR-29b-5p | 0.73 | 0.89 | 0.80 | 0.93 | 2.50E−03 |
| | miR-122/miR-107 | 0.73 | 0.89 | 0.80 | 0.92 | 3.90E−03 |
| | miR-132-3p/miR-323-3p | 0.82 | 0.78 | 0.80 | 0.89 | 7.50E−03 |
| | miR-122/miR-432-5p | 0.76 | 0.82 | 0.79 | 0.92 | 1.90E−03 |
| | miR-122/miR-411-5p | 0.76 | 0.82 | 0.79 | 0.92 | 2.50E−03 |
| | miR-132-3p/miR-432-5p | 0.85 | 0.69 | 0.78 | 0.89 | 7.50E−03 |
| RTT 6-15 y.o. (11)/2-5 y.o. pairs (9) | miR-122/miR-409-3p | 0.73 | 0.78 | 0.75 | 0.88 | 6.10E−03 |
| | miR-181a-5p/miR-411-5p | 0.73 | 0.78 | 0.75 | 0.86 | 2.00E−02 |
| | let-7b/miR-155 | 0.79 | 0.64 | 0.73 | 0.86 | 7.50E−03 |
| | miR-132-3p/miR-411-5p | 0.67 | 0.81 | 0.73 | 0.86 | 1.10E−02 |
| | miR-323-3p/miR-432-5p | 0.70 | 0.75 | 0.72 | 0.86 | 7.50E−03 |
| | let-7b/miR-432-5p | 0.73 | 0.67 | 0.70 | 0.86 | 1.10E−02 |
| | miR-122/miR-323-3p | 0.58 | 0.83 | 0.69 | 0.90 | 3.90E−03 |
| | miR-122/miR-433-3p | 0.57 | 0.81 | 0.68 | 0.89 | 3.90E−03 |
| | miR-409-3p/miR-432-5p | 0.52 | 0.85 | 0.67 | 0.85 | 1.10E−02 |
| | miR-181a-5p/miR-155 | 0.59 | 0.72 | 0.65 | 0.85 | 2.00E−02 |
| | miR-122/miR-181a-5p | 0.49 | 0.80 | 0.63 | 0.86 | 1.40E−02 |

TABLE 11-continued

Differentiation of various Rett consecutive age cohorts and inability of the same miRNA pairs to distinguish the same age Controls from each other.

| | | CNTR | | | | |
|---|---|---|---|---|---|---|
| | Pair | Sens | Spec | Acc | AUC | P-val |
| RTT 6-15 y.o. (11)/2-5 y.o. pairs (9) | miR-122/miR-155 | 0.38 | 0.61 | 0.46 | 0.55 | 4.30E−01 |
| | miR-122/miR-335-5p | 0.36 | 0.46 | 0.40 | 0.45 | 1.60E−01 |
| | miR-132-3p/miR-155 | 0.43 | 0.59 | 0.49 | 0.55 | 3.70E−01 |
| | miR-122/miR-146a | 0.36 | 0.58 | 0.44 | 0.50 | 2.50E−01 |
| | miR-122/miR-491-5p | 0.32 | 0.64 | 0.44 | 0.51 | 2.90E−01 |
| | miR-122/miR-16 | 0.46 | 0.38 | 0.43 | 0.55 | 3.70E−01 |
| | miR-122/miR-29b-5p | 0.31 | 0.63 | 0.43 | 0.49 | 2.20E−01 |
| | miR-122/miR-107 | 0.31 | 0.63 | 0.43 | 0.49 | 2.50E−01 |
| | miR-132-3p/miR-323-3p | 0.54 | 0.38 | 0.48 | 0.63 | 4.30E−01 |
| | miR-122/miR-432-5p | 0.44 | 0.48 | 0.45 | 0.54 | 4.30E−01 |
| | miR-122/miR-411-5p | 0.42 | 0.54 | 0.47 | 0.56 | 4.60E−01 |
| | miR-132-3p/miR-432-5p | 0.44 | 0.48 | 0.45 | 0.56 | 4.00E−01 |
| | miR-122/miR-409-3p | 0.49 | 0.66 | 0.56 | 0.68 | 2.70E−01 |
| | miR-181a-5p/miR-411-5p | 0.46 | 0.50 | 0.48 | 0.60 | 4.30E−01 |
| | let-7b/miR-155 | 0.56 | 0.52 | 0.55 | 0.69 | 2.00E−01 |
| | miR-132-3p/miR-411-5p | 0.43 | 0.46 | 0.44 | 0.54 | 4.30E−01 |
| | miR-323-3p/miR-432-5p | 0.33 | 0.54 | 0.41 | 0.48 | 2.50E−01 |
| | let-7b/miR-432-5p | 0.57 | 0.46 | 0.53 | 0.60 | 4.30E−01 |
| | miR-122/miR-323-3p | 0.45 | 0.48 | 0.46 | 0.60 | 4.30E−01 |
| | miR-122/miR-433-3p | 0.43 | 0.46 | 0.44 | 0.56 | 4.60E−01 |
| | miR-409-3p/miR-432-5p | 0.23 | 0.63 | 0.38 | 0.41 | 1.00E−01 |
| | miR-181a-5p/miR-155 | 0.62 | 0.63 | 0.62 | 0.66 | 2.70E−01 |
| | miR-122/miR-181a-5p | 0.38 | 0.50 | 0.43 | 0.52 | 2.50E−01 |

| | | RTT | | | | |
|---|---|---|---|---|---|---|
| | Pair | Sens | Spec | Acc | AUC | P-val |
| RTT >15 y.o. (5)/6-15 y.o. pairs (11) | miR-122/miR-491-5p | 0.80 | 0.91 | 0.87 | 0.94 | 6.10E−03 |
| | miR-122/miR-181a-5p | 0.80 | 0.91 | 0.87 | 0.93 | 8.40E−03 |
| | miR-122/miR-29b-5p | 0.83 | 0.85 | 0.84 | 0.93 | 8.40E−03 |
| | miR-335-5p/miR-491-5p | 0.83 | 0.85 | 0.84 | 0.95 | 3.10E−03 |
| | miR-122/miR-155 | 0.82 | 0.84 | 0.83 | 0.91 | 1.50E−02 |
| | miR-335-5p/miR-181a-5p | 0.81 | 0.83 | 0.82 | 0.89 | 2.60E−02 |
| | miR-411-5p/miR-491-5p | 0.80 | 0.82 | 0.81 | 0.88 | 2.60E−02 |
| | miR-122/miR-107 | 0.85 | 0.77 | 0.80 | 0.92 | 1.10E−02 |
| | miR-433-3p/miR-491-5p | 0.85 | 0.77 | 0.80 | 0.94 | 4.40E−03 |
| | miR-122/miR-146a | 0.63 | 0.85 | 0.78 | 0.89 | 1.50E−02 |
| | miR-155/miR-491-5p | 0.82 | 0.75 | 0.77 | 0.88 | 2.00E−02 |
| | miR-433-3p/miR-181a-5p | 0.80 | 0.73 | 0.75 | 0.87 | 2.00E−02 |
| | miR-432-5p/miR-491-5p | 0.80 | 0.73 | 0.75 | 0.87 | 2.60E−02 |
| | miR-335-5p/miR-146a | 0.80 | 0.73 | 0.75 | 0.88 | 2.00E−02 |
| | let-7b/miR-491-5p | 0.60 | 0.82 | 0.75 | 0.86 | 2.60E−02 |
| | miR-335-5p/miR-107 | 0.86 | 0.69 | 0.74 | 0.94 | 6.10E−03 |
| | miR-122/miR-132-3p | 0.42 | 0.86 | 0.72 | 0.88 | 1.50E−02 |
| | miR-146a/miR-491-5p | 0.58 | 0.78 | 0.72 | 0.87 | 1.50E−02 |
| | miR-16/miR-491-5p | 0.85 | 0.58 | 0.67 | 0.85 | 3.40E−02 |
| | miR-433-3p/miR-107 | 0.67 | 0.61 | 0.63 | 0.86 | 4.40E−02 |

| | | CNTR | | | | |
|---|---|---|---|---|---|---|
| | Pair | Sens | Spec | Acc | AUC | P-val |
| RTT >15 y.o. (5)/6-15 y.o. pairs (11) | miR-122/miR-491-5p | 0.48 | 0.41 | 0.44 | 0.41 | 1.10E−01 |
| | miR-122/miR-181a-5p | 0.46 | 0.40 | 0.43 | 0.50 | 1.90E−01 |
| | miR-122/miR-29b-5p | 0.32 | 0.58 | 0.47 | 0.43 | 1.40E−01 |
| | miR-335-5p/miR-491-5p | 0.44 | 0.46 | 0.45 | 0.56 | 4.20E−01 |
| | miR-122/miR-155 | 0.34 | 0.55 | 0.46 | 0.48 | 2.50E−01 |
| | miR-335-5p/miR-181a-5p | 0.53 | 0.52 | 0.52 | 0.63 | 2.70E−01 |

TABLE 11-continued

Differentiation of various Rett consecutive age cohorts and inability of the same miRNA pairs to distinguish the same age Controls from each other.

| | | | | | |
|---|---|---|---|---|---|
| miR-411-5p/miR-491-5p | 0.74 | 0.44 | 0.56 | 0.73 | 1.30E−01 |
| miR-122/miR-107 | 0.33 | 0.46 | 0.41 | 0.41 | 1.00E−01 |
| miR-433-3p/miR-491-5p | 0.51 | 0.42 | 0.45 | 0.53 | 3.70E−01 |
| miR-122/miR-146a | 0.32 | 0.52 | 0.44 | 0.45 | 1.40E−01 |
| miR-155/miR-491-5p | 0.29 | 0.40 | 0.35 | 0.45 | 4.70E−02 |
| miR-433-3p/miR-181a-5p | 0.73 | 0.58 | 0.64 | 0.74 | 1.30E−01 |
| miR-432-5p/miR-491-5p | 0.70 | 0.42 | 0.53 | 0.65 | 2.70E−01 |
| miR-335-5p/miR-146a | 0.56 | 0.62 | 0.59 | 0.75 | 1.40E−01 |
| let-7b/miR-491-5p | 0.33 | 0.38 | 0.36 | 0.39 | 5.40E−02 |
| miR-335-5p/miR-107 | 0.49 | 0.34 | 0.40 | 0.50 | 2.50E−01 |
| miR-122/miR-132-3p | 0.46 | 0.47 | 0.47 | 0.54 | 3.40E−01 |
| miR-146a/miR-491-5p | 0.36 | 0.50 | 0.44 | 0.51 | 3.40E−01 |
| miR-16/miR-491-5p | 0.33 | 0.38 | 0.36 | 0.37 | 4.10E−02 |
| miR-433-3p/miR-107 | 0.55 | 0.45 | 0.49 | 0.57 | 4.70E−01 |

Differentiation of Various Clinical Subgroups from Other Rett Subjects

Finally, the existence of biomarker miRNA pairs to differentiate Rett subjects with specific clinical symptoms from other Rett patients was analyzed. Tables 12A-C demonstrate that: (i) subjects with walking problems (muscle-related pathology) are most effectively differentiated from walking (ambulatory) Rett patients by miRNA pairs with muscle-enriched miR-206 as a numerator; (ii) Subjects with abnormally high level of ALT indicating liver pathology are effectively distinguished from other Rett patients with miRNA pairs having as numerators liver-enriched miR-122. Other miRNA pairs include as numerators miR-206 reflecting coexistence of liver and muscle pathologies and pro-apoptotic miR-16, which most likely is involved in excessive cell death in different organs and tissues; (iii) subjects with the higher than normal level of cholesterol are effectively differentiated from the rest of Rett patients and again numerators of the most effective pairs are miRNAs involved in regulation of cholesterol metabolism, such as inflammatory miR-146a (Simionescu et al. Mol. Biol. Rep. 2014, 41, 5765-5773; Cheng et al. Circ. Res. 2017, 121, 354-367), miR-206 (Vnod et al., Biochim. Biophys. Acta 2014, 1841, 827-835; Zheng et al. Mol. Med. Rep. 2018, 17, 5635-5641) as well as brain-enriched miRNAs.

Thus, miRNA pairs can be effective biomarkers for prognosis, detection and monitoring of various organ pathology and metabolic changes in Rett subjects.

TABLE 12

Differentiation of various RTT clinical subgroups from other RTT subjects. A-subjects with walking/muscle problems; B-subjects with the positive liver enzyme ALT probes; C-subjects with higher than normal cholesterol level.

| Pairs | Accuracy | AUC | P-value |
|---|---|---|---|
| A | | | |
| Walking problems: Yes(10)/No(20) | | | |
| miR-206/miR-125b | 0.79 | 0.95 | 1.70E−04 |
| miR-206/miR-491-5p | 0.69 | 0.82 | 7.30E−03 |
| miR-206/miR-29b | 0.69 | 0.82 | 6.40E−03 |
| miR-206/miR-107 | 0.68 | 0.81 | 7.30E−03 |
| miR-206/miR-132 | 0.78 | 0.88 | 1.10E−03 |
| miR-206/miR-335-5p | 0.68 | 0.81 | 7.30E−03 |
| miR-206/miR-155 | 0.70 | 0.84 | 5.00E−03 |
| miR-206/let-7b | 0.73 | 0.83 | 6.40E−03 |
| miR-206/miR-146a | 0.67 | 0.79 | 1.80E−02 |
| miR-206/miR-134 | 0.63 | 0.82 | 1.80E−02 |
| miR-206/miR-181a | 0.69 | 0.81 | 1.60E−02 |
| miR-206/miR-409-3p | 0.65 | 0.80 | 1.50E−02 |
| miR-206/miR-16 | 0.74 | 0.83 | 5.70E−03 |
| miR-206/miR-323-3p | 0.68 | 0.80 | 1.50E−02 |
| miR-206/miR-411 | 0.65 | 0.78 | 2.80E−02 |
| miR-433/miR-125b | 0.65 | 0.78 | 3.40E−02 |
| miR-432/miR-411 | 0.65 | 0.75 | 4.90E−02 |
| B | | | |
| ALT-enzyme level: Above Norm(6)/In Norm(24) | | | |
| miR-206/miR-155 | 0.82 | 0.94 | 8.50E−04 |
| miR-206/miR-132 | 0.81 | 0.94 | 1.40E−03 |
| miR-206/miR-335-5p | 0.80 | 0.93 | 1.70E−03 |
| miR-122/miR-335-5p | 0.74 | 0.92 | 2.80E−03 |
| miR-122/miR-125b | 0.67 | 0.92 | 4.40E−03 |
| miR-206/miR-146a | 0.80 | 0.92 | 2.00E−03 |
| miR-206/miR-491-5p | 0.81 | 0.92 | 1.70E−03 |
| miR-206/miR-107 | 0.80 | 0.92 | 2.00E−03 |
| miR-206/miR-29b | 0.80 | 0.92 | 2.00E−03 |
| miR-122/miR-155 | 0.71 | 0.91 | 3.80E−03 |
| miR-206/miR-181a | 0.81 | 0.91 | 2.00E−03 |
| miR-122/miR-146a | 0.69 | 0.90 | 3.20E−03 |
| miR-122/miR-107 | 0.78 | 0.90 | 4.40E−03 |
| miR-122/miR-29b | 0.74 | 0.90 | 3.80E−03 |
| miR-122/miR-181a | 0.74 | 0.90 | 5.10E−03 |
| miR-206/miR-125b | 0.80 | 0.90 | 2.40E−03 |
| miR-122/miR-132 | 0.74 | 0.89 | 9.20E−03 |
| miR-122/miR-491-5p | 0.73 | 0.88 | 6.90E−03 |
| miR-206/miR-134 | 0.72 | 0.88 | 8.00E−03 |
| miR-433/miR-181a | 0.73 | 0.88 | 5.10E−03 |
| miR-16/miR-155 | 0.75 | 0.87 | 9.20E−03 |
| miR-122/let-7b | 0.64 | 0.86 | 1.60E−02 |
| miR-206/let-7b | 0.70 | 0.86 | 1.10E−02 |
| miR-206/miR-409-3p | 0.73 | 0.86 | 6.90E−03 |
| miR-206/miR-323-3p | 0.74 | 0.86 | 8.00E−03 |
| miR-433/miR-29b | 0.74 | 0.86 | 1.40E−02 |
| miR-16/miR-335-5p | 0.80 | 0.86 | 1.20E−02 |
| miR-16/miR-132 | 0.73 | 0.86 | 1.40E−02 |
| miR-433/miR-146a | 0.72 | 0.85 | 9.20E−03 |

TABLE 12-continued

Differentiation of various RTT clinical subgroups from other RTT subjects. A-subjects with walking/muscle problems; B-subjects with the positive liver enzyme ALT probes; C-subjects with higher than normal cholesterol level.

| Pairs | Accuracy | AUC | P-value |
|---|---|---|---|
| C Cholesterol level: Above Norm(6)/In or Below(24) | | | |
| miR-146a/miR-29b | 0.82 | 0.92 | 1.20E−03 |
| miR-206/miR-122 | 0.75 | 0.89 | 6.00E−03 |
| miR-181a/miR-409-3p | 0.56 | 0.86 | 4.10E−02 |
| miR-335-5p/miR-29b | 0.69 | 0.85 | 1.40E−02 |
| miR-335-5p/let-7b | 0.73 | 0.84 | 1.60E−02 |
| miR-146a/miR-411 | 0.70 | 0.83 | 2.30E−02 |
| miR-107/miR-29b | 0.70 | 0.83 | 2.00E−02 |
| miR-155/miR-125b | 0.58 | 0.83 | 2.00E−02 |
| miR-491-5p/miR-411 | 0.60 | 0.83 | 3.30E−02 |
| miR-146a/miR-432 | 0.68 | 0.82 | 3.30E−02 |
| miR-146a/miR-125b | 0.66 | 0.81 | 4.10E−02 |
| miR-146a/miR-323-3p | 0.62 | 0.81 | 3.70E−02 |
| miR-146a/miR-433 | 0.70 | 0.81 | 3.70E−02 |
| miR-206/miR-125b | 0.68 | 0.81 | 2.30E−02 |
| miR-335-5p/miR-125b | 0.70 | 0.81 | 2.90E−02 |
| miR-335-5p/miR-134 | 0.69 | 0.81 | 3.70E−02 |
| miR-181a/miR-411 | 0.55 | 0.81 | 3.70E−02 |
| miR-181a/miR-134 | 0.59 | 0.81 | 3.70E−02 |
| miR-181a/miR-323-3p | 0.53 | 0.81 | 3.70E−02 |
| miR-491-5p/miR-432 | 0.64 | 0.81 | 3.70E−02 |
| miR-146a/miR-409-3p | 0.68 | 0.80 | 3.70E−02 |
| miR-146a/miR-134 | 0.67 | 0.80 | 4.10E−02 |
| miR-491-5p/miR-409-3p | 0.64 | 0.80 | 4.60E−02 |

Thus, the data obtained herein indicate that due to differences in plasma concentrations of some miRNAs during disease progression miRNA analysis can be used for various applications, including:
1. Rett screening and diagnosis.
2. Prediction and diagnosis of pathology in different organs.
3. Disease monitoring.
4. Patients enrollment for clinical trials.
5. Drug development and treatment monitoring.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

What is claimed is:

1. A method for detecting Rett Syndrome (RTT) in a subject, which method comprises:
   a) measuring the level of a first miRNA in a bodily fluid sample collected from the subject;
   b) measuring the level of a second miRNA in the bodily fluid sample collected from the subject;
   c) calculating the ratio of the level of the first miRNA (numerator) measured in step (a) to the level of the second miRNA (denominator) measured in step (b), wherein said numerator/denominator miRNA ratio is selected from miR-107/miR-323-3p, miR-107/miR-335-5p, miR-491-5p/miR-323-3p, miR-491-5p/miR-335-5p, miR-491-5p/miR-132, miR-491-5p/miR-411, miR-411/miR-335-5p, miR-411/miR-132, miR-107/miR-132, miR-323-3p/miR-335-5p, miR-323-3p/miR-132, miR-122/miR-125b, miR-155/miR125b, miR-433/mir-323-3p, miR-181a/miR-491-5p, miR-181a/miR-125b, miR-181a/miR-16, miR-181a/let-7b, miR-181a/miR-132, miR-181a/miR-155, miR-181a/miR-29b, miR-432/miR-335-5p, miR-155/miR-125b, miR-155/let-7b, miR-155/miR-132, miR-122/miR-125b, miR-122/miR-155, miR-181a/let-7b, miR-122/miR-132, miR-181a/miR-132, miR-181a/miR-29b, miR-181a/miR-335-5p, miR-107/miR-491-5p, miR-122/miR-125b, miR-122/let-7b, miR-122/miR-29b, miR-122/miR-132, miR-433/miR-491-5p, miR-335-5p/miR-491-5p, miR-181a/miR-155, miR-146a/miR-132, miR-411/miR-125b, miR-432/miR-125b, miR-181a/miR-125b, miR-107/miR-125b, miR-433/miR-125b, miR-491-5p/miR-125b, miR-181a/miR-132, miR-181a/let-7b, miR-181a/miR-155, miR-411/miR-323-3p, miR-491-5p/miR-335-5p, miR-433/miR-491-5p, miR-122/miR-107, miR-132/miR-491-5p, miR-132/miR-335-5p, miR-125b/miR-335-5p, miR-206/miR-125b, miR-206/miR-491-5p, miR-206/miR-29b, miR-206/miR-107, miR-206/miR-132, miR-206/miR-335-5p, miR-206/miR-155, miR-206/miR-16, miR-206/miR-323-3p, miR-206/miR-146a, and miR-122/miR-181a;
   d) comparing the ratio of the levels of the miRNAs calculated in step (c) with a corresponding control ratio, wherein the control ratio (i) is a predetermined value which represents a statistically validated threshold ratio of the levels of said first and second miRNAs, wherein the statistically validated threshold ratio is equal to the highest possible value within the range of corresponding values in matched healthy subjects or (ii) is the ratio of the levels of said first and second miRNAs in a similarly processed bodily fluid sample from the same subject collected in the past; and
   e) (i) identifying the subject as being afflicted with RTT when the ratio of the levels of the miRNAs calculated in step (c) is higher than the corresponding control ratio or (ii) identifying the subject as not being afflicted with RTT when the ratio of the levels of the miRNA calculated in step (c) is not higher than the corresponding control ratio.

2. A method for treating Rett Syndrome (RTT) in a subject in need thereof, which method comprises steps (a) through (d) of the method of claim 1, and which method further comprises
   e) administering a therapeutic or preventive treatment to the subject when the ratio of the levels of the miRNAs calculated in step (c) is higher than the corresponding control ratio, wherein the therapeutic or preventive treatment is selected from gene therapies, reactivation of the inactivated X chromosome, reactivation of a normal allele of inactivated MECP2 gene, hydrotherapy, physical therapies, occupational therapies, speech therapies, language therapies, nutritional support, controlling seizures, controlling muscle stiffness, gastrointestinal treatments, liver treatments, heart treatments, cholesterol-lowering treatments, treatments for breathing problems, and any combinations thereof.

3. A method for selecting subjects for enrollment in a clinical trial involving treatment of Rett Syndrome (RTT), which method comprises steps (a) through (e) of the method of claim 1, and which method further comprises
   f) recruiting the subject in a clinical trial.

4. The method of claim 1, wherein the matched healthy subjects are matched by age.

5. A method for monitoring changes in development of Rett Syndrome (RTT) in a subject, which method comprises performing steps (a) through (c) of the method of claim 1 for two or more bodily fluid samples collected from the subject, wherein the samples have been collected at spaced apart time points, and further comprising comparing the ratios of the levels of the miRNA calculated in step (c) between the earlier collected and later collected bodily fluid sample(s), and (i) determining that RTT in the subject has progressed if the ratio of the levels of the miRNA calculated in step (c) is increased in the later collected bodily fluid sample(s) as compared to the earlier collected sample(s), or (ii) determining that RTT in the subject has not progressed if the ratio of the levels of the miRNA calculated in step (c) is not changed in the later collected bodily fluid sample(s) as compared to the earlier collected sample(s).

6. A method for monitoring the effect of a treatment on development of Rett Syndrome (RTT) in a subject, which method comprises:
   a) collecting one or more bodily fluid sample(s) from the subject prior to initiation of the treatment,
   b) administering the treatment to the subject,
   c) collecting one or more bodily fluid sample(s) from the subject in the course of or following the treatment,
   d) measuring the level of a first miRNA in the one or more bodily fluid sample(s) collected from the subject prior to initiation of the treatment;
   e) measuring the level of a second miRNA in the same bodily fluid sample(s) as in step (d);
   f) calculating the ratio of the level of the first miRNA (numerator) measured in step (d) to the level of the second miRNA (denominator) measured in step (e), wherein said numerator/denominator miRNA ratio is selected from miR-107/miR-323-3p, miR-107/miR-335-5p, miR-491-5p/miR-323-3p, miR-491-5p/miR-335-5p, miR-491-5p/miR-132, miR-491-5p/miR-411, miR-411/miR-335-5p, miR-411/miR-132, miR-107/miR-132, miR-323-3p/miR-335-5p, miR-323-3p/miR-132, miR-122/miR-125b, miR-155/miR125b, miR-433/mir-323-3p, miR-181a/miR-491-5p, miR-181a/miR-125b, miR-181a/miR-16, miR-181a/let-7b, miR-181a/miR-132, miR-181a/miR-155, miR-181a/miR-29b, miR-432/miR-335-5p, miR-155/miR-125b, miR-155/let-7b, miR-155/miR-132, miR-122/miR-125b, miR-122/miR-155, miR-181a/let-7b, miR-122/miR-132, miR-181a/miR-132, miR-181a/miR-29b, miR-181a/miR-335-5p, miR-107/miR-491-5p, miR-122/miR-125b, miR-122/let-7b, miR-122/miR-29b, miR-122/miR-132, miR-433/miR-491-5p, miR-335-5p/miR-491-5p, miR-181a/miR-155, miR-146a/miR-132, miR-411/miR-125b, miR-432/miR-125b, miR-181a/miR-125b, miR-107/miR-125b, miR-433/miR-125b, miR-491-5p/miR-125b, miR-181a/miR-132, miR-181a/let-7b, miR-181a/miR-155, miR-411/miR-323-3p, miR-491-5p/miR-335-5p, miR-433/miR-491-5p, miR-122/miR-107, miR-132/miR-491-5p, miR-132/miR-335-5p, miR-125b/miR-335-5p, miR-206/miR-125b, miR-206/miR-491-5p, miR-206/miR-29b, miR-206/miR-107, miR-206/miR-132, miR-206/miR-335-5p, miR-206/miR-155, miR-206/miR-16, miR-206/miR-323-3p, miR-206/miR-146a, and miR-122/miR-181a;
   g) measuring the level of the same first miRNA as in step (d) in the one or more bodily fluid sample(s) collected from the subject in the course of or following the treatment;
   h) measuring the level of the same second miRNA as in step (e) in the same bodily fluid sample(s) as in step (g);
   i) calculating the ratio of the levels of the miRNA measured in steps (g) and (h) for each bodily fluid sample;
   j) comparing the ratios of the levels of the miRNA calculated in steps (f) and (i), and optionally comparing the ratios of the levels of the miRNA calculated in step (i) between different samples in step (g), and
   k) (1) determining that the treatment is effective for RTT if the ratio of the levels of the miRNA calculated in step (f) is higher than the corresponding ratio(s) calculated in step (i), or (2) determining that the treatment is not effective for RTT if the ratio of the levels of the miRNA calculated in step (f) is not higher than the corresponding ratio(s) calculated in step (i).

7. A method for identifying a compound useful for slowing down the progression or treating Rett Syndrome (RTT) in a subject, which method comprises:
   a) collecting one or more bodily fluid sample(s) from the subject prior to a test compound administration,
   b) administering the test compound to the subject,
   c) collecting one or more bodily fluid sample(s) from the subject following administration of the test compound,
   d) measuring the level of a first miRNA in the one or more bodily fluid sample(s) collected from the subject prior to test compound administration;
   e) measuring the level of a second miRNA in the same bodily fluid sample(s) as in step (d);
   f) calculating the ratio of the level of the first miRNA (numerator) measured in step (d) to the level of the second miRNA (denominator) measured in step (e), wherein said numerator/denominator miRNA ratio is selected from miR-107/miR-323-3p, miR-107/miR-335-5p, miR-491-5p/miR-323-3p, miR-491-5p/miR-335-5p, miR-491-5p/miR-132, miR-491-5p/miR-411, miR-411/miR-335-5p, miR-411/miR-132, miR-107/miR-132, miR-323-3p/miR-335-5p, miR-323-3p/miR-132, miR-122/miR-125b, miR-155/miR125b, miR-433/mir-323-3p, miR-181a/miR-491-5p, miR-181a/miR-125b, miR-181a/miR-16, miR-181a/let-7b, miR-181a/miR-132, miR-181a/miR-155, miR-181a/miR-29b, miR-432/miR-335-5p, miR-155/miR-125b, miR-155/let-7b, miR-155/miR-132, miR-122/miR-125b, miR-122/miR-155, miR-181a/let-7b, miR-122/miR-132, miR-181a/miR-132, miR-181a/miR-29b, miR-181a/miR-335-5p, miR-107/miR-491-5p, miR-122/miR-125b, miR-122/let-7b, miR-122/miR-29b, miR-122/miR-132, miR-433/miR-491-5p, miR-335-5p/miR-491-5p, miR-181a/miR-155, miR-146a/miR-132, miR-411/miR-125b, miR-432/miR-125b, miR-181a/miR-125b, miR-107/miR-125b, miR-433/miR-125b, miR-491-5p/miR-125b, miR-181a/miR-132, miR-181a/let-7b, miR-181a/miR-155, miR-411/miR-323-3p, miR-491-5p/miR-335-5p, miR-433/miR-491-5p, miR-122/miR-107, miR-132/miR-491-5p, miR-132/miR-335-5p, miR-125b/miR-335-5p, miR-206/miR-125b, miR-206/miR-491-5p, miR-206/miR-29b, miR-206/miR-107, miR-206/miR-132, miR-206/miR-335-5p, miR-206/miR-155, miR-206/miR-16, miR-206/miR-323-3p, miR-206/miR-146a, and miR-122/miR-181a;
   g) measuring the level of the same first miRNA as in step (d) in one or more bodily fluid samples collected from the subject following administration of the test compound;
   h) measuring the level of the same second miRNA as in step (e) in the same bodily fluid sample(s) as in step (g);

i) calculating the ratio of the levels of the miRNAs measured in steps (g) and (h) for each of the bodily fluid samples collected from the subject following administration of the test compound;

j) comparing the ratio of the levels of the miRNA calculated in steps (f) and (i), and k) (1) identifying that the test compound is useful for slowing down the progression or treating RTT if the ratio of the levels of the miRNA calculated in step (i) is lower than the ratio of the levels of the miRNA calculated in step (f); (2) identifying that the test compound is not useful for slowing down the progression or treating RTT if the ratio of the levels of the miRNA calculated in step (i) is not lower than the ratio of the levels of the miRNAs calculated in step (f).

8. The method of claim 1, wherein the method comprises measuring the level and calculating the ratios of the levels for two or more different numerator/denominator miRNA pairs.

9. The method of claim 8, wherein the method comprises measuring the level and calculating the ratios of the levels for one or more numerator/denominator miRNA pair combinations selected from the group consisting of:

(a) miR-107/miR-323-3p and miR-107/miR-335-5p;
(b) miR-491-5p/miR-323-3p, miR-491-5p/miR-335-5p, miR-491-5p/miR-132, and miR-491-5p/miR-411;
(c) miR-411/miR-132, miR-107/miR-132 and miR-107/miR-335-5p;
(d) miR-323-3p/miR-335-5p and miR-323-3p/miR-132;
(e) miR-323-3p/miR-335-5p, miR-491-5p/miR-335-5p and miR-411/miR-335-5p;
(f) miR-491-5p/miR-335-5p and miR-491-5p/miR-132;
(g) miR-181a/miR-125b, miR-122/miR-125b and miR-181a/miR-491-5p;
(h) miR-181a/miR-29b, miR-122/miR-125b and miR-411/miR-335-5p;
(i) miR-433/miR-125b, miR-122/miR-125b and miR-181a/miR-335-5p;
(j) miR-122/miR-125b, miR-181a/miR-491-5p and miR-155/miR-125b;
(k) miR-122/miR-125b, miR-181a/miR-491-5p and miR-107/miR-335-5p;
(l) miR-432/miR-335-5p, miR-155/miR-132 and miR-155/let-7b;
(m) miR-432/miR-335-5p, miR-155/let-7b and miR-433/miR-323-3p;
(n) miR-122/miR-125b, miR-181a/miR-29b and miR-107/miR-335-5p;
(o) miR-181a/miR-29b, miR-107/miR-335-5p and miR-122/let-7b;
(p) miR-122/miR-125b, miR-122/miR-29b and miR-433/miR-491-5p; and
(q) miR-433/miR-491-5p, miR-122/miR-146a and miR-335-5p/miR-491-5p.

10. The method of claim 1, wherein the bodily fluid is selected from the group consisting of blood plasma, serum, urine, and saliva.

11. The method of claim 1, wherein the level of the miRNAs is determined using a method selected from the group consisting of hybridization, polymerase chain reaction (PCR)-based detection, sequencing, and microfluidic technologies.

12. The method of claim 2, wherein the therapeutic or preventive treatment is administered prior to appearance of one or more clinical symptoms of RTT.

13. The method of claim 2, wherein the subject does not have clinical symptoms of RTT.

14. The method of claim 1, wherein the subject does not have clinical symptoms of RTT.

* * * * *